United States Patent
Brandizzi et al.

(10) Patent No.: US 11,674,147 B2
(45) Date of Patent: Jun. 13, 2023

(54) EXPRESSION OF UNFOLDED PROTEIN RESPONSE PROTEINS IMPROVES PLANT BIOMASS AND GROWTH

(71) Applicant: Board of Trustees of Michigan State University, East Lansing, MI (US)

(72) Inventors: Federica Brandizzi, Okemos, MI (US); Sang Jin Kim, Okemos, MI (US); Starla Zemelis-Durfee, Dewitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 17/051,683

(22) PCT Filed: May 3, 2019

(86) PCT No.: PCT/US2019/030360
§ 371 (c)(1),
(2) Date: Oct. 29, 2020

(87) PCT Pub. No.: WO2019/213521
PCT Pub. Date: Nov. 7, 2019

(65) Prior Publication Data
US 2021/0317466 A1   Oct. 14, 2021

Related U.S. Application Data

(60) Provisional application No. 62/667,008, filed on May 4, 2018.

(51) Int. Cl.
*C12N 15/82* (2006.01)
(52) U.S. Cl.
CPC ................. *C12N 15/8245* (2013.01)
(58) Field of Classification Search
None
See application file for complete search history.

(56) References Cited

U.S. PATENT DOCUMENTS

2014/0335591 A1   11/2014 Penttila et al.
2016/0251670 A1*  9/2016 Jobling .............. C12N 15/8246
                                                              800/284

FOREIGN PATENT DOCUMENTS

WO   WO-2019213521 A1   11/2019

OTHER PUBLICATIONS

Marcotouli et al, 2018, Scientific Reports, 8: 1-9.*
Kim et al, 2017, Planta, 246:75-89 published on Mar. 31, 2017.*
Hayashi et al, 2012, The Plant Journal, 69:946-956.*
"International Application Serial No. PCT/US2019/030600, International Search Report dated Jul. 17, 2019", 3 pgs.
"International Application Serial No. PCT/US2019/030600, Written Opinion dated Jul. 17, 2019", 6 pgs.
Ermawar, "Metabolic Engineering of C4 Grasses for Biofuel Applications", University of Adelaide, Doctoral Thesis, (Nov. 2015), 1-289.
"International Application Serial No. PCT/US2019/030600, International Preliminary Report on Patentability dated Nov. 19, 2020", 8 pgs.
Bragg, Jennifer N., et al., "Chapter 2—*Brachypodium distachyon*", Agrobacterium Protocols: vol. 1, Methods in Molecular Biology, vol. 1223, (2015), 17-33.
Chen, Yani, et al., "IRE1: ER stress sensor and cell fate executor", *Trends in Cell Biology, 23(11)*, (Nov. 2013), 547-555.
Kim, Sang-Jin, et al., "Modulating hemicellulose to improve bioenergy crop", Abstract, *Great Lakes Bioenergy Research Center (GLBRC) Annual Science Meeting*, May 7-9, 2018, (2018), 2 pgs.

* cited by examiner

*Primary Examiner* — Jason Deveau Rosen
(74) *Attorney, Agent, or Firm* — Schwegman Lundberg & Woessner, P.A.

(57) ABSTRACT

Described herein are expression cassettes, plant cells, plant seeds, plants, and methods useful for improving the glucan content and growth of plants.

14 Claims, 7 Drawing Sheets

Specification includes a Sequence Listing.

EXPRESSION OF UNFOLDED PROTEIN RESPONSE PROTEINS IMPROVES PLANT BIOMASS AND GROWTH

PRIORITY

This application claims the benefit of U.S. Provisional Application Ser. No. 62/667,008, filed May 4, 2018, which application is incorporated by reference herein its entirety.

GOVERNMENT SUPPORT

This invention was made with government support under DE-FCO2-07ER64494 and DE-SC0018409 awarded by the U.S. Department of Energy. The government has certain rights in the invention.

BACKGROUND OF THE INVENTION

Mixed-linkage glucans are abundant matrix polysaccharide that can occupy up to approximately 40% of the total cell wall in grasses. For example, *Brachypodium* endosperm can have up to 40% mixed-linkage glucans (Guillon et al. J Exp Bot 62(3):1001-15 (2011)). Mixed-linkage glucans are polymers containing β-glucosyl residues with both (1,3) and (1,4) linkages. Diverse roles have been suggested for mixed-linkage glucans including regulation of cell growth, cell wall structure and energy storage. The (1,3;1,4)-β-D-glucan content of grains varies amongst the cereals, with barley, oats and rye having the highest amounts and wheat, maize and rice having relatively low levels.

SUMMARY

Described herein are plants, plant cells, and plant seeds that provide improved growth and glucan content, as well as methods for making and using such plants, plant cells, and plant seeds. The nucleic acids, expression cassettes, plants, seeds and methods described herein can be used to improve the quality and quantity of plant materials for biofuel production and other uses. Methods of cultivating such plant seeds and plants are also described herein that include, for example, harvesting the plants, seeds, or the tissues of the plants. Such methods can also include isolating glucans, polysaccharides, starch, and/or sugars from the plants, seeds, or the tissues of the plants.

For example, plant cells, plant seeds, and plants are described herein that include an expression system with (a) at least one (first) expression cassette comprising a first promoter operably linked to nucleic acid segment encoding an IRE1 polypeptide; and (b) at least one (second) expression cassette comprising a second promoter operably linked to nucleic acid segment encoding a CSLF6 polypeptide.

In addition, methods are described herein that include growing a plant seed or plant having an expression system that includes (a) at least one first expression cassette comprising a first promoter operably linked to nucleic acid segment encoding an IRE1 polypeptide; and (b) at least one second expression cassette comprising a second promoter operably linked to nucleic acid segment encoding a CSLF6 polypeptide, to thereby produce a mature plant.

In some cases, the plant cells, plant seeds, and plants can have a single expression vector encoding both an IRE1 polypeptide and a CSLF6 polypeptide. The expression of the IRE1 polypeptide and the CSLF6 polypeptide can be from a single promoter. Alternatively, expression of the IRE1 polypeptide and the CSLF6 polypeptide can be from two separate promoters.

DESCRIPTION OF THE FIGURES

FIG. 1A illustrates a pJJ271 expression vector that includes a CSLF6 codon-optimized nucleic acid (SEQ ID NO:3) operably linked to a CaMV 35S promoter. FIG. 1B illustrates a p6MoIBISH04 expression vector that includes an IRE1 nucleic acid (SEQ ID NO:10) operably linked to a *Brachypodium* PIN-like protein promoter.

FIG. 4A shows the amounts of MLG in leaves of *Brachypodium* that express CSLF6 (CSLF6OX), or a combination of IRE1 and CSLF6 (Cross #9). FIG. 4B shows the amounts of MLG in stems of *Brachypodium* that express CSLF6 (CSLF6OX), or a combination of IRE1 and CSLF6 (Cross #9).

DETAILED DESCRIPTION

Figure 1A:
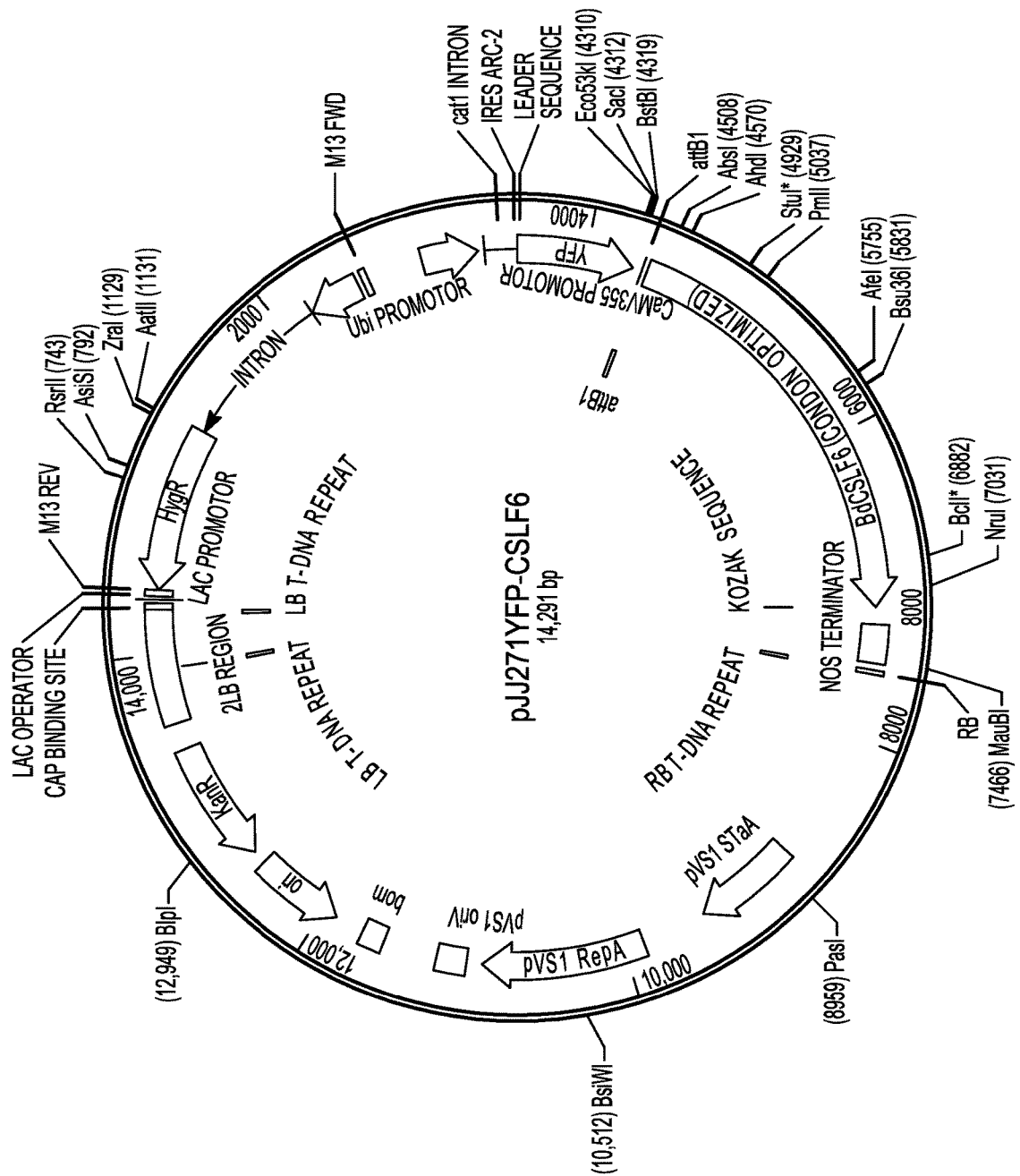
FIG. 1A-1B illustrate expression vectors that can be used.
Figure 1B:
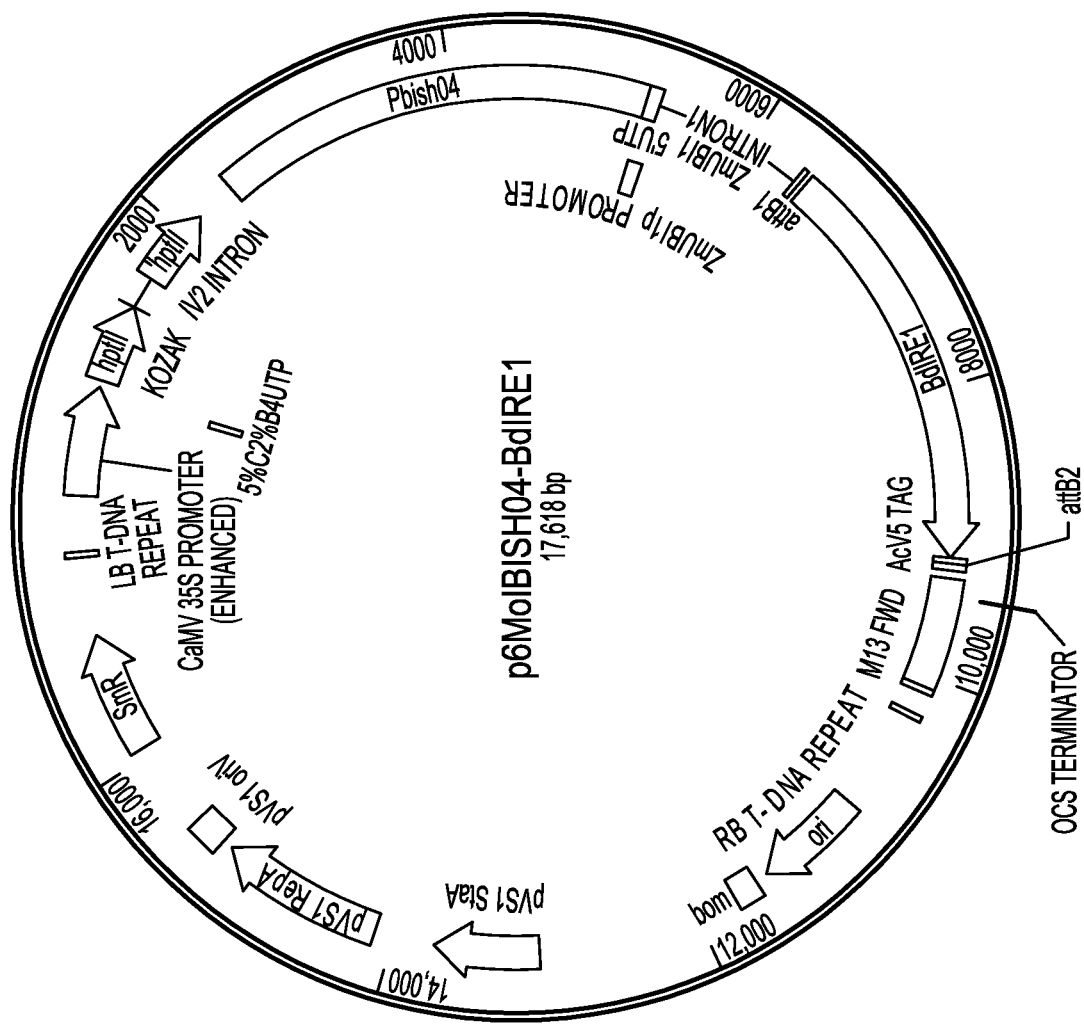

Described herein are expression cassettes, plant cells, plant seeds, plants, and methods useful for improving the glucan content and growth of plants. The plant cells, plant seeds, plants express increased levels of CSLF6 and of an unfolded protein response protein such as IRE1. Such increased expression of CSLF6 and unfolded protein response proteins can be provided by incorporating one or more expression cassettes into the plant cells, plant seeds, and plants.

The diets of humans and livestock rely heavily on cereals storage proteins and carbohydrates, including the simple, yet, important, glucose polymer, mixed-linkage glucan (MLG). Storage proteins and the proteins responsible for the production of MLG are synthesized by the endoplasmic reticulum (ER), an essential organelle of all eukaryotic cells. The ER is highly responsive to the cell's demands for proteins, both in growth and under stress conditions. When protein demands saturate the biosynthetic capacity of the ER, a potentially lethal situation, commonly referred as ER stress, is initiated. At the onset of ER stress, a conserved signaling response, known as the unfolded protein response (UPR), is actuated to mitigate ER stress.

The inventors hypothesized that in view of the essential roles of the ER in building the cell and synthesizing important nutrients, manipulating the unfolded protein response (UPR) in plants could improve the biosynthetic capacity of the ER, as well as plant productivity and stress resilience. Approaches for achieving this goal have largely been unexplored.

As described herein, compared to wild type, transgenic lines with increased UPR exhibit an increase in plant biomass, and can overcome growth penalties associated with glucan over-production.

Mixed-linkage glucan (MLG) is a significant cell wall carbohydrate in grasses and an important carbon source for human consumption and biofuel production. Mixed-linkage glucan biosynthesis depends on the biochemical activity of membrane spanning glucan synthases encoded by the CSLH and CSLF cellulose synthase-like gene families. As illustrated herein, when CSLF6 is overexpressed in plants, those plants exhibit increased glucan content but also exhibit stunted growth. Co-expression of an unfolded protein response protein such as IRE1 significantly improves plant growth and also improves the plant's glucan content.

A variety of CSLF6 proteins and CSLF6 nucleic acids can be used to increase plant glucan content. For example, one sequence of a CSLF6 protein from *Brachypodium distachyon* (Bradi3g16307.1) is shown below as SEQ ID NO:1.

```
  1    MAPAVAGGSS RGAGCKCGFQ VCVCSGSAAV
       ASAGSSLEVE
 41    RAMAVTPVEG QAAPVDGESW VGVELGPDGV
       ETDESGAGVD
 81    DRPVFKTEKI KGVLLHPYRV LIFVRLIAFT
       LFVIWRISHK
121    NPDTMWLWVT SICGEFWFGF SWLLDQLPKL
       NPINRIPDLA
161    VLRQRFDRAD GTSTLPGLDI FVTTADPIKE
       PILSTANSVL
201    SILAADYPVD RNTCYISDDS GMLMTYEAMA
       ESAKFATLWV
241    PFCRKHGIEP RGPESYFELK SHPYMGRAHD
       EFVNDRRRVR
281    KEYDDFKAKI NSLETDIQQR NDLHNAAVPQ
       NGDGIPRPTW
321    MADGVQWQGT WVEPSANHRK GDHAGIVLVL
       IDHPSHDRLP
361    GAPASADNAL DFSGVDTRLP MLVYMSREKR
       PGHNHQKKAG
401    AMNALTRASA LLSNAPFILN LDCDHYINNS
       QALRAGICFM
441    VGRDSDTVAF VQFPQRFEGV DPTDLYANHN
       RIFFDGTLRA
481    LDGMQGPIYV GTGCLFRRIT VYGFDPPRIN
       VGGPCFPALG
521    GLFAKTKYEK PSMEMTMARA NQAVVPAMAK
       GKHGFLPLPK
561    KTYGKSDKFV DTIPRASHPS PYAAEGIRVV
       DSGAETLAEA
601    VKVTGSAFEQ KTGWGSELGW VYDTVTEDVV
       TGYRMHIKGW
641    RSRYCSIYPH AFIGTAPINL TERLFQVLRW
       STGSLEIFFS
681    KNNPLFGSTY LHPLQRVAYI NITTYPFTAI
       FLIFYTTVPA
721    LSFVTGHFIV QRPTTMFYVY LGIVLATLLI
       IAVLEVKWAG
761    VTVFEWFRNG QFWMTASCSA YLAAVCQVLT
       KVIFRRDISF
801    KLTSKLPAGD EKKDPYADLY VVRWTPLMIT
       PIIIIFVNII
841    GSAVAFAKVL DGEWTHWLKV AGGVFFNFWV
       LFHLYPFAKG
881    LLGKHGKTPV VVLVWWAFTF VITAVLYINI
       PHIHGGGKH
921    SVGHGMHHGK KFDGYYLWP
```

A nucleotide sequence that encodes the CSLF6 protein from *Brachypodium distachyon* with SEQ ID NO:1 is shown below as SEQ ID NO:2.

```
  1    ATGGCGCCAG CGGTGGCCGG CGGGAGCAGC
       CGGGGTGCAG
 41    GGTGTAAGTG CGGGTTCCAG GTGTGCGTGT
       GCTCTGGGTC
 81    GGCGGCGGTG GCGTCGGCGG GTTCGTCGCT
       GGAGGTGGAG
121    AGAGCCATGG CGGTGACGCC GGTGGAAGGG
       CAGGCGGCGC
161    CGGTGGACGG CGAGAGCTGG GTCGGCGTCG
       AGCTCGGCCC
```

```
201  CGACGGCGTG GAGACGGACG AGAGCGGCGC
     CGGCGTCGAC

241  GACCGCCCCG TCTTCAAGAC CGAGAAGATC
     AAGGGCGTCC

281  TCCTCCACCC CTACAGGGTG CTGATCTTTG
     TTCGTCTGAT

321  AGCGTTCACC CTGTTCGTGA TCTGGCGTAT
     CTCGCACAAG

361  AACCCGGACA CGATGTGGCT GTGGGTGACC
     TCCATCTGCG

401  GCGAGTTCTG GTTCGGCTTC TCCTGGCTGC
     TGGACCAGCT

441  TCCAAAGCTC AACCCGATCA ACCGGATCCC
     GGACCTCGCC

481  GTGCTCCGGC AACGCTTCGA CCGCGCCGAC
     GGGACATCCA

521  CATTGCCGGG CCTCGACATC TTCGTCACCA
     CGGCCGACCC

561  CATCAAGGAA CCCATCCTGT CGACGGCCAA
     CTCCGTGCTC

601  TCCATCCTGG CCGCCGACTA CCCGGTGGAC
     CGCAACACCT

641  GCTACATCTC CGACGACAGC GGCATGCTCA
     TGACCTACGA

681  GGCCATGGCG GAGTCGGCCA AGTTCGCCAC
     CCTCTGGGTG

721  CCATTCTGCC GCAAGCACGG CATCGAACCA
     CGCGGGCCGG

761  AGAGCTACTT CGAGCTCAAG TCGCACCCGT
     ACATGGGGAG

801  AGCGCACGAC GAGTTCGTCA ATGACCGCCG
     CCGGGTGCGC

841  AAGGAGTATG ATGACTTCAA GGCCAAGATT
     AACTCTCTGG

881  AGACTGATAT CCAGCAGAGG AATGATCTGC
     ATAACGCTGC

921  CGTGCCGCAG AATGGGGATG GGATCCCCAG
     GCCTACCTGG

961  ATGGCTGATG GAGTCCAGTG GCAGGGGACT
     TGGGTCGAGC

1001 CGTCCGCTAA TCACCGCAAG GGAGACCACG
     CCGGCATCGT

1041 CCTGGTTCTG ATTGACCACC CGAGCCACGA
     CCGCCTTCCC

1081 GGCGCGCCGG CGAGCGCCGA CAACGCGCTG
     GACTTCAGCG

1121 GCGTGGACAC CCGCCTCCCG ATGCTCGTCT
     ACATGTCCCG

1161 CGAGAAGCGC CCAGGCCACA ACCACCAGAA
     GAAGGCCGGC

1201 GCCATGAACG CGCTCACCAG GGCTTCCGCG
     CTGCTCTCCA

1241 ACGCGCCCTT CATCCTCAAC CTCGACTGCG
     ACCACTACAT

1281 CAACAACTCC CAGGCCCTCC GCGCCGGGAT
     CTGCTTCATG

1321 GTCGGCCGGG ACAGCGACAC CGTCGCCTTC
     GTGCAGTTCC

1361 CGCAGCGGTT CGAGGGCGTC GACCCCACGG
     ACCTCTACGC

1401 CAACCACAAC CGCATCTTCT TCGACGGCAC
     CCTCAGGGCG

1441 CTCGACGGAA TGCAAGGCCC GATCTATGTC
     GGCACGGGAT

1481 GCCTCTTCCG GCGCATCACC GTCTACGGCT
     TCGACCCGCC

1521 CAGGATCAAC GTCGGCGGGC CATGCTTCCC
     TGCTCTCGGT

1561 GGCCTGTTCG CCAAGACCAA GTATGAGAAG
     CCCAGCATGG

1601 AGATGACCAT GGCGAGAGCC AACCAGGCCG
     TGGTGCCGGC

1641 CATGGCCAAG GGGAAGCACG GCTTCCTGCC
     GCTCCCCAAG

1681 AAGACGTACG GAAGTCCGA CAAGTTCGTG
     GACACCATCC

1721 CGCGCGCGTC CCACCCGTCG CCGTACGCGG
     CGGAGGGGAT

1761 CCGCGTGGTG GACTCCGGCG CGGAGACTCT
     GGCTGAGGCC
```

```
1801  GTCAAGGTGA CCGGATCGGC ATTCGAGCAG
      AAGACCGGAT
1841  GGGGCAGCGA GCTCGGCTGG GTCTACGACA
      CTGTCACAGA
1881  GGACGTGGTG ACTGGCTACA GGATGCACAT
      CAAGGGCTGG
1921  AGGTCCCGCT ACTGCTCCAT CTACCCGCAC
      GCCTTCATCG
1961  GCACCGCCCC GATCAACCTC ACGGAGCGGC
      TCTTCCAGGT
2001  GCTCCGCTGG TCCACCGGCT CCCTCGAGAT
      CTTCTTCTCC
2041  AAGAACAACC CGCTCTTCGG CAGCACCTAC
      CTGCACCCGC
2081  TCCAGCGCGT CGCCTACATC AACATCACCA
      CATACCCGTT
2121  CACCGCCATC TTCCTCATCT TCTACACCAC
      CGTGCCGGCG
2161  CTCTCCTTCG TCACCGGCCA CTTCATCGTG
      CAGCGCCCGA
2201  CGACCATGTT CTACGTCTAC CTGGGGATCG
      TGCTGGCGAC
2241  GCTGCTCATC ATCGCTGTTC TTGAGGTCAA
      GTGGGCTGGA
2281  GTGACAGTGT TCGAGTGGTT CAGGAACGGG
      CAGTTCTGGA
2321  TGACGGCTAG CTGCTCCGCC TACCTTGCTG
      CTGTGTGCCA
2361  GGTGCTCACC AAGGTGATCT TCAGGAGGGA
      CATCTCATTC
2401  AAGCTCACTT CCAAGCTGCC TGCTGGGGAC
      GAGAAGAAGG
2441  ACCCCTATGC CGATCTGTAC GTGGTGCGTT
      GGACTCCACT
2481  CATGATCACT CCAATCATCA TCATCTTCGT
      CAACATCATC
2521  GGCTCGGCGG TGGCCTTCGC CAAGGTGCTG
      GACGGCGAGT
2561  GGACGCACTG GCTCAAGGTG GCGGGAGGAG
      TCTTCTTCAA
2601  CTTCTGGGTG CTGTTCCACC TCTACCCGTT
      CGCCAAGGGT
2641  CTCCTGGGGA AGCATGGCAA GACCCCCGTC
      GTCGTGCTCG
2681  TCTGGTGGGC ATTCACCTTC GTCATCACCG
      CCGTCCTCTA
2721  CATCAACATC CCGCACATCC ATGGAGGAGG
      AGGCAAGCAC
2761  AGCGTGGGGC ATGGGATGCA CCATGGCAAG
      AAGTTCGACG
2801  GCTACTACCT CTGGCCGTGA
```

A nucleotide sequence that encodes the CSLF6 protein from *Brachypodium distachyon* with SEQ ID NO:1 and that has been codon-optimized for expression in *Brachypodium distachyon* is shown below as SEQ ID NO:3.

```
1     ATGGCTCCAG CTGTTGCTGG CGGCTCCTCT
      AGGGGCGCTG
41    GCTGCAAGTG CGGCTTCCAG GTGTGCGTGT
      GCTCCGGCTC
81    TGCCGCCGTG GCCTCCGCCG GCTCATCCCT
      CGAGGTCGAG
121   AGGGCCATGG CTGTTACCCC AGTTGAGGGC
      CAGGCCGCTC
161   CAGTGGACGG CGAGTCCTGG GTGGGCGTTG
      AGCTTGGCCC
201   AGACGGCGTC GAGACCGACG AGTCCGGCGC
      TGGCGTGGAC
241   GACAGGCCAG TGTTCAAGAC CGAGAAGATC
      AAGGGCGTGC
281   TCCTCCACCC ATACAGGGTG CTCATCTTCG
      TGAGGCTGAT
321   CGCCTTCACC CTCTTCGTGA TCTGGCGCAT
      CTCCCACAAG
361   AACCCGGACA CCATGTGGCT CTGGGTGACC
      TCTATTTGCG
401   GCGAGTTCTG GTTCGGCTTC TCCTGGCTCC
      TCGACCAGCT
441   CCCAAAGCTC AACCCGATCA ACCGCATCCC
      AGATCTCGCC
481   GTTCTCAGGC AGAGGTTCGA TAGGGCCGAC
      GGCACCTCCA
```

-continued

| | |
|---|---|
| 521 | CCCTCCCAGG CCTTGATATT TTCGTGACCA CCGCCGACCC |
| 561 | CATCAAGGAG CCAATTCTCT CAACCGCCAA CTCCGTGCTC |
| 601 | TCTATCCTCG CCGCCGATTA CCCGGTGGAT AGGAACACGT |
| 641 | GCTACATCTC CGACGACAGC GGCATGCTCA TGACCTACGA |
| 681 | GGCTATGGCC GAGTCCGCCA AGTTCGCTAC CCTCTGGGTG |
| 721 | CCATTCTGCC GCAAGCACGG CATCGAGCCA AGGGGCCCAG |
| 761 | AGTCCTACTT CGAGCTTAAG TCCCACCCGT ACATGGGCAG |
| 801 | GGCCCATGAC GAGTTCGTGA ACGATAGGCG CAGGGTGAGG |
| 841 | AAGGAGTACG ACGACTTCAA GGCCAAGATC AACTCCCTCG |
| 881 | AGACGGACAT CCAGCAGAGG AACGACCTCC ATAACGCCGC |
| 921 | CGTGCCACAC AACGGGGACG GCATCCCAAG GCCAACCTGG |
| 961 | ATGGCCGATG GCGTGCAGTG GCAGGGCACC TGGGTTGAGC |
| 1001 | CATCTGCCAA CCATAGGAAG GGCGATCACG CCGGCATTGT |
| 1041 | GCTCGTGCTC ATCGACCATC CATCCCACGA CAGGCTCCCA |
| 1081 | GGCGCCCCAG CCTCTGCCGA CAACGCCCTC GACTTCTCCG |
| 1121 | GCGTGGACAC CAGGCTTCCA ATGCTCGTTT ACATGTCCCG |
| 1161 | CGAGAAGAGG CCAGGCCACA ACCACCAGAA GAAGGCTGGC |
| 1201 | GCTATGAACG CCCTTACCAG GGCTTCTGCT CTCCTCTCCA |
| 1241 | ACGCCCCGTT CATCCTCAAC CTCGACTGCG ACCACTACAT |
| 1281 | CAACAACAGC CAGGCTCTCA GGGCCGGCAT CTGCTTCATG |
| 1321 | GTGGGCAGGG ATTCTGACAC CGTGGCCTTC GTTCAGTTCC |
| 1361 | CGCAGCGCTT CGAGGGGGTT GACCCAACCG ATCTCTACGC |
| 1401 | CAACCACAAC AGGATTTTCT TCGATGGCAC CCTCAGGGCC |
| 1441 | CTCGATGGCA TGCAGGGCCC TATCTACGTG GGCACCGGCT |
| 1481 | GCCTCTTCAG GCGCATCACC GTGTACGGCT TCGACCCGCC |
| 1521 | AAGGATTAAC GTTGGCGGCC CATGCTTCCC AGCTCTCGGC |
| 1561 | GGCCTCTTCG CTAAGACCAA GTACGAGAAG CCCAGCATGG |
| 1601 | AGATGACCAT GGCCAGGGCC AACCAGGCCG TTGTTCCAGC |
| 1641 | TATGGCTAAG GGGAAGCACG GCTTCCTGCC ACTCCCGAAG |
| 1681 | AAGACCTACG GCAAGAGCGA CAAGTTCGTC GACACCATTC |
| 1721 | CAAGGGCCTC CCACCCATCT CCATACGCTG CCGAGGGCAT |
| 1761 | TAGGGTTGTG GACTCTGGCG CCGAGACCCT CGCCGAGGCC |
| 1801 | GTGAAGGTGA CCGGCTCCGC CTTCGAGCAG AAGACCGGCT |
| 1841 | GGGGCTCCGA GCTTGGCTGG GTTTACGACA CCGTGACCGA |
| 1881 | GGATGTGGTC ACCGGCTACA GGATGCACAT TAAGGGCTGG |
| 1921 | CGCAGCAGGT ACTGCTCCAT CTACCCACAT GCCTTCATCG |
| 1961 | GCACCGCCCC CATTAACCTC ACCGAGAGGC TTTTCCAGGT |
| 2001 | GCTCAGGTGG TCTACCGGCA GCCTCGAGAT CTTCTTCAGC |
| 2041 | AAGAACAACC CGCTGTTCGG CTCCACCTAC CTGCATCCAC |
| 2081 | TCCAGAGGGT GGCCTACATT AACATCACCA CCTACCCGTT |

| | |
|---|---|
| 2121 | CACCGCCATC TTCCTCATCT TCTACACGAC CGTGCCCGCC |
| 2161 | CTCTCATTCG TGACCGGCCA TTTCATTGTG CAGAGGCCGA |
| 2201 | CCACCATGTT CTACGTGTAC CTCGGGATCG TGCTCGCCAC |
| 2241 | CCTCCTCATT ATTGCCGTGC TCGAGGTTAA GTGGGCTGGC |
| 2281 | GTGACCGTGT TCGAGTGGTT CCGCAACGGC CAGTTCTGGA |
| 2321 | TGACCGCCTC TTGCTCTGCT TACCTCGCCG CTGTTTGCCA |
| 2361 | GGTCCTCACC AAGGTTATCT TCCGCAGGGA CATCTCCTTC |
| 2401 | AAGCTCACCT CCAAGCTCCC AGCCGGCGAC GAGAAGAAGG |
| 2441 | ACCCATACGC CGATCTGTAC GTGGTGAGGT GGACCCCGCT |
| 2481 | CATGATCACC CCGATCATCA TCATTTTCGT CAACATCATC |
| 2521 | GGCTCCGCGG TCGCCTTCGC CAAGGTGCTC GATGGCGAGT |
| 2561 | GGACCCATTG GCTTAAGGTC GCCGGCGGCG TGTTCTTCAA |
| 2601 | CTTCTGGGTT CTCTTCCACC TCTACCCTTT CGCGAAGGGC |
| 2641 | CTTCTTGGCA AGCACGGCAA GACCCCAGTG GTGGTTCTTG |
| 2681 | TCTGGTGGGC CTTCACCTTC GTCATCACCG CCGTGCTGTA |
| 2721 | CATCAACATC CCGCACATCC ATGGCGGCGG CGGCAAGCAC |
| 2761 | TCCGTGGGCC ACGGCATGCA CCATGGCAAG AAGTTCGACG |
| 2801 | GCTACTACCT CTGGCCGTGA |

A nucleotide sequence that encodes the CSLF6 protein from *Brachypodium distachyon* with an N-terminally fused yellow fluorescent protein (YFP) is shown below as SEQ ID NO:4.

| | |
|---|---|
| 1 | ATGGGCAAGG GCGAGGAGCT GTTCACCGGG GTGGTGCCCA |
| 41 | TCCTGGTCGA GCTGGACGGC GACGTAAACG GCCACAAGTT |
| 81 | CAGCGTGTCC GGCGAGGGCG AGGGCGATGC CACCTACGGC |
| 121 | AAGCTGACCC TGAAGTTCAT CTGCACCACC GGCAAGCTGC |
| 161 | CCGTGCCCTG GCCCACCCTC GTGACCACCT TCGGCTACGG |
| 201 | CCTGCAGTGC TTCGCCCGCT ACCCCGACCA CATGAAGCAG |
| 241 | CACGACTTCT TCAAGTCCGC CATGCCCGAA GGCTACGTCC |
| 281 | AGGAGCGCAC CATCTTCTTC AAGGACGACG GCAACTACAA |
| 321 | GACCCGCGCC GAGGTGAAGT TCGAGGGCGA CACCCTGGTG |
| 361 | AACCGCATCG AGCTGAAGGG CATCGACTTC AAGGAGGACG |
| 401 | GCAACATCCT GGGGCACAAG CTGGAGTACA ACTACAACAG |
| 441 | CCACAACGTC TATATCATGG CCGACAAGCA GAAGAACGGC |
| 481 | ATCAAGGTGA ACTTCAAGAT CCGCCACAAC ATCGAGGACG |
| 521 | GCAGCGTGCA GCTCGCCGAC CACTACCAGC AGAACACCCC |
| 561 | CATCGGCGAC GGCCCCGTGC TGCTGCCCGA CAACCACTAC |
| 601 | CTGAGCTACC AGTCCGCCCT GAGCAAAGAC CCCAACGAGA |
| 641 | AGCGCGATCA CATGGTCCTG CTGGAGTTCG TGACCGCCGC |
| 681 | CGGGATCACT CTCGGCATGG ACGAGCTGTA CAAGTCCGGA |
| 721 | CTCAGATCTC GAGCTCAAGC TTCGAATTCT GCAGTCGACG |
| 761 | GTACCGCGGG CCCGGGATCA TCAACAAGTT TGTACAAAAA |
| 801 | AGCAGGCTCC GAATTCGCCC TTATGGCTCC AGCTGTTGCT |

-continued

| | |
|---|---|
| 841 | GGCGGCTCCT CTAGGGGCGC TGGCTGCAAG TGCGGCTTCC |
| 881 | AGGTGTGCGT GTGCTCCGGC TCTGCCGCCG TGGCCTCCGC |
| 921 | CGGCTCATCC CTCGAGGTCG AGAGGGCCAT GGCTGTTACC |
| 961 | CCAGTTGAGG GCCAGGCCGC TCCAGTGGAC GGCGAGTCCT |
| 1001 | GGGTGGGCGT TGAGCTTGGC CCAGACGGCG TCGAGACCGA |
| 1041 | CGAGTCCGGC GCTGGCGTGG ACGACAGGCC AGTGTTCAAG |
| 1081 | ACCGAGAAGA TCAAGGGCGT GCTCCTCCAC CCATACAGGG |
| 1121 | TGCTCATCTT CGTGAGGCTG ATCGCCTTCA CCCTCTTCGT |
| 1161 | GATCTGGCGC ATCTCCCACA AGAACCCGGA CACCATGTGG |
| 1201 | CTCTGGGTGA CCTCTATTTG CGGCGAGTTC TGGTTCGGCT |
| 1241 | TCTCCTGGCT CCTCGACCAG CTCCCAAAGC TCAACCCGAT |
| 1281 | CAACCGCATC CCAGATCTCG CCGTTCTCAG GCAGAGGTTC |
| 1321 | GATAGGGCCG ACGGCACCTC CACCCTCCCA GGCCTTGATA |
| 1361 | TTTTCGTGAC CACCGCCGAC CCCATCAAGG AGCCAATTCT |
| 1401 | CTCAACCGCC AACTCCGTGC TCTCTATCCT CGCCGCCGAT |
| 1441 | TACCCGGTGG ATAGGAACAC GTGCTACATC TCCGACGACA |
| 1481 | GCGGCATGCT CATGACCTAC GAGGCTATGG CCGAGTCCGC |
| 1521 | CAAGTTCGCT ACCCTCTGGG TGCCATTCTG CCGCAAGCAC |
| 1561 | GGCATCGAGC CAAGGGGCCC AGAGTCCTAC TTCGAGCTTA |
| 1601 | AGTCCCACCC GTACATGGGC AGGGCCCATG ACGAGTTCGT |
| 1641 | GAACGATAGG CGCAGGGTGA GGAAGGAGTA CGACGACTTC |
| 1681 | AAGGCCAAGA TCAACTCCCT CGAGACGGAC ATCCAGCAGA |
| 1721 | GGAACGACCT CCATAACGCC GCCGTGCCAC AGAACGGGGA |
| 1761 | CGGCATCCCA AGGCCAACCT GGATGGCCGA TGGCGTGCAG |
| 1801 | TGGCAGGGCA CCTGGGTTGA GCCATCTGCC AACCATAGGA |
| 1841 | AGGGCGATCA CGCCGGCATT GTGCTCGTGC TCATCGACCA |
| 1881 | TCCATCCCAC GACAGGCTCC CAGGCGCCCC AGCCTCTGCC |
| 1921 | GACAACGCCC TCGACTTCTC CGGCGTGGAC ACCAGGCTTC |
| 1961 | CAATGCTCGT TTACATGTCC CGCGAGAAGA GGCCAGGCCA |
| 2001 | CAACCACCAG AAGAAGGCTG GCGCTATGAA CGCCCTTACC |
| 2041 | AGGGCTTCTG CTCTCCTCTC CAACGCCCCG TTCATCCTCA |
| 2081 | ACCTCGACTG CGACCACTAC ATCAACAACA GCCAGGCTCT |
| 2121 | CAGGGCCGGC ATCTGCTTCA TGGTGGGCAG GGATTCTGAC |
| 2161 | ACCGTGGCCT TCGTTCAGTT CCCGCAGCGC TTCGAGGGGG |
| 2201 | TTGACCCAAC CGATCTCTAC GCCAACCACA ACAGGATTTT |
| 2241 | CTTCGATGGC ACCCTCAGGG CCCTCGATGG CATGCAGGGC |
| 2281 | CCTATCTACG TGGGCACCGG CTGCCTCTTC AGGCGCATCA |
| 2321 | CCGTGTACGG CTTCGACCCG CCAAGGATTA ACGTTGGCGG |
| 2361 | CCCATGCTTC CCAGCTCTCG GCGGCCTCTT CGCTAAGACC |
| 2401 | AAGTACGAGA AGCCCAGCAT GGAGATGACC ATGGCCAGGG |

| | |
|---|---|
| 2441 | CCAACCAGGC CGTTGTTCCA GCTATGGCTA AGGGGAAGCA |
| 2481 | CGGCTTCCTG CCACTCCCGA AGAAGACCTA CGGCAAGAGC |
| 2521 | GACAAGTTCG TCGACACCAT TCCAAGGGCC TCCCACCCAT |
| 2561 | CTCCATACGC TGCCGAGGGC ATTAGGGTTG TGGACTCTGG |
| 2601 | CGCCGAGACC CTCGCCGAGG CCGTGAAGGT GACCGGCTCC |
| 2641 | GCCTTCGAGC AGAAGACCGG CTGGGGCTCC GAGCTTGGCT |
| 2681 | GGGTTTACGA CACCGTGACC GAGGATGTGG TCACCGGCTA |
| 2721 | CAGGATGCAC ATTAAGGGCT GGCGCAGCAG GTACTGCTCC |
| 2761 | ATCTACCCAC ATGCCTTCAT CGGCACCGCC CCCATTAACC |
| 2801 | TCACCGAGAG GCTTTTCCAG GTGCTCAGGT GGTCTACCGG |
| 2841 | CAGCCTCGAG ATCTTCTTCA GCAAGAACAA CCCGCTGTTC |
| 2881 | GGCTCCACCT ACCTGCATCC ACTCCAGAGG GTGGCCTACA |
| 2921 | TTAACATCAC CACCTACCCG TTCACCGCCA TCTTCCTCAT |
| 2961 | CTTCTACACG ACCGTGCCCG CCCTCTCATT CGTGACCGGC |
| 3001 | CATTTCATTG TGCAGAGGCC GACCACCATG TTCTACGTGT |
| 3041 | ACCTCGGGAT CGTGCTCGCC ACCCTCCTCA TTATTGCCGT |
| 3081 | GCTCGAGGTT AAGTGGGCTG GCGTGACCGT GTTCGAGTGG |
| 3121 | TTCCGCAACG GCCAGTTCTG GATGACCGCC TCTTGCTCTG |
| 3161 | CTTACCTCGC CGCTGTTTGC CAGGTCCTCA CCAAGGTTAT |
| 3201 | CTTCCGCAGG GACATCTCCT TCAAGCTCAC CTCCAAGCTC |
| 3241 | CCAGCCGGCG ACGAGAAGAA GGACCCATAC GCCGATCTGT |
| 3281 | ACGTGGTGAG GTGGACCCCG CTCATGATCA CCCCGATCAT |
| 3321 | CATCATTTTC GTCAACATCA TCGGCTCCGC GGTCGCCTTC |
| 3361 | GCCAAGGTGC TCGATGGCGA GTGGACCCAT TGGCTTAAGG |
| 3401 | TCGCCGGCGG CGTGTTCTTC AACTTCTGGG TTCTCTTCCA |
| 3441 | CCTCTACCCT TTCGCGAAGG GCCTTCTTGG CAAGCACGGC |
| 3481 | AAGACCCCAG TGGTGGTTCT TGTCTGGTGG GCCTTCACCT |
| 3521 | TCGTCATCAC CGCCGTGCTG TACATCAACA TCCCGCACAT |
| 3561 | CCATGGCGGC GGCGGCAAGC ACTCCGTGGG CCACGGCATG |
| 3601 | CACCATGGCA AGAAGTTCGA CGGCTACTAC CTCTGGCCGT |
| 3641 | GA |

Such a YFP-CSLF6 nucleic acid is useful for expression of a YFP-CSLF6 fusion protein, which allows visualization of the expression patterns and amounts of YFP-CSLF6 products from a YFP-CSLF6 expression cassette.

CSLF6 proteins and nucleic acids from a variety of species can be used in the plants, seeds, plant cells and methods described herein. For example, a CSLF6 amino acid sequence from wheat (*Triticum aestivum*) can be used that has about 86% sequence identity with the CSLF6 from *Brachypodium distachyon* that has SEQ ID NO:1. This wheat CSLF6 sequence is shown below with SEQ ID NO:5.

| | |
|---|---|
| 1 | MAPAVAGGGR VRSNEPAAAA TAPASGKPCV CGFQVCACTG |
| 41 | SAAVASAASS LDMDIVAMGQ IGAVNDESWV GVELGEDGET |
| 81 | DESGAAVDDR PVFRTEKIKG VLLHPYRVLI FVRLIAFTLF |
| 121 | VIWRISHKNP DAMWLWVTSI CGEFWFGFSW LLDQLPKLNP |
| 161 | INRVPDLAVL RQRFDRPDGT STLPGLDIFV TTADPIKEPI |
| 201 | LSTANSVLSI LAADYPVDRN TCYVSDDSGM LLTYEALAES |

```
241  SKFATLWVPF CRKHGIEPRG PESYFELKSH
     PYMGRAQDEF
281  VNDRRRVRKE YDEFKARINS LEHDIKQRND
     GYNAANAHRE
321  GEPRPTWMAD GTQWEGTWVD ASENHRRGDH
     AGIVLVLLNH
361  PSHRRQTGPP ASADNPLDFS GVDVRLPMLV
     YMSREKRPGH
401  DHQKKAGAMN ALTRASALLS NSPFILNLDC
     NHYINNSQAL
441  RAGICFMVGR DSDTVAFVQF PQRFEGVDPT
     DLYANHNRIF
481  FDGTLRALDG MQGPIYVGTG CLFRRITVYG
     FDPPRINVGG
521  PCFPRLAGLF AKTKYEKPGL EMTMAKAKAA
     PVPAKGKHGF
561  LPLPKKTYGK SDAFVDSIPR ASHPSPYAAA
     AEGIVADEAT
601  IVEAVNVTAA AFEKKTGWGK EIGWVYDTVT
     EDVVTGYRMH
641  IKGWRSRYCS IYPHAFIGTA PINLTERLFQ
     VLRWSTGSLE
681  IFFSKNNPLF GSTYLHPLQR VAYINITTYP
     FTAIFLIFYT
721  TVPALSFVTG HFIVQRPTTM FYVYLGIVLS
     TLLVIAVLEV
761  KWAGVTVFEW FRNGQFWMTA SCSAYLAAVC
     QVLTKVIFRR
801  DISFKLTSKL PSGDEKKDPY ADLYVVRWTP
     LMITPIIIIF
841  VNIIGSAVAF AKVLDGEWTH WLKVAGGVFF
     NFWVLFHLYP
881  FAKGILGKHG KTPVVVLVWW AFTFVITAVF
     YINIPHMHSS
921  GGKHTTVHGH HGKKFVDAGY YNWP
```

A CSLF6 amino acid sequence from barley (*Hordeum vulgare*) has about 86% sequence identity with the CSLF6 from *Brachypodium distachyon* that has SEQ ID NO:1. This barley CSLF6 sequence is shown below with SEQ ID NO:6.

```
1    MAPAVAGGGR VRSNEPVAAA AAAPAASGKP
     CVCGFQVCAC
41   TGSAAVASAA SSLDMDIVAM GQIGAVNDES
     WVGVELGEDG
81   ETDESGAAVD DRPVFRTEKI KGVLLHPYRV
     LIFVRLIAFT
121  LFVIWRISHK NPDAMWLWVT SICGEFWFGF
     SWLLDQLPKL
161  NPINRVPDLA VLRQRFDRPD GTSTLPGLDI
     FVTTADPIKE
201  PILSTANSVL SILAADYPVD RNTCYVSDDS
     GMLLTYEALA
241  ESSKFATLWV PFCRKHGIEP RGPESYFELK
     SHPYMGRAQD
281  EFVNDRRRVR KEYDEFKARI NSLEHDIKQR
     NDGYNAAIAH
321  SQGVPRPTWM ADGTQWEGTW VDASENHRRG
     DHAGIVLVLL
361  NHPSHRRQTG PPASADNPLD LSGVDVRLPM
     LVYVSREKRP
401  GHDHQKKAGA MNALTRASAL LSNSPFILNL
     DCDHYINNSQ
441  ALRAGICFMV GRDSDTVAFV QFPQRFEGVD
     PTDLYANHNR
481  IFFDGTLRAL DGMQGPIYVG TGCLFRRITV
     YGFDPPRINV
521  GGPCFPRLAG LFAKTKYEKP GLEMTTAKAK
     AAPVPAKGKH
561  GFLPLPKKTY GKSDAFVDTI PRASHPSPYA
     AAAEGIVADE
601  ATIVEAVNVT AAAFEKKTGW GKEIGWVYDT
     VTEDVVTGYR
641  MHIKGWRSRY CSIYPHAFIG TAPINLTERL
     FQVLRWSTGS
681  LEIFFSKNNP LFGSTYLHPL QRVAYINITT
     YPFTAIFLIF
721  YTTVPALSFV TGHFIVQRPT TMFYVYLGIV
     LSTLLVIAVL
761  EVKWAGVTVF EWFRNGQFWM TASCSAYLAA
     VCQVLTKVIF
801  RRDISFKLTS KLPSGDEKKD PYADLYVVRW
     TPLMITPIII
```

```
                         -continued
841    IFVNIIGSAV AFAKVLDGEW THWLKVAGGV
       FFNFWVLFHL

881    YPFAKGILGK HGKTPVVVLV WWAFTFVITA
       VLYINIPHMH

921    TSGGKHTTVH GHHGKKLVDT GLYGWLH
```

A CSLF6 amino acid sequence from corn (*Zea mays*) has about 82% sequence identity with the CSLF6 from *Brachypodium distachyon* that has SEQ ID NO:1. This corn CSLF6 sequence is shown below with SEQ ID NO:7.

```
  1    MAAGQQQASG GAKHGCVCGF PVCACAGAAA
       VASAASSADM

41    DRVAVAATEG QIGAVNDESW IAVDLSDDGL
       SADGADPGVA

81    LEDRPVFRTE KIKGVLLHPY RVLIFVRLIA
       FTLFVIWRIS

121    HRNPDALWLW VTSIAGEFWF GFSWLLDQLP
       KLNPINRVPD

161    LAALRQRFDR AGGGAGGGTS LLPGLDVFVT
       TADPFKEPIL

201    STANSVLSIL AADYPVERNT CYLSDDSGML
       LTYEAMAEAA

241    KFATVWVPFC RKHGIEPRGP ESYFDLKSHP
       YMGRSQEDFV

281    NDRRRVRKDY DEFKARINGL DHDIKQRSDA
       YNAARGLKDG

321    EPRATWMADG TQWEGTWVEP SENHRKGDHA
       GIVLVLLNHP

361    SHSRQLGPPA SADNPLDLSM VDVRLPMLVY
       VSREKRPGHN

401    HQKKAGAMNA LTRCSAVLSN SPFILNLDCD
       HYINNSQALR

441    AGICFMLGRD SDTVAFVQFP QRFEGVDPTD
       LYANHNRIFF

481    DGTLRALDGM QGPIYVGTGC LFRRITLYGF
       DPPRINVGGP

521    CFPALGGMFA KAKYEKPGLE LTTTKAAVAK
       GKHGFLPMPK

561    KSYGKSDAFA DTIPMASHPS PFAAASAASV
       VADEATIAEA

601    VAVCAAAYEK KTGWGSDIGW VYGTVTEDVV
       TGYRMHIKGW
```

```
                         -continued
641    RSRYCSIYPH AFIGTAPINL TERLFQVLRW
       STGSLEIFFS

681    RNNPLFGSTF LHPLQRVAYI NITTYPFTAI
       FLIFYTTVPA

721    LSFVTGHFIV QRPTTMFYVY LAIVLGTLLI
       LAVLEVKWAG

761    VTVFEWFRNG QFWMTASCSA YLAAVCQVLV
       KVVFRRDISF

801    KLTSKQPAGD EKKDPYADLY VVRWTWLMVT
       PIIIILVNII

841    GSAVAFAKVL DGEWTHWLKV AGGVFFNFWV
       LFHLYPFAKG

881    ILGRHGKTPV VVLVWWAFTF VITAVLYINI
       PHIHGPGGKH

921    GGAIGRHGGD AHHHGKKFDG YYLWP
```

A CSLF6 amino acid sequence from sorghum (*Sorghum bicolor*) has about 82% sequence identity with the CSLF6 from *Brachypodium distachyon* that has SEQ ID NO:1. This corn CSLF6 sequence is shown below with SEQ ID NO:8.

```
  1    MAPGGGDGRR NGEGQQQANG NNNNNNSNAK
       AKHGCVCGFP

41    VCACAGAAAV ASAASSADMD RVAAAQTEGQ
       IGAVNDESWI

81    AVDLSDDLSG DGGGADPGVA IEDRPVFRTE
       KIKGILLHPY

121    RVLIFVRLIA FTLFVIWRIS HRNPDAMWLW
       VTSIAGEFWF

161    GFSWLLDQLP KLNPINRVPD LAVLRQRFDR
       ADGTSRLPGL

201    DIFVTTADPF KEPILSTANS ILSILAADYP
       VERNTCYLSD

241    DSGMLLTYEA MAEAAKFATV WVPFCRKHGI
       EPRGPESYFE

281    LKSHPYMGRS QEDFVNDRRR VRKEYDEFKA
       RINGLEHDIK

321    QRSDAFNAAR GLKDGEPRAT WMADGNQWEG
       TWVEPSENHR

361    KGDHAGIVYV LLNHPSHSRQ LGPPASADNP
       LDFSMVDVRL

401    PMLVYVSREK RPGFNHEKKA GAMNALTRCS
       AVISNSPFIL
```

```
441  NLDCDHYINN SQALRAGICF MLGRDSDTVA
     FVQFPQRFEG
481  VDPTDLYANH NRIFFDGTLR ALDGMQGPIY
     VGTGCMFRRI
521  TLYGFDPPRI NVGGPCFPSL GGMFAKTKYE
     KPGLELTTKA
561  AVAKGKHGFL PLPKKSYGKS DAFVDTIPRA
     SHPSPFLSAD
601  EAAAIVADEA MITEAVEVCT AAYEKKTGWG
     SDIGWVYGTV
641  TEDVVTGYRM HIKGWRSRYC SIYPHAFIGT
     APINLTERLY
681  QVLRWSTGSL EIFFSRNNPL FGSTFLHPLQ
     RVAYINITTY
721  PFTALFLIFY TTVPALSFVT GHFIVQRPTT
     MFYVYLAIVL
761  GTLLILAVLE VKWAGVTVFE WFRNGQFWMT
     ASCSAYLAAV
801  CQVLVKVVFR RDISFKLTSK QPAGDEKKDP
     YADLYVVRWT
841  WLMVTPIIII LVNIIGSAVA FAKVLDGEWT
     HWLKVAGGVF
881  FNFWVLFHLY PFAKGLLGRH GKTPVVVLVW
     WAFTFVITAV
921  LYINIPHIHG PGGKHGGAIG KHGAAHHGKK
     FDLDNLSYNW
961  P
```

Cells operate a signaling network termed the unfolded protein response (UPR) to monitor protein-folding capacity in the endoplasmic reticulum (ER). Inositol-requiring enzyme 1 (IRE1) is an ER transmembrane sensor that activates the UPR to maintain the ER and cellular function.

An amino acid sequence for an IRE1 unfolded protein response protein from *Brachypodium distachyon* that is assigned SEQ ID NO:9 is shown below.

```
  1  MRSLRRVLFP LVLLSGLAFR GVHFNDAAAP TPLLLPLSPP
 41  PALPSPPLAL PADEGRGDGA DSREIIAAPL PGELLVRPPR
 81  RRSEPTNAVT DAGPHISSEL QFNDDGTIQL VDRLSKSSLW
121  QFSTGPPLSK HVTTANSDLG YLIYPLDQAK LVEVHNGSVM
161  ALPWELDEFI SRTPYVRDSV VTIGSKTSTI FAVDADSGEI
201  IYKHSLPIAL NELGATPVEE APSKLDAGRS GSPNVIVLVR
241  TDYSVSASDL GVHLFNWTRT SFSANYYVKQ SHPDTLEQSS
281  CLRGNIPCFR SDGVPLKLTL PESSTANALV LRDLNKVTTR
321  YDADALRPVA TMMKSLQAAS KSNVVLDSTQ NQTVDDAPGR
361  LVSADPQANR FSNNTHGLLF PVVSLLVVLA WLVSLAYSSK
401  PCRQFVGQLF KPFVHEKKST GLAGKTEKTS KRRKTRKKDG
441  IANGTDICSS SDKENGETGG SNETVYNETY QLTGTALPDG
481  LDGCQIGKLR VHKKEIGKGS NGTVVFEGSY DGREVAVKRL
521  LRSHTDIAQK EIQNLIASDR DPNIVRLYGC DQDDNFVYIS
561  LERCRCSLAD LIQQHIDPSF SDVERIDVEL WRQDGLPSAQ
601  LLKLMRDVVA GIVHLHSLGI IHRDLKPQNV LISKEGPLSA
641  KLSDMGISKR LQEDMTSLSH HGTGYGSSGW QAPEQLRGDS
681  QTRAMDLFSL GCLIFYCITK GKHPFGEYYE RDMNIINNHF
721  DLFVVDHIPE AVHLISQLLQ PKPEMRPTAV YVINHPLFWC
761  PELRLLFLRD TSDRIEKTTE TDLINALESI GYEAFGGKWR
801  EKLDDGLVAD MGRYRKYNFE STRDLLRLIR NKSGHYRELP
841  ADLKELLGSL PEGFDRYFSS RFPKLLIEVY KVMSVHCKDE
881  EAFRKYFIGS SV
```

A nucleotide sequence encoding the IRE1 unfolded protein response protein from *Brachypodium distachyon* is provided below as SEQ ID NO:10.

```
  1  ATGAGGTCGC TCCGCCGGGT CCTCTTCCCG CTCGTCCTCC
 41  TTTCGGGGCT CGCCTTTCGT GGTGTCCACT TCAACGACGC
 81  CGCCGCCCCG ACCCCCCTTC TCCTCCCGCT TTCCCCACCA
121  CCGGCGCTGC CGTCGCCGCC CCTCGCGCTC CCTGCTGACG
161  AAGGGCGAGG GGATGGTGCG GACTCCAGGG AGATCATCGC
201  GGCGCCGCTG CCCGGGGAGC TCCTTGTCAG GCCGCCCCGC
241  CGCCGCTCGG AGCCGACGAA CGCGGTGACC GATGCTGGCC
281  CCCACATCAG CTCCGAACTA CAATTCAACG ACGATGGCAC
321  AATTCAACTT GTTGATCGTC TATCAAAATC TTCTTTGTGG
361  CAGTTCTCCA CAGGACCGCC TCTTTCGAAG CATGTCACTA
401  CAGCAAACTC AGATTTGGGC TATCTCATAT ATCCTTTAGA
441  TCAAGCTAAG CTTGTGGAAG TTCATAATGG CAGTGTTATG
481  GCACTTCCCT GGGAACTGGA CGAGTTTATT AGCAGAACTC
521  CGTATGTACG GGACTCTGTC GTTACTATTG GATCAAAAAC
561  TTCAACTATT TTTGCAGTTG ATGCTGATAG TGGGGAGATC
601  ATTTACAAGC ATAGCTTGCC AATCGCTTTG AATGAATTAG
641  GAGCAACCCC TGTTGAAGAA GCACCATCCA AGCTGGATGC
681  TGGTAGAAGT GGTAGTCCTA ATGTCATAGT GCTTGTTAGA
721  ACTGATTATT CTGTCAGTGC GTCTGACCTA GGCGTTCATT
761  TGTTTAACTG GACAAGAACT TCTTTCTCTG CAAACTATTA
801  TGTGAAACAG AGCCATCCAG ATACGTTAGA ACAATCATCC
841  TGTCTGCGAG GAAATATTCC TTGCTTTAGG TCTGATGGTG
```

```
 881 TACCACTTAA ACTCACGTTA CCTGAGTCTA GTACAGCCAA
 921 TGCACTTGTC TTGAGAGATT TGAACAAAGT TACCACTAGG
 961 TATGATGCTG ATGCCTTGAG ACCAGTTGCA ACTATGATGA
1001 AGTCACTACA AGCTGCTAGC AAGTCTAATG TTGTTCTGGA
1041 CAGTACTCAG AATCAAACTG TTGATGATGC TCCTGGTCGC
1081 CTTGTCTCTG CTGATCCCCA AGCCAACAGG TTCAGTAACA
1121 ATACTCATGG ATTGTTATTC CCTGTTGTTT CCTTATTGGT
1161 GGTCCTCGCT TGGCTAGTGA GCTTGGCCTA TTCAAGCAAG
1201 CCTTGCAGGC AATTCGTGGG TCAGCTTTTT AAGCCATTTG
1241 TCCATGAAAA GAAATCGACA GGCCTTGCAG GAAAGACAGA
1281 GAAAACTTCT AAGAGAAGAA AAACACGAAA GAAAGACGGA
1321 ATTGCCAATG GCACTGATAT CTGTTCATCA TCTGACAAAG
1401 AGAACGGTGA AACTGGTGGG TCAAATGAGA CGGTATATAA
1441 TGAAACCTAC CAATTAACAG GTACCGCACT CCCTGATGGT
1481 CTTGATGGAT GCCAGATTGG TAAGCTTCGT GTTCACAAAA
1521 AAGAAATTGG TAAAGGGAGC AATGGTACAG TTGTCTTTGA
1561 GGGTTCCTAT GATGGTCGTG AAGTTGCAGT GAAACGTCTG
1601 CTACGTTCAC ACACTGATAT AGCGCAAAAA GAGATTCAGA
1641 ATCTTATTGC ATCCGACCGG GATCCTAATA TCGTTAGACT
1681 GTATGGCTGC GATCAGGATG ATAATTTTGT TTATATCTCC
1721 CTTGAGAGAT GCCGCTGCAG CTTGGCTGAT CTTATTCAAC
1761 AGCATATAGA TCCATCATTT TCAGATGTTG AGCGAATAGA
1801 TGTTGAACTG TGGAGGCAGG ATGGGCTCCC TTCCGCACAA
1841 CTCCTAAAGC TGATGAGAGA TGTTGTTGCT GGCATTGTGC
1881 ATTTGCATAG TTTAGGAATC ATACATCGCG ATTTGAAGCC
1921 TCAGAACGTT TTGATAAGTA AGGAAGGACC TCTCAGCGCA
1961 AAACTTTCAG ATATGGGTAT CAGTAAGCGC TTGCAAGAGG
2001 ATATGACTTC TCTTAGCCAT CATGGTACTG GATATGGAAG
2041 CTCTGGTTGG CAAGCACCTG AACAGCTTCG TGGTGATAGT
2081 CAGACTCGTG CAATGGATTT ATTTAGTTTG GGCTGCCTTA
2121 TTTTCTATTG TATCACCAAA GGCAAGCATC CGTTTGGTGA
2201 GTACTATGAG CGGGACATGA ACATTATAAA CAATCACTTT
2241 GATCTCTTCG TGGTGGATCA CATACCAGAA GCAGTACATC
2281 TTATTTCTCA ATTGTTACAG CCAAAACCAG AAATGAGACC
2321 AACGGCAGTA TACGTGATAA ATCATCCTCT CTTCTGGTGC
2361 CCTGAGTTGC GGCTTCTGTT CCTACGGGAT ACCAGTGACA
2401 GAATTGAGAA AACCACTGAA ACTGACCTCA TAAATGCTTT
2441 GGAAAGCATA GGGTATGAAG CGTTTGGTGG AAAATGGCGA
2481 GAAAAGTTGG ATGATGGTCT GGTTGCCGAC ATGGGTCGTT
2521 ATAGGAAATA TAATTTTGAG TCCACACGTG ACCTTCTGAG
2561 GTTGATTAGA AATAAGTCAG GACATTACAG GGAGCTGCCA
2601 GCTGATCTCA AGGAATTACT TGGGTCGCTG CCTGAGGGAT
2641 TTGATCGCTA TTTCTCAAGC CGATTTCCAA AGCTGCTGAT
2681 TGAAGTGTAC AAGGTCATGT CTGTGCACTG CAAGGATGAG
2721 GAAGCTTTCA GGAAATATTT CATTGGAAGC TCGGTATAA
```

An IRE1 amino acid sequence from wheat (*Triticum aestivum*) has about 82% sequence identity with the IRE1 from *Brachypodium distachyon* that has SEQ ID NO:9. This wheat IRE1 sequence is shown below with SEQ ID NO:11.

```
  1 MRSLRRVLLP LVLLSGLAFR GARFEDDADS APAPLLLPLP
 41 LPAPQQPAPS LALPAAGGRG DEAGSTEIVP AEQPFLVRPP
 81 RRRSVPSNAV KNPDVGPGIS SELRFYDNGT IQLVDRLSES
121 PLWQFSTGPP LSKHITTTNS DLSYLIYPLD ESDLVEVHNG
161 TGVKLPWELE EFIARTPYIR DSVVTIGSKA STTFAVDADS
201 GEIIYKHSLP AALNELAVPA GEAPSKLDVG RSSNIIVVVR
241 TDYSLSASDL GVHLFNWTRS SFSANYYVKQ SHPNMLEQSS
281 CLQENIPCIR TDGVPIKLTL PDSSTANALV LQDVNKVTTR
321 DGADALRQLQ TLVIPQQTAS KSGVALNGTQ NQTVDGALVH
361 LVPADPQANR FTNNAYGLLF PVLTLLVVLA WLVRLAYSSK
401 SCKQFMSVLM KPFVREQKSI DLRGKSEGTS KRRKTRKKDG
441 RANSTEIGSA SDKESSGTGG SNEMLYALPD GLDGCQIGKL
481 RVHKKEIGKG SNGTVVFEGS YDGREVAVKR LLRSHTDIAQ
521 KEIQNLIASD RDPNIVRLYG CDQDDNFVYI SLERCRCSLA
561 DLIQQHTDPS FSDVEKIDVE LWTQDGLPSP QLLKLMRDVV
601 AGIVHLHSLG IIHRDLKPQN VLISKEGSLS AKLSDMGISK
641 RLQEDMSSLS HHGTGYGSSG WQAPEQLRRA SQTRAMDLFS
681 LGCLIFYCIT KGKHPFGEYY ERDINIINGH FDLFVVDHIP
721 EAVHLISLLL QPKPDERPTA VYAINHPLFW SPELRLLFLR
761 DTSDRIEKTT ETDLLNALES IGHQAFGGKW REKLDDGLVA
801 DVGRYRKYNF ESTRDLLRLI RNKSGHYREL PADLKELLGS
841 LPEGFDRYFS IRFPKLLIEV YKVMSVYCKD EEDFRKYFIG
881 ISV
```

As illustrated below, the IRE1 amino acid sequence with SEQ ID NO:11 from wheat (*Triticum aestivum*) has about 82-83% sequence identity with the IRE1 from *Brachypodium distachyon* that has SEQ ID NO:9.

```
Seq9   1 MRSLRRVLFPLVLLSGLAFRGVHFNDAA--APTPLLLPLS-PPPALPSPPLALPADEGRG
Seq11  1 MRSLRRVLLPLVLLSGLAFRGARFEDDADSAPAPLLLPLPLPAPQQPAPSLALPAAGGRG
         ******** ************  *  **  ** ******  *   *   ***** ***
```

```
Seq9  58 DGADSREITAAPLPGELLVRPPRRRSEPTNAVT--DAGPHISSELQFNDDGTIQLVDRLS
Seq11 61 DEAGSTEIVPAEQP--FLVRPPRRSVPSNAVKNPDVGPGISSELRFYDNGTIQLVDRLS
         * ** **   * *   ********* ***   * ** ***** ** * *********

Seq9  116 KSSLWQFSTGPPLSKHVTTANSDLGYLIYPLDQAKLVEVHNGSVMALPWELDEFISRTPY
Sq11  119 ESPLWQFSTGPPLSKHITTTNSDLSYLIYPLDESDLVEVHNGTGVKLPWELEEFIARTPY
           * ************ ** **** ******* *     ****** ** *** ** ***
****

Seq9  176 VRDSVVTIGSKTSTIFAVDADSGEITYKHSLPIALNELGATPVEEAPSKLDAGRSGSPNV
Sq11  179 IRDSVVTIGSKASTTFAVDADSGEITYKHSLPAALNEL-AVPAGEAPSKLDVGRSS--NI
          ********** ** ***************** ****  * *  ******* ***    *

Seq9  236 IVLVRTDYSVSASDLGVHLFNWTRTSFSANYYVKQSHPDTLEQSSCLRGNIPCFRSDGVP
Sq11  236 IVVVRTDYSLSASDLGVHLFNWTRSSFSANYYVKQSHPNMLEQSSCLQEDIPCIRTDGVP
          ** ******* ************* *************   *******  **** * ***

Seq9  296 LKLTLPESSTANALVLRDLNKVTTRYDADALRPVATMMKSLQAASKSNVVLDSTQNQTVD
Sq11  296 IKLTLPDSSTANALVLQDVNKVTTRDGADALRQLQTLVIPQQTASKSGVALNGTQNQTVD
           ***** ********* * ******  ***** *    *  * ****  * * *******

Seq9  356 DAPGRLVSADPQANRFSNNTHGLLFPVVSLLVVLAWLVSLAYSSKPCRQFVGQLFKPFVH
Sq11  356 GALVHLVPADPQANRFTNNAYGLLFPVLTLLVVLAWLVRLAYSSKSCKQFMSVLMKPFVR
            *  ** ********* **  ****** ********* ****** * **   * ****

Seq9  416 EKKSTGLAGKTEKTSKRRKTRKKDGIANGTDICSSSDKENGETGGSNETVYNETYQLTGT
Sq11  416 EQKSIDLRGKSEGTSKRRKTRKKDGRANSTEIGSASDKESSGTGGSNEMLY---------
          * **   * **   ************ **  * * ***  ******* *

Seq9  476 ALPDGLDCQIGKLRVHKKEIGKGSNGTVVFEGSYDGREVAVKRLLRSHIDIAQKEIQNL
Sq11  467 ALPDGLDCQIGKLRVHKKEIGKGSNGTVVFEGSYDGREVAVKRLLRSHIDIAQKEIQNL
          **********************************************************

Seq9  536 IASDRDPNIVRLYGCDQDDNFVYISLERCRCSLADLIQQHIDPSFSDVERIDVELWRQDG
Sq11  527 IASDRDPNIVRLYGCDQDDNFVYISLERCRCSLADLIQQHTDPSFSDVEKIDVELWTQDG
          ****************************************  *********** ******

Seq9  596 LPSAQLLKLMRDVVAGIVHLHSLGIIHRDLKPQNVLISKEGPLSAKLSDMGISKRLQEDM
Sq11  587 LPSPQLLKLMRDVVAGIVHLHSLGIIHRDLKPQNVLISKEGSLSAKLSDMGISKRLQEDM
          *** ************************************ ******************

Seq9  656 TSLSHHGTGYGSSGWQAPEQLRGDSQTRAMDLFSLGCLIFYCITKGKHPFGEYYERDMNI
Sq11  647 SSLSHHGTGYGSSGWQAPEQLRRASQTRAMDLFSLGCLIFYCITKGKHPFGEYYERDINI
           *********************  ***********************************  **

Seq9  716 INNHFDLFVVDHIPEAVHLISQLLQPKPEMRPTAVYVINHPLFWCPELRLLFLRDTSDRI
Sq11  707 INGHFDLFVVDHIPEAVHLISLLLQPKPDERPTAVYAINHPLFWSPELRLLFLRDTSDRI
          ** ****************** ******   ****** *******  ****************

Seq9  776 EKTTEIDLINALESIGYEAFGGKWREKLDDGLVADMGRYRKYNFESTRDLLRLIRNKSGH
Sq11  767 EKTTEIDLLNALESIGHQAFGGKWREKLDDGLVADVGRYRKYNFESTRDLLRLIRNKSGH
          ********  ******   *************** ***********************

Seq9  836 YRELPADLKELLGSLPEGFDRYFSSRFPKLLIEVYKVMSVHCKDEEAFRKYFIGSSV
Seq11 827 YRELPADLKELLGSLPEGFDRYFSIRFPKLLIEVYKVMSVYCKDEEDFRKYFIGISV
          ************************ *************** ***** ****** **
```

An IRE1 amino acid sequence from barley (*Hordeum vulgare*) has about 81% sequence identity with the IRE1 from *Brachypodium distachyon* that has SEQ ID NO:9. This barley IRE1 sequence is shown below with SEQ ID NO:12.

```
  1 MRSLRRVLLP LVLLSGLAFR GARFDDADAA PAPLLLPLPL
 41 PPQQPAPSLA LPAGDEAGST EIVAAEQPSL RELLVRPPRR
 81 RSEPANAVLP DTGPGISSEL RFYDNGTIQL VDRRSEAPLW
121 QFSTGPPLSK HITTTNSDLS YLIYPLDESD LVEVHNGTGV
161 KLPWELEEFI ARTPYIRDSV VTIGSKASTT FTVDADSGEI
201 IYKHSLPAAL NELGAVPVGE VPSKLDVGRS SNIIVVVRTD
241 YSLSASDLGV HLFNWTRSSF SANYYVKHSH PDMLEQSSCL
281 QENIPCIRTD GVPLKLTLPD SSTSNALVLR DVDKVTTRDG
321 ADALRLLQTL VIPQQTASKS GVALDGTQNR TVDGALSHLV
361 PADPQTNRFT NNAYGLLFPV LTLLVVLTWL VRLAYSSKSC
401 KQFMSILMKP FVREQKSIDP RGKSEGTSKR RTKKDGRA
441 NSTEIGSASD KESSGTGGSN EMLYALPDGL DGCQIGKLRV
481 HKKEIGKGSN GTVVFEGSYD GREVAVKRLL RSHTDIAQKE
521 IQNLIASDRD PNIVRLYGCD QDDNFVYISL ERCHCSLADL
561 IQQHTDPSFS DVEKIDVELW TQDGLPSPQL LKLMRDVVAG
601 IVHLHSLGII HRDLKPQNVL ISKEGSLSAK LSDMGISKRL
641 QEDMSSLSHH GTGYGSSGWQ APEQLRRASQ TRAMDLFSLG
681 CLIFYCITKG KHPFGEYYER DINIINGHFD LFVVDHIPEA
```

```
721  VHLISLLLQP KPDERPTAMY AINHPLFWSP ELRLLFLRDT

761  SDRIEKTTET DLLNALESIG HQAFGGKWRE KLDDGLVADV

801  GRYRKYNFES TRDLLRLIRN KSGHYRELPT DLKESLGSLP

841  EGFDRYFSSR FPKLLIEVYK VMSVYCKDEE DFRKYFIGSS

881  V
```

An IRE1 amino acid sequence from rice (*Oryza sativa*) has about 78% sequence identity with the IRE1 from *Brachypodium distachyon* that has SEQ ID NO:9. This rice IRE1 sequence is shown below with SEQ ID NO:13.

```
  1   MRSLRRVLLQ LVLLAGVAFR GVRFDDAADA
      AAAAQGSSDL

41   FELPSPSPTL ALPGGGDEGA STEIIAAPWP
      GRHGLFTPPR

81   STSQPARAVV QPAADFGSQL QFYDNGTIQL
      VDLLSKLPRW

121   QFSTGPPLSK HITTSKPDLN YVIYLDGSET
      SDLIEVHNGS

161   GVRLPWKLEE FIAETPYIRD SFVTIGSKVS
      TTFVVNADSG

201   EIIYKHSLPV ALNEVGGPLV EEIPSKLDAA
      RSGTSANIIV

241   VVRTDYSISA SDLGEHLFNW TRTSFTANYY
      ARYGHQDMLA

281   QSSCLRGNIP CIRTEGPPIK LYLPDSSSDN
      AIVLRPVNEV

321   SAVDALEPLL PPKKLPQPAG ESNVALDSAQ
      NQTADIALGH

361   FVPADTELTN SVTKFSYRWL FPTFLMLLIM
      ACLVKLADAS

401   KYCRQFVIRF LKPFMRDEKL MDPRGKSEGT
      SKRRKARKKD

441   GLINSTQIFS ASDKEGNGTG GSTEAQSNKA
      HDSTNVELPN

481   GLNGRQIGKL CVYSKEIGKG SNGTVVFEGS
      YGGREVAVKR

521   LLRSHNDIAS KEIENLIASD QDPNIVRMYG
      FEQDNDFVYI

561   SLERCRCSLA DLIQLHSVPP FSNIKGIDIE
      LWRQDGLPSA

601   QLLKLMRDVV AGIVHLHSLG IIHRDLKPQN
      VLISKEGPLR

641   AKLSDMGISK RLQEDMTSVS HHGTGFGSSG
      WQAPEQLRHG

681   RQTRAIDLFS LGCLIFYCIT KGKHPFGEYY
      ERDMKIINNQ

721   FDLFIVDHIP EAVHLISQLL DPDPEKRPTA
      VYVMHHPFFW

761   SPELCLSFLR DTSDRIEKTS ETDLIDALEG
      INVEAFGKNW

801   GEKLDAALLA DMGRYRKYSF ESTRDLLRLI
      RNKSGHYREF

841   SDDLKELLGS LPEGFVQYFS SRFPKLLIKV
      YEVMSEHCKD

881   EEAFSKYFLG SSA
```

An IRE1 amino acid sequence from sorghum (*Sorghum bicolor*) has about 75% sequence identity with the IRE1 from *Brachypodium distachyon* that has SEQ ID NO:9. This sorghum IRE1 sequence is shown below with SEQ ID NO:14.

```
  1   MRSLRRVLIP LVLLAGLAFR VDDGGAALLP
      PPPPALPAPR

41   PRLALPGGAA PEDDVAAAAA SRSTEIVAVG
      ARSTEIVAPA

81   GPKKQSLREL LVRPQPARHE PANLVSGEAK
      AEPSPVLQFY

121   DNGTIQLVDQ LSQSPMWEIT TGPPLSDHIT
      TTDSGLNYLI

161   YPLMNGNGTE LWEVYNGNNV RLPWKLEEFV
      ARSPYVRDSV

201   VTVGSKVSTV FVVNADSGEI IYRHSIPAVL
      NELEGPGIDG

241   APSKLNARTS DGSEKIIVLV RTDYSLSASD
      LGKHLENWIR

281   TSFTANQYAK YNHPDMLDQS PCLRGDIPCI
      RTEGLPLALP

321   DSDSANVIVL KDGTPFISIH GSDALEPVQT
      SRKLPNTAGK

361   SNIILDDSQN QTYDGARSHV ISADPEATKY
      PTRNTYGWLF

401   PLFPIFLVIG YLLSLTSASK SCRQFVIQLI
      KPFTHDKKSV
```

```
441  DIRGRSEGTP KRRKTRKKDG LANSPETLTA
     SDKECNETGG
481  STEAPMENSA LTDALGGRQI GKLYVSNKEI
     GRGSNGTVVF
521  EGSYDGRQVA VKRLLRSHND IAEKETQNLI
     ISDRDPNIVR
561  LYGCDHDSDF VYISLERCHC SLADLIQKHS
     YLSSGESISN
601  NEVSISIKSK IPNVKGIDVE LWTQDGLPSA
     HLLKLMRDVV
641  AGLVHLHNLG IIHRDLKPQN VLISAEGTIR
     AKLSDMGISK
681  HLQDDMTSVS HHGTGIGSSG WQAPEQLRHG
     RQTRAMDLFS
721  LGCLIFYCIT KGKHPFGEYY ERDMNIVNNR
     FDLFVVDHIP
761  EAVHLISQLL QPNPEIRPTA VYVMHHPLFW
     SPELRLSFLR
801  DTSDRIEKTS ETDLINALES IGPVAFGGKW
     GEKLDAALVT
841  DMGRYRKYNF ESIRDLLRYI RNKSGHYREL
     SEDLKGILGS
881  LPEGFDRYFA SRFPKLLIEV YKVLWVHCKD
     EEAFSKYFNG
921  SSL
```

An IRE1 amino acid sequence from corn (*Zea mays*) has about 64% sequence identity with the IRE1 from *Brachypodium distachyon* that has SEQ ID NO:9. This corn IRE1 sequence is shown below with SEQ ID NO:15.

```
  1  MRSLRGVLIP LVLLAGLAFR VDDGGAALLP
     LPPPALPASP
 41  SRLALPGGTP KDDGAAASRS TEVVTAGVRS
     TEIVAPVGPK
 81  KQSLRELLVR PQPARHEPSS LVSGEAKAET
     RSVLQFYDNG
121  TIQLVDKLSQ SPLWEIATGP PLSDHITTTE
     SGPNYLIYPF
161  NGNENMNGNS TELWEVYNGN SVRLPWKLEE
     FVARSPYIRD
201  SVVTIGSKVS TVFVVDADSG EIIYRHSIPS
     ALKELEGPGV
241  EGAPSKLNVR TSDDSDNIIV LVRTDYSLSA
     SDLGNHLFNW
281  TRTSFTANYY VKYKHPDMLD QSSCLQGDIP
     CIRTEGLPLA
321  LPDLNSANVI VLKDGTPFVS MHGSDALEPV
     QTPRKLPNTA
361  GKSNILLDDS QNQTHDVARS HAISADPEAT
     LNPTRNTSGW
401  LFPLFPIFLV TGYLLSLISA SKSCRQFMIQ
     LIEPFTHNKK
441  TVDIRGRSEG TPKKRKTRKK DGLVNSSETL
     TASDKECSDT
481  GGSTEAPMKN SALTDALGGR QIGKVYVSNK
     EIGRGSNGTI
521  VFEGSYDGRQ VAVKRLLRSH NDIAEKETRN
     LIISDHDPNI
561  VRLYGCDHDS DFVYISLERC HCSLADLIQK
     QSYLSSGESI
601  SNNEVSMSIN SKISNVKGID VELWTQDGLP
     SAQLLKLMRD
641  VVAGLVHLHN LGIIHRDLKP QNVLISAEGP
     IRAKLSDMGI
681  SKHLQDDMTS VSHHGTGIGS SGWQAPEQLR
     HGRQTRAMDL
721  FSLGCLIFYC ITKGKHPFGE YYERDTNIVN
     NRFDLFVVDY
761  IPEAVHLISQ LLQPNPETRP TAVYVMHHPL
     FWSPELRLSF
801  LRDTSDRIEK TSEIDLINAL ESIGPVAFGG
     KWGEKLDAAL
841  VTDMGRYRKY NFESTRDLLR YIRNKSGHYR
     ELSNDLKGIL
881  GSLPEGFDHY FASRFPKLLI EVYKVLWVHC
     KDEEAFSKHF
921  NGSSL
```

The nucleic acids and polypeptides allow identification and isolation of related nucleic acids and their encoded enzymes that provide a means for production of healthy plants with increased glucan.

The related nucleic acids can be isolated and identified by mutation of the SEQ ID NO:2, 3, 4, or 10 nucleic acid sequences and/or by hybridization to DNA and/or RNA isolated from other plant species using segments of these nucleic acids as probes. The sequence of the CSLF6 and IRE1 enzymes (e.g., SEQ ID NO:1, 5, 6, 7, 8, 9, 11, 12, 13, 14, or 15) can also be examined and used a basis for designing alternative CSLF6 and/or IRE1 nucleic acids that encode related CSLF6 and/or IRE1 polypeptides.

The CSLF6 and/or IRE1 nucleic acids described herein can include any nucleic acid that can selectively hybridize to any of SEQ ID NO:2, 3, 4, or 10 nucleic acids.

The term "selectively hybridize" includes hybridization, under stringent hybridization conditions, of a nucleic acid sequence to a specified nucleic acid target sequence (e.g., any of the SEQ ID NO:2, 3, 4, or 10 nucleic acids) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with each other. In some embodiments, a selectively hybridizing sequence has about at least about 80% sequence identity or complementarity with SEQ ID NO:2, 3, 4, or 10.

Thus, the nucleic acids of the invention include those with about 500 of the same nucleotides as SEQ ID NO:2, 3, 4, or 10, or about 600 of the same nucleotides, or about 700 of the same nucleotides, or about 800 of the same nucleotides, or about 900 of the same nucleotides, or about 1000 of the same nucleotides, or about 1100 of the same nucleotides, or about 1200 of the same nucleotides as SEQ ID SEQ ID NO:2, 3, 4, or 10. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., 90-99% sequence identity what is meant is that the value can be any integer between 90 and 99 inclusive, i.e., 90, 91, 92, 93, 94, 95, 96, 97, 98 or 99, or any range between 90 and 99 inclusive, e.g., 91-99%, 91-98%, 92-99%, etc.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution. Thus, high stringency conditions can include a wash that includes 0.1×SSC at 60 to 65° C.

For DNA-DNA hybrids, the $T_m$ can be approximated from the equation of Meinkoth and Wahl (Anal. Biochem. 138: 267-84 (1984)):

$$T_m = 81.5° C. + 16.6(\log M) + 0.41(\% GC) - 0.61(\% \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of SEQ ID SEQ ID NO:2, 3, 4, or 10.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution), it may be preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C. However, because specificity is typically a function of post-hybridization washes, where the factors controlling hybridization include the ionic strength and temperature of the final wash solution, the high stringency conditions can more simply be expressed as including a wash in 0.1×SSC at 60 to 65° C.

The following terms are used to describe the sequence relationships between two or more nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of SEQ ID SEQ ID NO:2, 3, 4, or 10) or an amino acid sequence (e.g., any of SEQ ID NO:1, 5, 6, 7, 8, 9, 11, 12, 13, 14, or 15). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 10 amino acids, and can optionally be 15, 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

For example, sequence identity/similarity values provided herein can refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU ($C_1$-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, with at least 55% sequence identity, or at least 60%, or at least 70%, or at least 80%, or at least 90% or at least 95% sequence identity, or at least 96%, or at least 97%, or at least 98%, or at least 99%, or any percentage value within the range of 55-100% sequence identity relative to the reference sequence over a specified comparison window. Optimal alignment may be ascertained or conducted using the homology alignment algorithm of Needleman and Wunsch, supra.

One indication that two CSLF6-related polypeptide sequences are substantially identical is that both polypeptides have glucan synthase activity with glucose as a substrate.

The polypeptide that is substantially identical to a CSLF6 and/or IRE1 with a SEQ ID NO:1, 5, 6, 7, 8, 9, 11, 12, 13, 14, or 15 sequence may not have exactly the same level of activity as the CSLF6 and/or IRE1 with a SEQ ID NO:1, 5, 6, 7, 8, 9, 11, 12, 13, 14, or 15. Instead, the substantially identical polypeptide may exhibit greater or lesser levels of activity than the CSLF6 and/or IRE1 with SEQ ID NO:1, 5, 6, 7, 8, 9, 11, 12, 13, 14, or 15, as measured by assays available in the art or described herein (e.g., glucan synthase activity and/or protein folding activity). For example, the substantially identical polypeptide can have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the CSLF6 and/or IRE1 with the SEQ ID NO:1, 5, 6, 7, 8, 9, 11, 12, 13, 14, or 15 sequence when measured by similar assay procedures.

Alternatively, substantial identity is present when second polypeptide is immunologically reactive with antibodies raised against the first polypeptide (e.g., a polypeptide with SEQ ID NO:1, 5, 6, 7, 8, 9, 11, 12, 13, 14, or 15). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The CSLF6 and/or IRE1 polypeptides can include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a the SEQ ID NO:1, 5, 6, 7, 8, 9, 11, 12, 13, 14, or 15 sequence. Alternatively, the CSLF6 and/or IRE1 polypeptides may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of the SEQ ID NO:1, 5, 6, 7, 8, 9, 11, 12, 13, 14, or 15 sequence.

Plants Modified to Express or Contain CSLF6 and/or IRE1

To engineer healthy plants with increased levels of glucans and good growth, one of skill in the art can introduce CSLF6 and/or IRE1, or nucleic acids encoding such CSLF6 and/or IRE1 polypeptides into the plants. Introduction of CSLF6 and/or IRE1, or expression of increased levels of CSLF6 and/or IRE1, in a plant can increase the plant's biomass or glucan levels by 5% or more. For example, introduction of CSLF6 and/or IRE1, or expression of increased levels of CSLF6 and/or IRE1, in a plant can increase the plant's biomass or glucan content by at least 10%, or at least 15%, or at least 20%, or at least 25%, or at least 30%, or at least 33% compared to a wild type plant of the same species that does not comprise the CSLF6 expression cassette and/or the IRE1 expression cassette.

For example, one of skill in the art can inject CSLF6 and/or IRE1 polypeptides into young plants.

Alternatively, one of skill in the art can generate genetically-modified plants that contain nucleic acids encoding CSLF6 and/or IRE1 within their somatic and/or germ cells. Such genetic modification can be accomplished by various procedures. For example, one of skill in the art can prepare an expression cassette or expression vector that can express one or more encoded CSLF6 and/or IRE1 polypeptides. Plant cells can be transformed by the expression cassette or expression vector, and whole plants (and their seeds) can be generated from the plant cells that were successfully transformed with the CSLF6 and/or IRE1 nucleic acids. Some procedures for making such genetically modified plants and their seeds are described below.

Promoters: The CSLF6 and/or IRE1 nucleic acids described herein can be operably linked to a promoter, which provides for expression of mRNA from the CSLF6 and/or IRE1 nucleic acids. The promoter is typically a promoter functional in plants and/or seeds and can be a promoter functional during plant growth and development. A CSLF6 and/or IRE1 nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that allows gene expression to be turned on and off in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but are not limited to, a plant promoter such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.*

84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kDa zein protein, a Z27 promoter from a gene encoding a 27 kDa zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985).

Another promoter useful for expression of CSLF6 and/or IRE1 is the *Brachypodium distachyon* PIN-like (e.g., PIN-4) promoter, which can have the sequence shown below (SEQ ID NO:16).

```
   1  GATTTGAGCA TGTTCTTGAT GAGGTCCTTG
      GCGCTGGGGG
  41  AGATGTTGGG CCACGGGTCG GAGTCGAAGT
      CTATGGCGCC
  81  TTTTAGGACC GCGTCGAAGA TCCCCTGCTG
      CGTCTCGGCC
 121  CAGAAGGGCG GGACGCCGGA GAGCAGGATG
      TAGACGATGA
 161  CCCCCGCCGT CCAGACGTCG GCTTCGGGCC
      CGTAGTGCTT
 201  GCAGAGGACC TCGGGGCCA CGTAGTACGG
      GCTTCCGACG
 241  ACGTCGGTGA AGATCTGGCC GGGCTTGAAG
      AAGACGGAGA
 281  GTCCGAAATC GATGGCCTTG AGATCGGCGA
      CCGAGTCGTC
 321  TTCGTCTTCT CCGTTGCCGG CGCCGGCGCC
      GCCGAGCAAG
 361  AGGAAGTTCT CGGGCTTGAG GTCGCGGTGC
      ATGACCCCCA
 401  GAGAATGGCA CGCCTCGACG ACGCCGACGA
      CGACGCGTGC
 441  GATCTCGGCG GCTTTCCGCT CGGAGAAGTA
      TCCGCGGGCG
 481  ACGATGCGGT CGAAGAGCTC GCCGCCCTCG
      CAGAGGTCCA
 521  TGACGATGTG GACGTAGAGC GGGTCCTCGT
      AGGCGCCGCG
 561  GATGGTGACG ACGCTGGCGT GGCCCGCCAG
      GTGGTGCATG
 601  ATCTGGATCT CGCGGCGGAC GTCGTCCACG
      TCCTCGGGGG
 641  TGAGGAGCTT GCGCTTGGCG ATGGACTTGC
      AGGCGAGGGG
 681  TGTCCCCGTG GCGATGTCGG TGCAGAGGTA
      GGTGGTGCCG
 721  AACTGGCCCT GGCCGAGCTT GCGGCCGAGC
      GTGTAGAGGG
 761  AGGTGAGCGG CGGGGTGTCG TGGCCGAGGA
      CGGCGGTCGG
 801  GGAGGAGAGG TGGTGCTGGT GGCCGCGCAT
      GGTGTTGGTG
 841  GTGCAGGGGG CTTGGAGGTG GAGATGGAAG
      GGGTCCGAGT
 881  CGGCGGTGCT GCTGTTGGAA TCGCGGCACG
      AGTAGTTGCC
 921  CATGCGCACC GCGTCAATTG TCGCCGGCGG
      CCATGGCGAC
 961  CACCGTGGAT GGATGATTGG ACCACAGAGA
      AATTAGGGGG
1001  TGGAGAGGAA GAGGAGAGCT GTGCTCCATT
      AGTTTGGGAG
1041  GAAGAGGAGA CCAAATTGGC AATGGCCTGC
      ATGTCGTGCG
1081  CTGCACCTAC CTAAGCTAGC GTGCATGTCG
      ATTTGCTCCT
1121  GCGACACCAC GATTCGGCCC TTTTTCGGCC
      TAAATGAAAC
1161  ATCGTCCATC TCGAATCAAC CTAGCCACAT
      CATTCTTTTT
1201  CTTTTTGCAA GATCGATCCC TGTGCAGTAG
      ACATGCATGC
```

-continued

| | |
|---|---|
| 1241 | TGGAGTAGCA GTAGGAATCA GGGACTGGCC AGCCTGGCCT |
| 1281 | TGCTAGTGAG CGAGTGTACG TGCAATGCCA ATTAACCGTT |
| 1321 | TGCTTATTTT ACTAGTACCA TCATATCGAT CGATCTCAAT |
| 1361 | CAAGCTGCTG ACGTAGGGCA ACATATATAA GATCGTTTTC |
| 1401 | AGCTCGTGGT GCACGATGCG CAATAATACC GATCCTGTTA |
| 1441 | GTTGAGTTCA ATCAATTAAG AGCTCTGTTT CCTCATCTCT |
| 1481 | CACCTACGAG AAGCGGCGCA TACAGAAATA GAAGATGTTG |
| 1521 | AGGTAGATCA AGTTCATATT GATGTTAACT TGAATACTTA |
| 1561 | TTGAAGATTT CAATTCAAAG GACACTAGAA GAATGATGCT |
| 1601 | GTTCAAATAA AGATGTTGAG GTAGAGGAAG TTCATTATTC |
| 1641 | TAGTACTTTT CTAGTGAGGG AGATTTTCGC ACCTGCATGT |
| 1681 | ATTTATTGCT GTCAAATATA TGACGCCAAT GAAATAGAAA |
| 1721 | AATACTCTTA ATTAATAATA TGCGATAATA AATTATTTTA |
| 1761 | CCCCGGCCGG TGGTTTATTT TTCTTGCTTC GCGCCCCTGC |
| 1801 | CTAGCGAGGA GAGGTGCATG CGATCCACCG GCCCATGGAT |
| 1841 | CGTCGCTTAA TTAGTACCGG TAATTTCCTT ATTAAACCAG |
| 1881 | GAATGCAAAT AATTCATGTC CTGGACAGTG AGATGATGAG |
| 1921 | CAGGTCGGCG GGTATGCGCG CGAACGTACG GTCTCTGTCG |
| 1941 | ATCGTGTGCC ACGTGCATTA GCGGAGCCGA CGGCCTGCTC |
| 1961 | GCAGAGCCCG GACAAATTCC CTAAAAATTA ATTATACAAG |
| 2001 | AAAAACACTA CTCTGGTGGC TAATTAACAC GCTGGCTAGC |
| 2041 | GGCATCATGG CTTCCCCAGT GATCGATAGC ACTGGGGAAG |
| 2081 | CATGCATAGC TCGATGGAAT CACTCCATGC GAGTGCATAT |
| 2121 | GTCGCACCAA CCAAATTTCT TTCGTCACTT AGTATGAAAC |
| 2161 | GGAGAGAATG TATGATCGAC CGATTCTGAT CCCGCATGAT |
| 2201 | AATAGTGAGA TCGATTCTGG TCCCGCATGA TAATAATGAG |
| 2241 | ATCTCAACAA ATTAACCAAC AAACATACAA TTGCACATGC |
| 2281 | CTGCCTATAC TACTTATCAC CGTCCAAATT AAAGCATTCA |
| 2321 | TGCCACCCTA GCTAAAAATA GATACATCCA TATTTAAACA |
| 2361 | AATTTGAATT AAGAATTTAG AAACGGGAGC AGGCAGGAAC |
| 2401 | AATCCAGCGG CTTCTTATTG ACTCTGTCAA CACAACACTA |
| 2441 | GCTAGCTGGG TTTTCAGACT TCATTAACAG CGCACGCTAG |
| 2481 | CGGCATCATG GCTTCCCAAG TGAGCGGTCG AGCGCCGACA |
| 2521 | AAAACGGGAC CCCGGCCCTC TGTGTGATTT GATGCGAGTT |
| 2561 | GCTAGCAGTG TGTCTGACAC TGTGATGTTT GGTCCAGGTA |
| 2601 | TGAACCAACC AAGATCACAG GAAAAAAAAC AATCGCACAT |
| 2641 | GCATGTATGA ATCTCCTCCG GCCTATATAT ACTCGCCACC |
| 2681 | ATCTCGGAAT TAAAGCATGC ATGCCACTTA CAGCAGGCTT |
| 2721 | GCATCACCAG CTGCCACTCA GCTGGGTTTT CATCAGTCTT |

```
2761    AAACTGAGCT GTGTTAATTA CCTGAGCACA
        CACACAGCTC

2801    AAGTCTGAAC AAGCTAGTAA G
```

Alternatively, novel tissue specific promoter sequences may be employed in the practice of the present invention. cDNA clones from a particular tissue can be isolated and those clones which are expressed specifically in that tissue are identified, for example, using Northern blotting. Preferably, the gene isolated is not present in a high copy number but is relatively abundant in specific tissues. The promoter and control elements of corresponding genomic clones can then be localized using techniques well known to those of skill in the art.

A CSLF6 and/or IRE1 nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The CSLF6 and/or IRE1 nucleic acids can be subcloned downstream from the promoter using restriction enzymes and positioned to ensure that the DNA is inserted in proper orientation with respect to the promoter so that the DNA can be expressed as sense RNA. Once the CSLF6 and/or IRE1 nucleic acid is operably linked to a promoter, the expression cassette so formed can be subcloned into a plasmid or other vector (e.g., an expression vector).

In some embodiments, a cDNA clone encoding a CSLF6 and/or IRE1 protein is isolated from plant tissue, for example, a root, stem, leaf, seed, or flower tissue. For example, cDNA clones from selected species (that encode a CSLF6 and/or IRE1 protein with homology to any of those described herein) are made from isolated mRNA from selected plant tissues. In another example, a nucleic acid encoding a mutant or modified CSLF6 and/or IRE1 protein can be prepared by available methods or as described herein. For example, the nucleic acid encoding a mutant or modified CSLF6 and/or IRE1 protein can be any nucleic acid with a coding region that hybridizes to a segment of a SEQ ID SEQ ID NO:2, 3, 4, or 10 nucleic acid. Such a nucleic acid can encode an enzyme with glucan synthase activity and/or protein folding activity. Using restriction endonucleases, the entire coding sequence for the modified CSLF6 and/or IRE1 is subcloned downstream of the promoter in a 5' to 3' sense orientation.

Targeting Sequences: Additionally, expression cassettes can be constructed and employed to target the CSLF6 and/or IRE1 proteins to an intracellular compartment within plant cells, into a membrane, or to direct an encoded protein to the extracellular environment. This can generally be achieved by joining a DNA sequence encoding a transit or signal peptide sequence to the coding sequence of the CSLF6 and/or IRE1 nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences: When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research*. 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology*. 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the CSLF6 and/or IRE1 nucleic acids by standard methods.

Selectable and Screenable Marker Sequences: To improve identification of transformants, a selectable or screenable marker gene can be employed with the expressible CSLF6 and/or IRE1 nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, e.g., by use of a selective agent (e.g., an herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Numerous other possible selectable and/or screenable marker genes will be apparent to those of skill in the art in addition to those forth herein below. Therefore, it will be understood that the discussion herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0218571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the Cl and R alleles are introduced together.

The R gene regulatory regions may be employed in chimeric constructs to provide mechanisms for controlling the expression of chimeric genes. More diversity of phenotypic expression is known at the R locus than at any other locus (Coe et al., in *Corn and Corn Improvement,* eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells but is preferably used to transform dicot plant cells.

In Vitro Screening of Expression Cassettes: Once the expression cassette is constructed and subcloned into a suitable plasmid, it can be screened for the ability to substantially inhibit the translation of an mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay that measures the inhibition of translation of an mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

DNA Delivery of the DNA Molecules into Host Cells: The present invention generally includes steps directed to introducing CSLF6 and/or IRE1 nucleic acids, such as a preselected cDNA encoding the CSLF6 and/or IRE1 enzyme, into a recipient cell to create a transformed cell. In some instances, the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant with glucan synthase activity, normal to improved growth, and/or protein folding, wherein the plant has an introduced CSLF6 and/or IRE1 nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include grasses, softwoods, hardwoods, wheat, rice, maize, barley, rye, *Brachypodium, Arabidopsis*, alfalfa, oats, sorghum, millet, *miscanthus*, switchgrass, poplar, *eucalyptus*, sugarcane, bamboo, tobacco, cucumber, tomato, soybean, and the like. In some embodiments, the plant or cell is a monocotyledon plant or cell. For example, the plant or cell can be a grass plant or cell. In some embodiments, the plant or cell is a dicotyledon plant or cell. For example, the plant or cell can be a hardwood plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0604662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Similar tissues can be transformed for softwood or hardwood species. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the CSLF6 and/or IRE1 nucleic acids for an effective period of time. This may range from a less than one second pulse of electricity for electroporation to a 2-3 days co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

The microprojectile bombardment is an effective means of reproducibly stably transforming monocots that avoids the need to prepare and isolate protoplasts (Christou et al., *PNAS.* 84:3962-3966 (1987)), avoids the formation of partially degraded cells, and the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Using techniques set forth herein, one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize: After effecting delivery of a CSLF6 and/or IRE1 nucleic acid to recipient cells by any of the methods discussed above, the transformed cells can be identified for further culturing and plant regeneration. As mentioned above, to improve the ability to identify transformants, one may desire to employ a selectable or screenable marker gene as, or in addition to, the expressible CSLF6 and/or IRE1 nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the Cl and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those providing 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of interest if the traits are to be commercially useful.

Regenerated plants can be repeatedly crossed to inbred plants to introgress the CSLF6 and/or IRE1 nucleic acids into the genome of the inbred plants. This process is referred to as backcross conversion. When a sufficient number of crosses to the recurrent inbred parent have been completed to produce a product of the backcross conversion process that is substantially isogenic with the recurrent inbred parent except for the presence of the introduced CSLF6 and/or IRE1 nucleic acids, the plant is self-pollinated at least once to produce a homozygous backcross converted inbred containing the CSLF6 and/or IRE1 nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the CSLF6 and/or IRE1 nucleic acids (or CSLF6 and/or IRE1 proteins). Transgenic plant and/or seed tissue can be analyzed for CSLF6 and/or IRE1 expression using standard methods such as SDS polyacrylamide gel electrophoresis, liquid chromatography (e.g., HPLC) or other means of detecting a product of CSLF6 and/or IRE1 activity (e.g., increased glucan content and/or good growth).

Once a transgenic seed expressing the CSLF6 and/or IRE1 sequence and having an increase in glucan content in the plant is identified, the seed can be used to develop true breeding plants. The true breeding plants are used to develop a line of plants with an increase in the percent of glucan content and growth of the plant while still maintaining other desirable functional agronomic traits. Adding the trait of increased glucan content and growth and normal to improved growth of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of glucan synthase activity, normal to improved growth, and/or protein folding in the plant. The resulting progeny are then crossed back to the parent that expresses the increased CSLF6 and/or IRE1 trait (more glucans, normal to improved growth, and/or protein folding). The progeny from this cross will also segregate so that some of the progeny carry the trait and some do not. This back-crossing is repeated until an inbred line with the desirable functional agronomic traits, and with expression of the trait involving an increase in glucan content and normal to improved growth of the plant. Such expression of the increased glucan content and/or normal to improved growth of plant can be expressed in a dominant fashion.

Subsequent to back-crossing, the new transgenic plants can be evaluated for an increase in the weight percent of glucan synthase activity, normal to improved growth, and/or protein folding of the plant. This can be done, for example, by immunofluorescence analysis of whole plant cell walls (e.g., by microscopy), glucan synthase activity assays, protein folding assays, growth measurements, and any of the assays described herein or available to those of skill in the art.

The new transgenic plants can also be evaluated for a battery of functional agronomic characteristics such as lodging, kernel hardness, yield, resistance to disease, resistance to insect pests, drought resistance, and/or herbicide resistance.

As described herein, expression of IRE1 and/or CSLF6 can not only increase the glucan content of plant tissues but such expression can also increase the growth or height of plants. Hence it is useful to modify a variety of plant types to express IRE1 and/or CSLF6.

Plants that can be improved include but are not limited to forage plants (e.g., alfalfa, clover, soybeans, turnips, bromegrass, bluestem, and fescue), starch plants (e.g., canola, potatoes, lupins, sunflower and cottonseed), grains (maize, wheat, barley, oats, rice, sorghum, millet and rye), grasses (switchgrass, prairie grass, wheat grass, sudangrass, sorghum, straw-producing plants, *miscanthus*, switchgrass), sugar producing plants (sugarcane, beets), vegetable plants (e.g., cucumber, tomato), *Brachypodium, Arabidopsis*, bamboo, softwood, hardwood and other woody plants (e.g., those used for paper production such as poplar species, pine species, and *eucalyptus*). In some embodiments the plant is a forage crop species, a species useful for production of biofuels, or a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, *Brachypodium*, grasses (e.g., *miscanthus*, switchgrass, and the like), as well as trees such as poplar, aspen, willow, and the like. Plants useful for generating dairy forage include legumes such as alfalfa, as well as clover, soybeans, turnips, *Brachypodium, Arabidopsis*, and forage grasses such as bromegrass, and bluestem.

Determination of Stably Transformed Plant Tissues: To confirm the presence of the CSLF6 and/or IRE1 nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced CSLF6 and/or IRE1 nucleic acids. PCR also be used to reverse transcribe RNA into DNA, using enzymes such as reverse transcriptase, and then this DNA can be amplified by use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the CSLF6 and/or IRE1 nucleic acid in question, they do not provide information as to whether the preselected DNA segment is being expressed. Expression may be evaluated by specifically identifying the protein products of the introduced CSLF6 and/or IRE1 nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the CSLF6 and/or IRE1 such as evaluation by amino acid sequencing following purification. The Examples of this application also provide assay procedures for detecting and quantifying CSLF6 and/or IRE1 activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Release of Fermentable Sugars from Plant Biomass

Plant parts, components and biomass from plants expressing CSLF6 and/or IRE1 can be converted into fermentable sugars using various procedures. For example, the plant parts, components and biomass from plants expressing CSLF6 and/or IRE1 can be dried and/or ground up so that the polysaccharides become accessible to enzymatic cleavage.

Effective enzyme mixtures for biomass deconstruction can have combined catalytic activities so that the enzymes can cleave substantially all saccharide linkages found in plant cell walls to release free, fermentable sugar residues. Such enzyme mixtures can often be derived from microorganisms. Many microorganisms that live in lignocellulose-rich environments secrete large numbers and broad ranges of cell wall-active enzymes, including, but not limited to, cellulases, hemicellulases, pectinases, and/or proteases. Most commercially available deconstruction enzyme mixtures contain between approximately twenty-five to one hundred and fifty (25-150) enzymes. Nagendran et al., *Fung. Genet. Biol.* 46: 427-435 (2009); Banerjee et al., *Bioresour. Technol.* 101: 9097-9105 (2010); and Scott-Craig et al., *J Biol Chem* 286:42848-42854 (2011). For example, commercial enzyme mixtures can be used that include hemicellulose degrading enzymes such as β-1,4-xylanase, β-xylosidase, α-arabinosidase, mixed-linked glucanase, α-glucuronidase, etc. Examples of commercial enzyme mixtures that can be employed to release fermentable sugars from plant biomass include Spezyme CP, Accellerase®1000, Multifect Xylanase, Celtic® CTec2, HTec2, CTec3, HTec3, and AlternaFuel® CMAX.

Incubation of the plant biomass with the enzyme mixture can be performed at a temperature ranging from approximately 40° to approximately 60° C. In one embodiment, the incubation is performed at a pH ranging from approximately 4 to approximately 6.

DEFINITIONS

As used herein, the term "plant" is used in its broadest sense. It includes, but is not limited to, any species of grass (e.g. forage, grain-producing, turf grass species), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

The term "transgenic" when used in reference to a plant or leaf or fruit or seed or plant biomass, for example a "transgenic plant," transgenic leaf," "transgenic fruit," "transgenic fruit," "transgenic seed," "transgenic biomass," or a "transgenic host cell" refers to a plant or leaf or fruit or seed or biomass that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "transgene" refers to a foreign gene that is placed into an organism (e.g. a plant) or host cell by the process of transfection. The term "foreign gene" or heterologous gene refers to any nucleic acid (e.g., gene sequence) that is introduced into the genome of an organism or tissue of an organism or a host cell by experimental manipulations, such as those described herein, and may include gene sequences found in that organism so long as the introduced gene does not reside in the same location, as does the naturally occurring gene.

As used herein, a "native" nucleic acid or polypeptide means a DNA, RNA or amino acid sequence or segment that has not been manipulated in vitro, i.e., has not been isolated, purified, and/or amplified.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene. As used herein, the term "wild-type" when made in reference to a plant refers to the plant type common throughout an outbred population that has not been genetically manipulated to contain an expression cassette, e.g., any of the expression cassettes described herein.

The following non-limiting Examples illustrate how aspects of the invention have been developed and can be made and used.

Example 1: Materials and Methods

This Example describes some of the materials and methods used in developing the invention.

Cloning and Plant Transformation

The coding sequence of CSLF6 from *Brachypodium distachyon* was amplified by PCR using *Brachypodium distachyon* synthesized CSLF6 as template, to provide the following nucleotide sequence that encodes the CSLF6 protein (SEQ ID NO:2).

```
  1    ATGGCGCCAG CGGTGGCCGG CGGGAGCAGC
       CGGGGTGCAG
 41    GGTGTAAGTG CGGGTTCCAG GTGTGCGTGT
       GCTCTGGGTC
 81    GGCGGCGGTG GCGTCGGCGG GTTCGTCGCT
       GGAGGTGGAG
```

-continued

| | |
|---|---|
| 121 | AGAGCCATGG CGGTGACGCC GGTGGAAGGG CAGGCGGCGC |
| 161 | CGGTGGACGG CGAGAGCTGG GTCGGCGTCG AGCTCGGCCC |
| 201 | CGACGGCGTG GAGACGGACG AGAGCGGCGC CGGCGTCGAC |
| 241 | GACCGCCCCG TCTTCAAGAC CGAGAAGATC AAGGGCGTCC |
| 281 | TCCTCCACCC CTACAGGGTG CTGATCTTTG TTCGTCTGAT |
| 321 | AGCGTTCACC CTGTTCGTGA TCTGGCGTAT CTCGCACAAG |
| 361 | AACCCGGACA CGATGTGGCT GTGGGTGACC TCCATCTGCG |
| 401 | GCGAGTTCTG GTTCGGCTTC TCCTGGCTGC TGGACCAGCT |
| 441 | TCCAAAGCTC AACCCGATCA ACCGGATCCC GGACCTCGCC |
| 481 | GTGCTCCGGC AACGCTTCGA CCGCGCCGAC GGGACATCCA |
| 521 | CATTGCCGGG CCTCGACATC TTCGTCACCA CGGCCGACCC |
| 561 | CATCAAGGAA CCCATCCTGT CGACGGCCAA CTCCGTGCTC |
| 601 | TCCATCCTGG CCGCCGACTA CCCGGTGGAC CGCAACACCT |
| 641 | GCTACATCTC CGACGACAGC GGCATGCTCA TGACCTACGA |
| 681 | GGCCATGGCG GAGTCGGCCA AGTTCGCCAC CCTCTGGGTG |
| 721 | CCATTCTGCC GCAAGCACGG CATCGAACCA CGCGGGCCGG |
| 761 | AGAGCTACTT CGAGCTCAAG TCGCACCCGT ACATGGGGAG |
| 801 | AGCGCACGAC GAGTTCGTCA ATGACCGCCG CCGGGTGCGC |
| 841 | AAGGAGTATG ATGACTTCAA GGCCAAGATT AACTCTCTGG |
| 881 | AGACTGATAT CCAGCAGAGG AATGATCTGC ATAACGCTGC |
| 921 | CGTGCCGCAG AATGGGGATG GGATCCCCAG GCCTACCTGG |
| 961 | ATGGCTGATG GAGTCCAGTG GCAGGGGACT TGGGTCGAGC |
| 1001 | CGTCCGCTAA TCACCGCAAG GGAGACCACG CCGGCATCGT |
| 1041 | CCTGGTTCTG ATTGACCACC CGAGCCACGA CCGCCTTCCC |
| 1081 | GGCGCGCCGG CGAGCGCCGA CAACGCGCTG GACTTCAGCG |
| 1121 | GCGTGGACAC CCGCCTCCCG ATGCTCGTCT ACATGTCCCG |
| 1161 | CGAGAAGCGC CCAGGCCACA ACCACCAGAA GAAGGCCGGC |
| 1201 | GCCATGAACG CGCTCACCAG GGCTTCCGCG CTGCTCTCCA |
| 1241 | ACGCGCCCTT CATCCTCAAC CTCGACTGCG ACCACTACAT |
| 1281 | CAACAACTCC CAGGCCCTCC GCGCCGGGAT CTGCTTCATG |
| 1321 | GTCGGCCGGG ACAGCGACAC CGTCGCCTTC GTGCAGTTCC |
| 1361 | CGCAGCGGTT CGAGGGCGTC GACCCCACGG ACCTCTACGC |
| 1401 | CAACCACAAC CGCATCTTCT TCGACGGCAC CCTCAGGGCG |
| 1441 | CTCGACGGAA TGCAAGGCCC GATCTATGTC GGCACGGGAT |
| 1481 | GCCTCTTCCG GCGCATCACC GTCTACGGCT TCGACCCGCC |
| 1521 | CAGGATCAAC GTCGGCGGGC ATGCTTCCC TGCTCTCGGT |
| 1561 | GGCCTGTTCG CCAAGACCAA GTATGAGAAG CCCAGCATGG |
| 1601 | AGATGACCAT GGCGAGAGCC AACCAGGCCG TGGTGCCGGC |
| 1641 | CATGGCCAAG GGGAAGCACG GCTTCCTGCC GCTCCCCAAG |
| 1681 | AAGACGTACG GGAAGTCCGA CAAGTTCGTG GACACCATCC |

```
1721  CGCGCGCGTC CCACCCGTCG CCGTACGCGG
      CGGAGGGGAT
1761  CCGCGTGGTG GACTCCGGCG CGGAGACTCT
      GGCTGAGGCC
1801  GTCAAGGTGA CCGGATCGGC ATTCGAGCAG
      AAGACCGGAT
1841  GGGGCAGCGA GCTCGGCTGG GTCTACGACA
      CTGTCACAGA
1881  GGACGTGGTG ACTGGCTACA GGATGCACAT
      CAAGGGCTGG
1921  AGGTCCCGCT ACTGCTCCAT CTACCCGCAC
      GCCTTCATCG
1961  GCACCGCCCC GATCAACCTC ACGGAGCGGC
      TCTTCCAGGT
2001  GCTCCGCTGG TCCACCGGCT CCCTCGAGAT
      CTTCTTCTCC
2041  AAGAACAACC CGCTCTTCGG CAGCACCTAC
      CTGCACCCGC
2081  TCCAGCGCGT CGCCTACATC AACATCACCA
      CATACCCGTT
2121  CACCGCCATC TTCCTCATCT TCTACACCAC
      CGTGCCGGCG
2161  CTCTCCTTCG TCACCGGCCA CTTCATCGTG
      CAGCGCCCGA
2201  CGACCATGTT CTACGTCTAC CTGGGGATCG
      TGCTGGCGAC
2241  GCTGCTCATC ATCGCTGTTC TTGAGGTCAA
      GTGGGCTGGA
2281  GTGACAGTGT TCGAGTGGTT CAGGAACGGG
      CAGTTCTGGA
2321  TGACGGCTAG CTGCTCCGCC TACCTTGCTG
      CTGTGTGCCA
2361  GGTGCTCACC AAGGTGATCT TCAGGAGGGA
      CATCTCATTC
2401  AAGCTCACTT CCAAGCTGCC TGCTGGGGAC
      GAGAAGAAGG
2441  ACCCCTATGC CGATCTGTAC GTGGTGCGTT
      GGACTCCACT
2481  CATGATCACT CCAATCATCA TCATCTTCGT
      CAACATCATC
2521  GGCTCGGCGG TGGCCTTCGC CAAGGTGCTG
      GACGGCGAGT
2561  GGACGCACTG GCTCAAGGTG GCGGGAGGAG
      TCTTCTTCAA
2601  CTTCTGGGTG CTGTTCCACC TCTACCCGTT
      CGCCAAGGGT
2641  CTCCTGGGGA AGCATGGCAA GACCCCCGTC
      GTCGTGCTCG
2681  TCTGGTGGGC ATTCACCTTC GTCATCACCG
      CCGTCCTCTA
2721  CATCAACATC CCGCACATCC ATGGAGGAGG
      AGGCAAGCAC
2761  AGCGTGGGGC ATGGGATGCA CCATGGCAAG
      AAGTTCGACG
2801  GCTACTACCT CTGGCCGTGA
```

A nucleotide sequence that encodes the CSLF6 protein from *Brachypodium distachyon* with SEQ ID NO:1 and that has been codon-optimized for expression in *Brachypodium distachyon* was made and is shown below as SEQ ID NO:3.

```
   1  ATGGCTCCAG CTGTTGCTGG CGGCTCCTCT AGGGGCGCTG
  41  GCTGCAAGTG CGGCTTCCAG GTGTGCGTGT GCTCCGGCTC
  81  TGCCGCCGTG GCCTCCGCCG GCTCATCCCT CGAGGTCGAG
 121  AGGGCCATGG CTGTTACCCC AGTTGAGGGC CAGGCCGCTC
 161  CAGTGGACGG CGAGTCCTGG GTGGGCGTTG AGCTTGGCCC
 201  AGACGGCGTC GAGACCGACG AGTCCGGCGC TGGCGTGGAC
 241  GACAGGCCAG TGTTCAAGAC CGAGAAGATC AAGGGCGTGC
 281  TCCTCCACCC ATACAGGGTG CTCATCTTCG TGAGGCTGAT
 321  CGCCTTCACC CTCTTCGTGA TCTGGCGCAT CTCCCACAAG
 361  AACCCGGACA CCATGTGGCT CTGGGTGACC TCTATTTGCG
 401  GCGAGTTCTG GTTCGGCTTC TCCTGGCTCC TCGACCAGCT
 441  CCCAAAGCTC AACCCGATCA ACCGCATCCC AGATCTCGCC
 481  GTTCTCAGGC AGAGGTTCGA TAGGGCCGAC GGCACCTCCA
 521  CCCTCCCAGG CCTTGATATT TTCGTGACCA CCGCCGACCC
 561  CATCAAGGAG CCAATTCTCT CAACCGCCAA CTCCGTGCTC
 601  TCTATCCTCG CCGCCGATTA CCCGGTGGAT AGGAACACGT
 641  GCTACATCTC CGACGACAGC GGCATGCTCA TGACCTACGA
 681  GGCTATGGCC GAGTCCGCCA AGTTCGCTAC CCTCTGGGTG
 721  CCATTCTGCC GCAAGCACGG CATCGAGCCA AGGGGCCCAG
 761  AGTCCTACTT CGAGCTTAAG TCCCACCCGT ACATGGGCAG
 801  GGCCCATGAC GAGTTCGTGA ACGATAGGCG CAGGGTGAGG
 841  AAGGAGTACG ACGACTTCAA GGCCAAGATC AACTCCCTCG
```

-continued

```
 881 AGACGGACAT CCAGCAGAGG AACGACCTCC ATAACGCCGC
 921 CGTGCCACAG AACGGGACG GCATCCCAAG GCCAACCTGG
 961 ATGGCCGATG GCGTGCAGTG GCAGGGCACC TGGGTTGAGC
1001 CATCTGCCAA CCATAGGAAG GGCGATCACG CCGGCATTGT
1041 GCTCGTGCTC ATCGACCATC CATCCCACGA CAGGCTCCCA
1081 GGCGCCCCAG CCTCTGCCGA CAACGCCCTC GACTTCTCCG
1121 GCGTGGACAC CAGGCTTCCA ATGCTCGTTT ACATGTCCCG
1161 CGAGAAGAGG CCAGGCCACA ACCACCAGAA GAAGGCTGGC
1201 GCTATGAACG CCCTTACCAG GGCTTCTGCT CTCCTCTCCA
1241 ACGCCCCGTT CATCCTCAAC CTCGACTGCG ACCACTACAT
1281 CAACAACAGC CAGGCTCTCA GGGCCGGCAT CTGCTTCATG
1321 GTGGGCAGGG ATTCTGACAC CGTGGCCTTC GTTCAGTTCC
1361 CGCAGCGCTT CGAGGGGGTT GACCCAACCG ATCTCTACGC
1401 CAACCACAAC AGGATTTTCT TCGATGGCAC CCTCAGGGCC
1441 CTCGATGGCA TGCAGGGCCC TATCTACGTG GGCACCGGCT
1481 GCCTCTTCAG GCGCATCACC GTGTACGGCT TCGACCCGCC
1521 AAGGATTAAC GTTGGCGGCC CATGCTTCCC AGCTCTCGGC
1561 GGCCTCTTCG CTAAGACCAA GTACGAGAAG CCCAGCATGG
1601 AGATGACCAT GGCCAGGGCC AACCAGGCCC TTGTTCCAGC
1641 TATGGCTAAG GGGAAGCACG GCTTCCTGCC ACTCCCGAAG
1681 AAGACCTACG GCAAGAGCGA CAAGTTCGTC GACACCATTC
1721 CAAGGGCCTC CCACCCATCT CCATACGCTG CCGAGGGCAT
1761 TAGGGTTGTG GACTCTGGCG CCGAGACCCT CGCCGAGGCC
1801 GTGAAGGTGA CCGGCTCCGC CTTCGAGCAG AAGACCGGCT
1841 GGGGCTCCGA GCTTGGCTGG GTTTACGACA CCGTGACCGA
1881 GGATGTGGTC ACCGGCTACA GGATGCACAT TAAGGGCTGG
1921 CGCAGCAGGT ACTGCTCCAT CTACCCACAT GCCTTCATCG
1961 GCACCGCCCC CATTAACCTC ACCGAGAGGC TTTTCCAGGT
2001 GCTCAGGTGG TCTACCGGCA GCCTCGAGAT CTTCTTCAGC
2041 AAGAACAACC CGCTGTTCGG CTCCACCTAC CTGCATCCAC
2081 TCCAGAGGGT GGCCTACATT AACATCACCA CCTACCCGTT
2121 CACCGCCATC TTCCTCATCT TCTACACGAC CGTGCCCGCC
2161 CTCTCATTCG TGACCGGCCA TTTCATTGTG CAGAGGCCGA
2201 CCACCATGTT CTACGTGTAC CTCGGGATCG TGCTCGCCAC
2241 CCTCCTCATT ATTGCCGTGC TCGAGGTTAA GTGGGCTGGC
2281 GTGACCGTGT TCGAGTGGTT CCGCAACGGC CAGTTCTGGA
2321 TGACCGCCTC TTGCTCTGCT TACCTCGCCG CTGTTTGCCA
2361 GGTCCTCACC AAGGTTATCT TCCGCAGGGA CATCTCCTTC
2401 AAGCTCACCT CCAAGCTCCC AGCCGGCGAC GAGAAGAAGG
2441 ACCCATACGC CGATCTGTAC GTGGTGAGGT GGACCCCGCT
2481 CATGATCACC CCGATCATCA TCATTTTCGT CAACATCATC
2521 GGCTCCGCGG TCGCCTTCGC CAAGGTGCTC GATGGCGAGT
2561 GGACCCATTG GCTTAAGGTC GCCGGCGGCG TGTTCTTCAA
2601 CTTCTGGGTT CTCTTCCACC TCTACCCTTT CGCGAAGGGC
2641 CTTCTTGGCA AGCACGGCAA GACCCCAGTG GTGGTTCTTG
2681 TCTGGTGGGC CTTCACCTTC GTCATCACCG CCGTGCTGTA
2721 CATCAACATC CCGCACATCC ATGGCGGCGG CGGCAAGCAC
2761 TCCGTGGGCC ACGGCATGCA CCATGGCAAG AAGTTCGACG
2801 GCTACTACCT CTGGCCGTGA
```

A nucleotide sequence that encodes the CSLF6 protein from *Brachypodium distachyon* with an N-terminally fused yellow fluorescent protein (YFP) is shown below as SEQ ID NO:4.

```
   1 ATGGGCAAGG GCGAGGAGCT GTTCACCGGG GTGGTGCCCA
  41 TCCTGGTCGA GCTGGACGGC GACGTAAACG GCCACAAGTT
  81 CAGCGTGTCC GGCGAGGGCG AGGGCGATGC CACCTACGGC
 121 AAGCTGACCC TGAAGTTCAT CTGCACCACC GGCAAGCTGC
 161 CCGTGCCCTG GCCCACCCTC GTGACCACCT TCGGCTACGG
 201 CCTGCAGTGC TTCGCCCGCT ACCCCGACCA CATGAAGCAG
 241 CACGACTTCT TCAAGTCCGC CATGCCCGAA GGCTACGTCC
 281 AGGAGCGCAC CATCTTCTTC AAGGACGACG GCAACTACAA
 321 GACCCGCGCC GAGGTGAAGT TCGAGGGCGA CACCCTGGTG
 361 AACCGCATCG AGCTGAAGGG CATCGACTTC AAGGAGGACG
 401 GCAACATCCT GGGGCACAAG CTGGAGTACA ACTACAACAG
 441 CCACAACGTC TATATCATGG CCGACAAGCA GAAGAACGGC
 481 ATCAAGGTGA ACTTCAAGAT CCGCCACAAC ATCGAGGACG
 521 GCAGCGTGCA GCTCGCCGAC CACTACCAGC AGAACACCCC
 561 CATCGGCGAC GGCCCCGTGC TGCTGCCCGA CAACCACTAC
 601 CTGAGCTACC AGTCCGCCCT GAGCAAAGAC CCCAACGAGA
 641 AGCGCGATCA CATGGTCCTG CTGGAGTTCG TGACCGCCGC
 681 CGGGATCACT CTCGGCATGG ACGAGCTGTA CAAGTCCGGA
 721 CTCAGATCTC GAGCTCAAGC TTCGAATTCT GCAGTCGACG
 761 GTACCGCGGG CCCGGGATCA TCAACAAGTT TGTACAAAAA
 801 AGCAGGCTCC GAATTCGCCC TTATGGCTCC AGCTGTTGCT
 841 GGCGGCTCCT CTAGGGGCGC TGGCTGCAAG TGCGGCTTCC
 881 AGGTGTGCGT GTGCTCCGGC TCTGCCGCCG TGGCCTCCGC
 921 CGGCTCATCC CTCGAGGTCG AGAGGGCCAT GGCTGTTACC
 961 CCAGTTGAGG GCCAGGCCGC TCCAGTGGAC GGCGAGTCCT
1001 GGGTGGGCGT TGAGCTTGGC CCAGACGGCG TCGAGACCGA
1041 CGAGTCCGGC GCTGGCGTGG ACGACAGGCC AGTGTTCAAG
1081 ACCGAGAAGA TCAAGGGCGT GCTCCTCCAC CCATACAGGG
1121 TGCTCATCTT CGTGAGGCTG ATCGCCTTCA CCCTCTTCGT
```

-continued

```
1161 GATCTGGCGC ATCTCCCACA AGAACCCGGA CACCATGTGG
1201 CTCTGGGTGA CCTCTATTTG CGGCGAGTTC TGGTTCGGCT
1241 TCTCCTGGCT CCTCGACCAG CTCCCAAAGC TCAACCCGAT
1281 CAACCGCATC CCAGATCTCG CCGTTCTCAG GCAGAGGTTC
1321 GATAGGGCCG ACGGCACCTC CACCCTCCCA GGCCTTGATA
1361 TTTTCGTGAC CACCGCCGAC CCCATCAAGG AGCCAATTCT
1401 CTCAACCGCC AACTCCGTGC TCTCTATCCT CGCCGCCGAT
1441 TACCCGGTGG ATAGGAACAC GTGCTACATC TCCGACGACA
1481 GCGGCATGCT CATGACCTAC GAGGCTATGG CCGAGTCCGC
1521 CAAGTTCGCT ACCCTCTGGG TGCCATTCTG CCGCAAGCAC
1561 GGCATCGAGC CAAGGGGCCC AGAGTCCTAC TTCGAGCTTA
1601 AGTCCCACCC GTACATGGGC AGGGCCCATG ACGAGTTCGT
1641 GAACGATAGG CGCAGGGTGA GGAAGGAGTA CGACGACTTC
1681 AAGGCCAAGA TCAACTCCCT CGAGACGGAC ATCCAGCAGA
1721 GGAACGACCT CCATAACGCC GCCGTGCCAC AGAACGGGGA
1761 CGGCATCCCA AGGCCAACCT GGATGGCCGA TGGCGTGCAG
1801 TGGCAGGGCA CCTGGGTTGA GCCATCTGCC AACCATAGGA
1841 AGGGCGATCA CGCCGGCATT GTGCTCGTGC TCATCGACCA
1881 TCCATCCCAC GACAGGCTCC CAGGCGCCCC AGCCTCTGCC
1921 GACAACGCCC TCGACTTCTC CGGCGTGGAC ACCAGGCTTC
1961 CAATGCTCGT TTACATGTCC CGCGAGAAGA GGCCAGGCCA
2001 CAACCACCAG AAGAAGGCTG GCGCTATGAA CGCCCTTACC
2041 AGGGCTTCTG CTCTCCTCTC CAACGCCCCG TTCATCCTCA
2081 ACCTCGACTG CGACCACTAC ATCAACAACA GCCAGGCTCT
2121 CAGGGCCGGC ATCTGCTTCA TGGTGGGCAG GGATTCTGAC
2161 ACCGTGGCCT TCGTTCAGTT CCCGCAGCGC TTCGAGGGGG
2201 TTGACCCAAC CGATCTCTAC GCCAACCACA ACAGGATTTT
2241 CTTCGATGGC ACCCTCAGGG CCCTCGATGG CATGCAGGGC
2281 CCTATCTACG TGGGCACCGG CTGCCTCTTC AGGCGCATCA
2321 CCGTGTACGG CTTCGACCCG CCAAGGATTA ACGTTGGCGG
2361 CCCATGCTTC CCAGCTCTCG GCGGCCTCTT CGCTAAGACC
2401 AAGTACGAGA AGCCCAGCAT GGAGATGACC ATGGCCAGGG
2441 CCAACCAGGC CGTTGTTCCA GCTATGGCTA AGGGGAAGCA
2481 CGGCTTCCTG CCACTCCCGA AGAAGACCTA CGGCAAGAGC
2521 GACAAGTTCG TCGACACCAT TCCAAGGGCC TCCCACCCAT
2561 CTCCATACGC TGCCGAGGGC ATTAGGGTTG TGGACTCTGG
2601 CGCCGAGACC CTCGCCGAGG CCGTGAAGGT GACCGGCTCC
2641 GCCTTCGAGC AGAAGACCGG CTGGGGCTCC GAGCTTGGCT
2681 GGGTTTACGA CACCGTGACC GAGGATGTGG TCACCGGCTA
2721 CAGGATGCAC ATTAAGGGCT GGCGCAGCAG GTACTGCTCC
2761 ATCTACCCAC ATGCCTTCAT CGGCACCGCC CCCATTAACC
2801 TCACCGAGAG GCTTTTCCAG GTGCTCAGGT GGTCTACCGG
2841 CAGCCTCGAG ATCTTCTTCA GCAAGAACAA CCCGCTGTTC
2881 GGCTCCACCT ACCTGCATCC ACTCCAGAGG GTGGCCTACA
2921 TTAACATCAC CACCTACCCG TTCACCGCCA TCTTCCTCAT
2961 CTTCTACACG ACCGTGCCCG CCCTCTCATT CGTGACCGGC
3001 CATTTCATTG TGCAGAGGCC GACCACCATG TTCTACGTGT
3041 ACCTCGGGAT CGTGCTCGCC ACCCTCCTCA TTATTGCCGT
3081 GCTCGAGGTT AAGTGGGCTG GCGTGACCGT GTTCGAGTGG
3121 TTCCGCAACG GCCAGTTCTG GATGACCGCC TCTTGCTCTG
3161 CTTACCTCGC CGCTGTTTGC CAGGTCCTCA CCAAGGTTAT
3201 CTTCCGCAGG GACATCTCCT TCAAGCTCAC CTCCAAGCTC
3241 CCAGCCGGCG ACGAGAAGAA GGACCCATAC GCCGATCTGT
3281 ACGTGGTGAG GTGGACCCCG CTCATGATCA CCCCGATCAT
3321 CATCATTTTC GTCAACATCA TCGGCTCCGC GGTCGCCTTC
3361 GCCAAGGTGC TCGATGGCGA GTGGACCCAT TGGCTTAAGG
3401 TCGCCGGCGG CGTGTTCTTC AACTTCTGGG TTCTCTTCCA
3441 CCTCTACCCT TTCGCGAAGG GCCTTCTTGG CAAGCACGGC
3481 AAGACCCCAG TGGTGGTTCT TGTCTGGTGG GCCTTCACCT
3521 TCGTCATCAC CGCCGTGCTG TACATCAACA TCCCGCACAT
3561 CCATGGCGGC GGCGGCAAGC ACTCCGTGGG CCACGGCATG
3601 CACCATGGCA AGAAGTTCGA CGGCTACTAC CTCTGGCCGT
3641 GA
```

The nucleotide sequences with SEQ ID NOs:2-4 encode the CSLF6 protein from *Brachypodium distachyon* with SEQ ID NO:1, shown below.

```
  1 MAPAVAGGSS RGAGCKCGFQ VCVCSGSAAV ASAGSSLEVE
 41 RAMAVTPVEG QAAPVDGESW VGVELGPDGV ETDESGAGVD
 81 DRPVFKTEKI KGVLLHPYRV LIFVRLIAFT LFVIWRISHK
121 NPDTMWLWVT SICGEFWFGF SWLLDQLPKL NPINRIPDLA
161 VLRQRFDRAD GTSTLPGLDI FVTTADPIKE PILSTANSVL
201 SILAADYPVD RNTCYISDDS GMLMTYEAMA ESAKFATLWV
241 PFCRKHGIEP RGPESYFELK SHPYMGRAHD EFVNDRRRVR
281 KEYDDFKAKI NSLETDIQQR NDLHNAAVPQ NGDGIPRPTW
321 MADGVQWQGT WVEPSANHRK GDHAGIVLVL IDHPSHDRLP
361 GAPASADNAL DFSGVDTRLP MLVYMSREKR PGHNHQKKAG
401 AMNALTRASA LLSNAPFILN LDCDHYINNS QALRAGICFM
441 VGRDSDTVAF VQFPQRFEGV DPTDLYANHN RIFFDGTLRA
481 LDGMQGPIYV GTGCLFRRIT VYGFDPPRIN VGGPCFPALG
521 GLFAKTKYEK PSMEMTMARA NQAVVPAMAK GKHGFLPLPK
561 KTYGKSDKFV DTIPRASHPS PYAAEGIRVV DSGAETLAEA
```

-continued

```
601  VKVTGSAFEQ KTGWGSELGW VYDTVTEDVV TGYRMHIKGW
641  RSRYCSIYPH AFIGTAPINL TERLFQVLRW STGSLEIFFS
681  KNNPLFGSTY LHPLQRVAYI NITTYPFTAI FLIFYTTVPA
721  LSFVTGHFIV QRPTTMFYVY LGIVLATLLI IAVLEVKWAG
761  VTVFEWFRNG QFWMTASCSA YLAAVCQVLT KVIFRRDISF
801  KLTSKLPAGD EKKDPYADLY VVRWTPLMIT PIIIIFVNII
841  GSAVAFAKVL DGEWTHWLKV AGGVFFNFWV LFHLYPFAKG
881  LLGKHGKTPV VVLVWWAFTF VITAVLYINI PHIHGGGKH
921  SVGHGMHHGK KFDGYYLWP
```

A nucleic acid encoding an IRE1 unfolded protein response protein from *Brachypodium distachyon* was isolated and is shown below as SEQ ID NO:10.

```
   1  ATGAGGTCGC TCCGCCGGGT CCTCTTCCCG CTCGTCCTCC
  41  TTTCGGGGCT CGCCTTTCGT GGTGTCCACT TCAACGACGC
  81  CGCCGCCCCG ACCCCCCTTC TCCTCCCGCT TTCCCCACCA
 121  CCGGCGCTGC CGTCGCCGCC CCTCGCGCTC CCTGCTGACG
 161  AAGGGCGAGG GGATGGTGCG GACTCCAGGG AGATCATCGC
 201  GGCGCCGCTG CCCGGGGAGC TCCTTGTCAG GCCGCCCCGC
 241  CGCCGCTCGG AGCCGACGAA CGCGGTGACC GATGCTGGCC
 281  CCCACATCAG CTCCGAACTA CAATTCAACG ACGATGGCAC
 321  AATTCAACTT GTTGATCGTC TATCAAAATC TTCTTTGTGG
 361  CAGTTCTCCA CAGGACCGCC TCTTTCGAAG CATGTCACTA
 401  CAGCAAACTC AGATTTGGGC TATCTCATAT ATCCTTTAGA
 441  TCAAGCTAAG CTTGTGGAAG TTCATAATGG CAGTGTTATG
 481  GCACTTCCCT GGGAACTGGA CGAGTTTATT AGCAGAACTC
 521  CGTATGTACG GGACTCTGTC GTTACTATTG GATCAAAAAC
 561  TTCAACTATT TTTGCAGTTG ATGCTGATAG TGGGGAGATC
 601  ATTTACAAGC ATAGCTTGCC AATCGCTTTG AATGAATTAG
 641  GAGCAACCCC TGTTGAAGAA GCACCATCCA AGCTGGATGC
 681  TGGTAGAAGT GGTAGTCCTA ATGTCATAGT GCTTGTTAGA
 721  ACTGATTATT CTGTCAGTGC GTCTGACCTA GGCGTTCATT
 761  TGTTTAACTG GACAAGAACT TCTTTCTCTG CAAACTATTA
 801  TGTGAAACAG AGCCATCCAG ATACGTTAGA ACAATCATCC
 841  TGTCTGCGAG GAAATATTCC TTGCTTTAGG TCTGATGGTG
 881  TACCACTTAA ACTCACGTTA CCTGAGTCTA GTACAGCCAA
 921  TGCACTTGTC TTGAGAGATT TGAACAAAGT TACCACTAGG
 961  TATGATGCTG ATGCCTTGAG ACCAGTTGCA ACTATGATGA
1001  AGTCACTACA AGCTGCTAGC AAGTCTAATG TTGTTCTGGA
1041  CAGTACTCAG AATCAAACTG TTGATGATGC TCCTGGTCGC
1081  CTTGTCTCTG CTGATCCCCA AGCCAACAGG TTCAGTAACA
1121  ATACTCATGG ATTGTTATTC CCTGTTGTTT CCTTATTGGT
1161  GGTCCTCGCT TGGCTAGTGA GCTTGGCCTA TTCAAGCAAG
1201  CCTTGCAGGC AATTCGTGGG TCAGCTTTTT AAGCCATTTG
1241  TCCATGAAAA GAAATCGACA GGCCTTGCAG GAAAGACAGA
1281  GAAAACTTCT AAGAGAAGAA AAACACGAAA GAAAGACGGA
1321  ATTGCCAATG GCACTGATAT CTGTTCATCA TCTGACAAAG
1401  AGAACGGTGA AACTGGTGGG TCAAATGAGA CGGTATATAA
1441  TGAAACCTAC CAATTAACAG GTACCGCACT CCCTGATGGT
1481  CTTGATGGAT GCCAGATTGA TAAGCTTCGT GTTCACAAAA
1521  AAGAAATTGG TAAAGGGAGC AATGGTACAG TTGTCTTTGA
1561  GGGTTCCTAT GATGGTCGTG AAGTTGCAGT GAAACGTCTG
1601  CTACGTTCAC ACACTGATAT AGCGCAAAAA GAGATTCAGA
1641  ATCTTATTGC ATCCGACCGG GATCCTAATA TCGTTAGACT
1681  GTATGGCTGC GATCAGGATG ATAATTTTGT TTATATCTCC
1721  CTTGAGAGAT GCCGCTGCAG CTTGGCTGAT CTTATTCAAC
1761  AGCATATAGA TCCATCATTT TCAGATGTTG AGCGAATAGA
1801  TGTTGAACTG TGGAGGCAGG ATGGGCTCCC TTCCGCACAA
1841  CTCCTAAAGC TGATGAGAGA TGTTGTTGCT GGCATTGTGC
1881  ATTTGCATAG TTTAGGAATC ATACATCGCG ATTTGAAGCC
1921  TCAGAACGTT TTGATAAGTA AGGAAGGACC TCTCAGCGCA
1961  AAACTTTCAG ATATGGGTAT CAGTAAGCGC TTGCAAGAGG
2001  ATATGACTTC TCTTAGCCAT CATGGTACTG GATATGGAAG
2041  CTCTGGTTGG CAAGCACCTG AACAGCTTCG TGGTGATAGT
2081  CAGACTCGTG CAATGGATTT ATTTAGTTTG GGCTGCCTTA
2121  TTTTCTATTG TATCACCAAA GGCAAGCATC CGTTTGGTGA
2201  GTACTATGAG CGGGACATGA ACATTATAAA CAATCACTTT
2241  GATCTCTTCG TGGTGGATCA CATACCAGAA GCAGTACATC
2281  TTATTTCTCA ATTGTTACAG CCAAAACCAG AAATGAGACC
2321  AACGGCAGTA TACGTGATAA ATCATCCTCT CTTCTGGTGC
2361  CCTGAGTTGC GGCTTCTGTT CCTACGGGAT ACCAGTGACA
2401  GAATTGAGAA AACCACTGAA ACTGACCTCA TAAATGCTTT
2441  GGAAAGCATA GGGTATGAAG CGTTTGGTGG AAAATGGCGA
2481  GAAAAGTTGG ATGATGGTCT GGTTGCCGAC ATGGGTCGTT
2521  ATAGGAAATA TAATTTTGAG TCCACACGTG ACCTTCTGAG
2561  GTTGATTAGA AATAAGTCAG GACATTACAG GGAGCTGCCA
2601  GCTGATCTCA AGGAATTACT TGGGTCGCTG CCTGAGGGAT
2641  TTGATCGCTA TTTCTCAAGC CGATTTCCAA AGCTGCTGAT
2681  TGAAGTGTAC AAGGTCATGT CTGTGCACTG CAAGGATGAG
2721  GAAGCTTTCA GGAAATATTT CATTGGAAGC TCGGTATAA
```

An amino acid sequence for the IRE1 unfolded protein response protein from *Brachypodium distachyon* that is encoded by the SEQ ID NO:10 nucleic is shown below as SEQ ID NO:9.

```
  1 MRSLRRVLFP LVLLSGLAFR GVHFNDAAAP TPLLLPLSPP
 41 PALPSPPLAL PADEGRGDGA DSREIIAAPL PGELLVRPPR
 81 RRSEPTNAVT DAGPHISSEL QFNDDGTIQL VDRLSKSSLW
121 QFSTGPPLSK HVTTANSDLG YLIYPLDQAK LVEVHNGSVM
161 ALPWELDEFI SRTPYVRDSV VTIGSKTSTI FAVDADSGEI
201 IYKHSLPIAL NELGATPVEE APSKLDAGRS GSPNVIVLVR
241 TDYSVSASDL GVHLFNWTRT SFSANYYVKQ SHPDTLEQSS
281 CLRGNIPCFR SDGVPLKLTL PESSTANALV LRDLNKVTTR
321 YDADALRPVA TMMKSLQAAS KSNVVLDSTQ NQTVDDAPGR
361 LVSADPQANR FSNNTHGLLF PVVSLLVVLA WLVSLAYSSK
401 PCRQFVGQLF KPFVHEKKST GLAGKTEKTS KRRKTRKKDG
441 IANGTDICSS SDKENGETGG SNETVYNETY QLTGTALPDG
481 LDGCQIGKLR VHKKEIGKGS NGTVVFEGSY DGREVAVKRL
521 LRSHTDIAQK EIQNLIASDR DPNIVRLYGC DQDDNFVYIS
561 LERCRCSLAD LIQQHIDPSF SDVERIDVEL WRQDGLPSAQ
601 LLKLMRDVVA GIVHLHSLGI IHRDLKPQNV LISKEGPLSA
641 KLSDMGISKR LQEDMTSLSH HGTGYGSSGW QAPEQLRGDS
681 QTRAMDLFSL GCLIFYCITK GKHPFGEYYE RDMNIINNHF
721 DLFVVDHIPE AVHLISQLLQ PKPEMRPTAV YVINHPLFWC
761 PELRLLFLRD TSDRIEKTTE TDLINALESI GYEAFGGKWR
801 EKLDDGLVAD MGRYRKYNFE STRDLLRLIR NKSGHYRELP
841 ADLKELLGSL PEGFDRYFSS RFPKLLIEVY KVMSVHCKDE
881 EAFRKYFIGS SV
```

The CSLF6 codon-optimized nucleic acid (SEQ ID NO:3) was operably linked to the CaMV 35S promoter by insertion into a pJJ271 expression vector (FIG. 1A). The IRE1 nucleic acid (SEQ ID NO:10) was operably linked to a *Brachypodium* PIN-like protein promoter by insertion into a p6MoIBISH04 expression vector.

These expression vectors were stably introduced into *Brachypodium distachyon* by procedures described by Bragg et al. *Brachypodium distachyon* in Kan Wang (ed.), AGROBACTERIUM PROTOCOLS, Vol 1, METHODS IN MOLECULAR BIOLOGY, 1223: 17-33 (2015).

Example 2: Over-Expression of IRE1 Increases Growth of Plants

Figure 2:
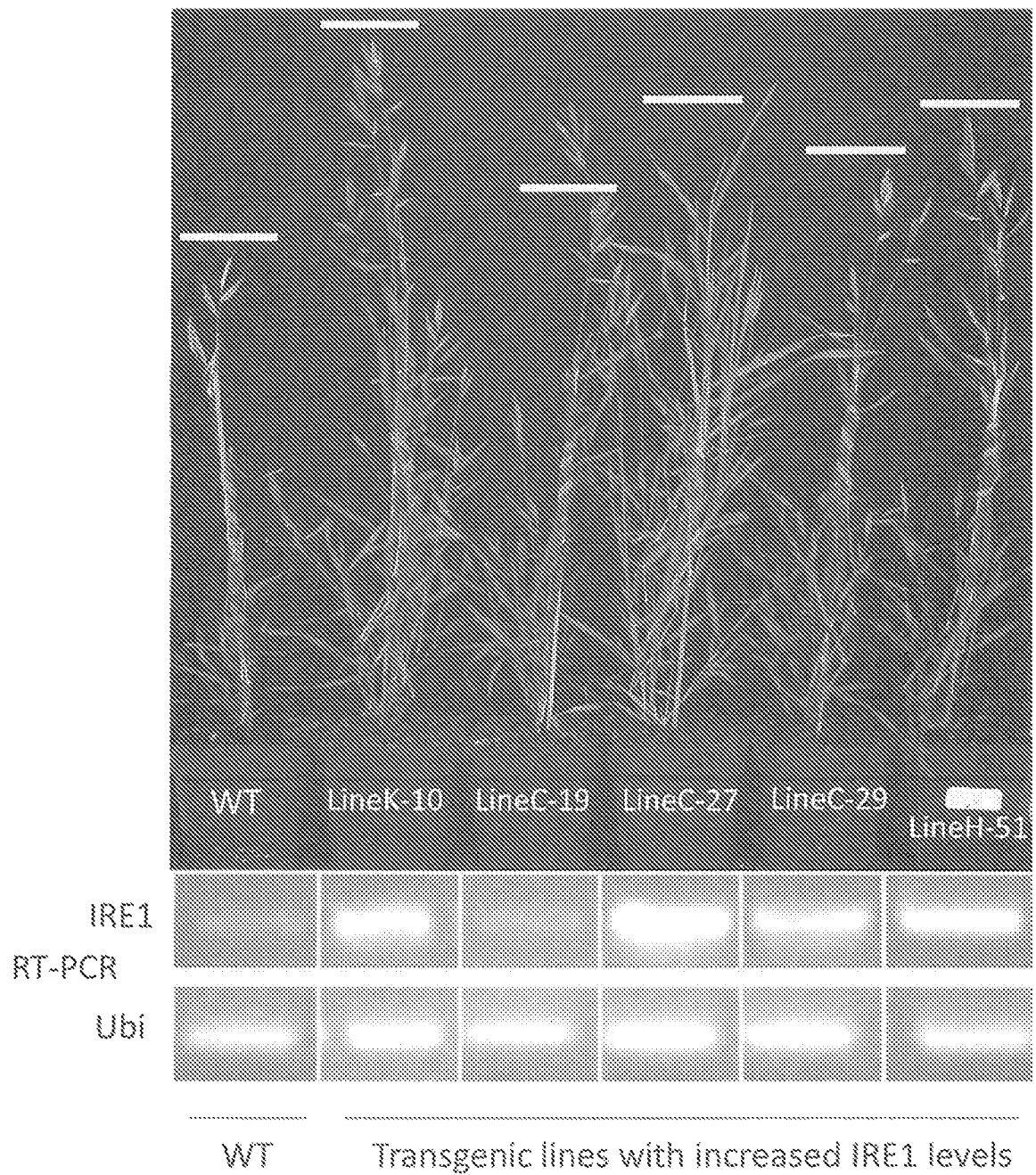
FIG. 2 illustrates that increased expression of IRE1 increases plant growth compared to wild type (WT). Lines K-10, C-27, C-29 and H-51 exhibit increased expression of IRE1 as shown in the quantitative real-time polymerase chain (RT-PCR) results shown below the image of plants. Lines K-10, C-27, C-29 and H-51 also exhibit increased plant height relative to wild type and Line C-19 plants. In contrast, wild type and LineC-19 plants exhibit low or almost non-detectable levels of IRE1 expression, and reduced plant growth.

As illustrated in FIG. 2, overexpression of IRE1 improved growth of *Brachypodium distachyon* plant lines K-10, C-27, C-29 and H-51. Note that these plant lines expressed increased levels of IRE1 relative to wild type *Brachypodium distachyon* and compared to a *Brachypodium distachyon* line that did not express IRE1 at levels greater than wild type (line C-19).

*Brachypodium distachyon* plant lines K-10, C-27, C-29 and H-51 exhibited significantly greater growth than either wild type *Brachypodium distachyon* and compared to a *Brachypodium distachyon* line that did not express IRE1 at levels greater than wild type (line C-19) (FIG. 2).

Example 3: IRE1 Overcomes Growth Inhibition by CSLF6 Expression

Figure 3:
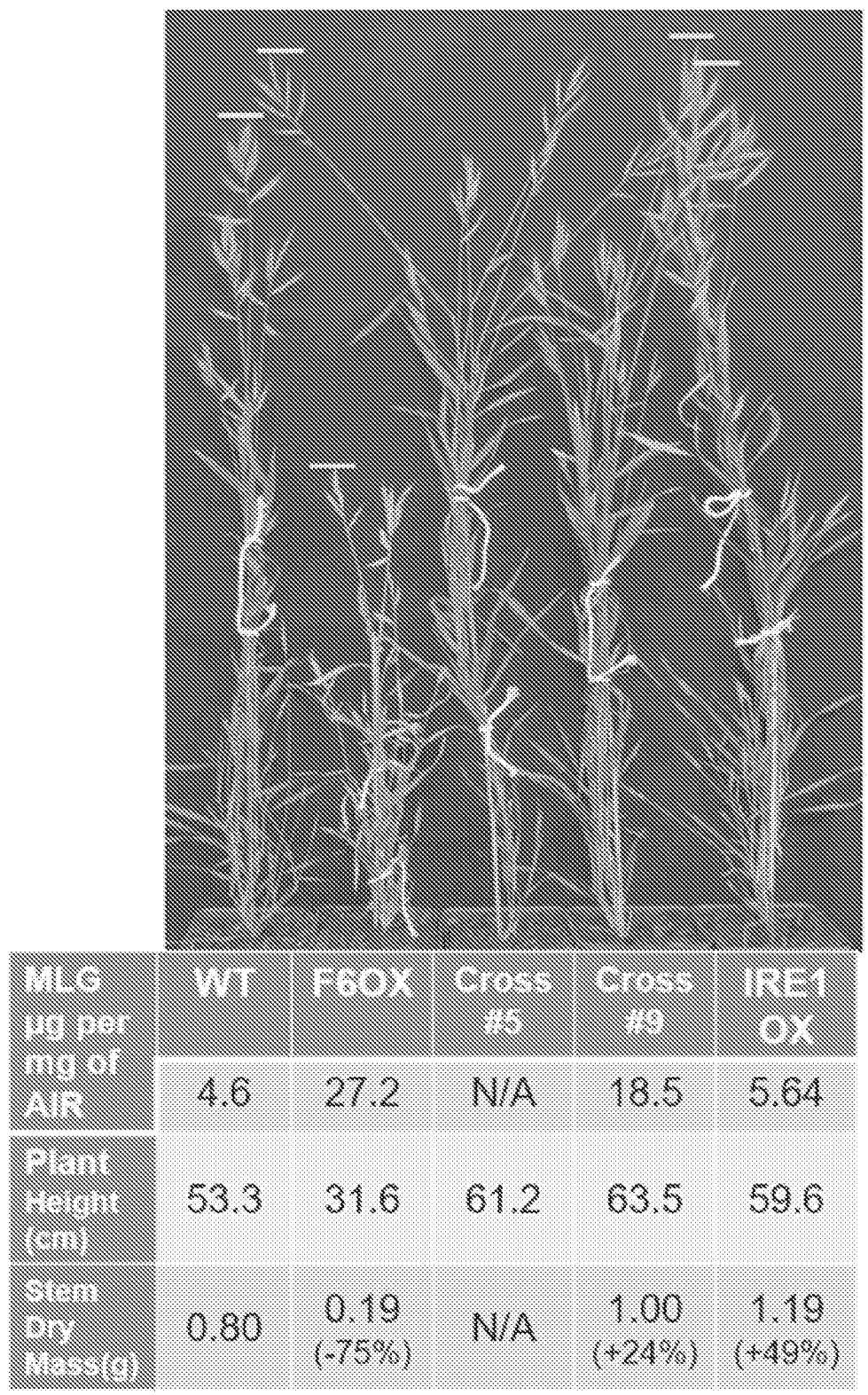
FIG. 3 shows that increased IRE1 expression overcomes the growth penalty associated with over-expression of CSLF6. As illustrated, plants that over-express IRE1 and CSLF6 exhibit normal to improved plant growth, increased dry stem mass, and enhanced glucan content.

As illustrated in FIG. 3, overexpression of IRE1 improved growth of *Brachypodium distachyon* plant lines that overexpressed CSLF6. Plant lines that overexpress CSLF6 (referred to as F6OX plant lines) exhibit reduced growth relative to wild type plants that express endogenous levels of CSLF6 (FIG. 3). However, when IRE1 is also expressed with CSLF6, the plants grow normally.

Example 4: IRE1 and CSLF6 Co-Expression Increases Glucan Content

As shown in Table 1, when IRE1 is expressed with CSLF6, plants not only grow normally but also have higher glucan (MLG) content. As shown in the first two columns, wild type plants tend to be taller and have greater stem dry mass than plants that overexpress CSLF6 without any transgenic IRE1 expression (i.e., F6OX plants). However, Table 1 also shows that the F6OX plants that overexpress CSLF6 have significantly greater glucan content (27.2 µg glucan/mg Air) compared to wild type plants (4.6 µg glucan/mg Air). When IRE1 is introduced (cross #5 and #9) into plants that overexpress CSLF6, plant height is restored to normal or increased height levels, and cross #9 plants that express both CSLF6 and IRE1 still have increased glucan content compared to wild type plants.

TABLE 1

Height and Glucan Content of Wild Type vs. Transgenic Plant Lines

|  | Wild Type | F6OX | Cross #5 | Cross #9 | IRE1 OX |
|---|---|---|---|---|---|
| µg glucan/mg of AIR | 4.6 | 27.2 | N/A | 18.5 | 5.64 |
| Plant Height (cm) | 53.3 | 31.6 | 61.2 | 63.5 | 59.6 |
| Stem Dry Mass (g) | 0.80 | 0.19 (−75%) | TBD | 1.00 (+24%) | 1.19 (+49%) |

Example 5: IRE1 and CSLF6 Overexpression Increases in MLG

This Example illustrates mixed-linkage glucan (MLG) content of vegetative *Brachypodium* tissues that express CSLF6, or a combination of IRE1 and CSLF6, during development.

Methods

The deposition of mixed-linkage glucan (MLG) in leaves and stems of transgenic plant lines was separately analyzed during development of transgenic *Brachypodium* plants. Alcohol insoluble residue (AIR) was isolated from lyophilized leaf and stem as described by York et al. (*Methods in Enzymology* (Academic Press), Vol 118, pp 3-40 (1986)). Quantification of mixed linkage glucan was performed using β-Glucan assay kit (Megazyme) with 3 mg of alcohol insoluble residue. In this assay, alcohol insoluble residue was digested with lichenase to release oligosaccharides, which were further digested by β-glucosidase to generate glucose. The amount of glucose was quantified colorimetrically by GOPOD (glucose oxidase/peroxidase) reagent using D-glucose as a standard.

Results

Figure 4A:
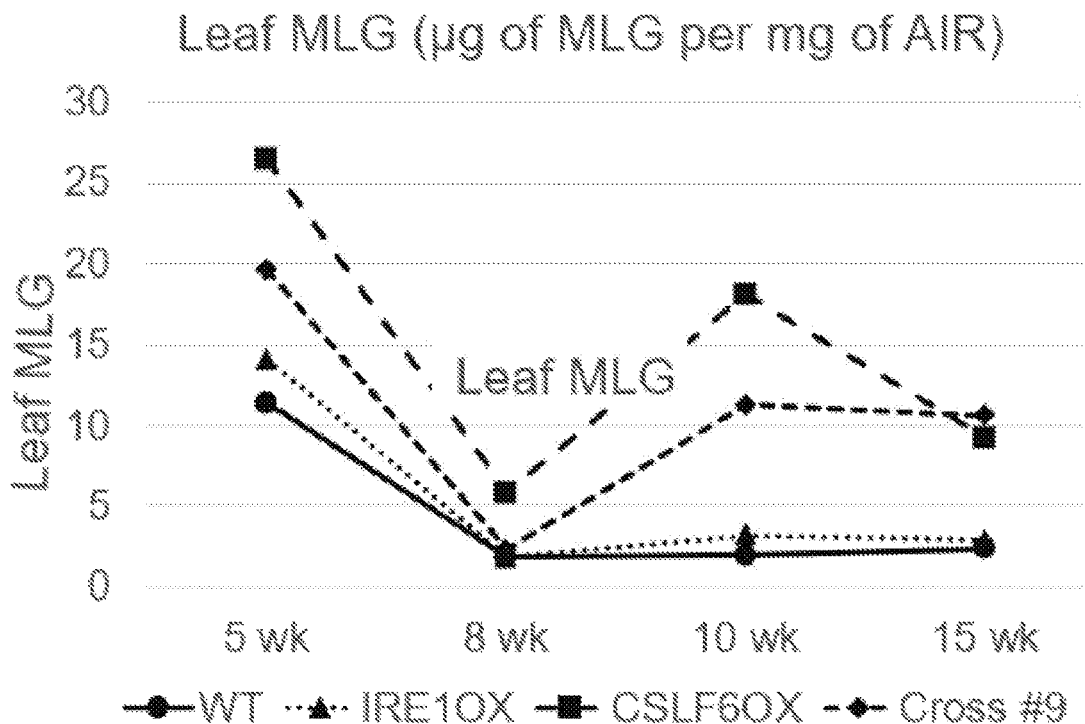
FIG. 4A-4B illustrate the amount of mixed-linkage glucan (MLG; μg of MLG per mg of alcohol insoluble residue (AIR)) in leaves and stems of *Brachypodium* tissues that express CSLF6 (CSLF6OX), or a combination of IRE1 and CSLF6 (Cross #9).
Figure 4B:
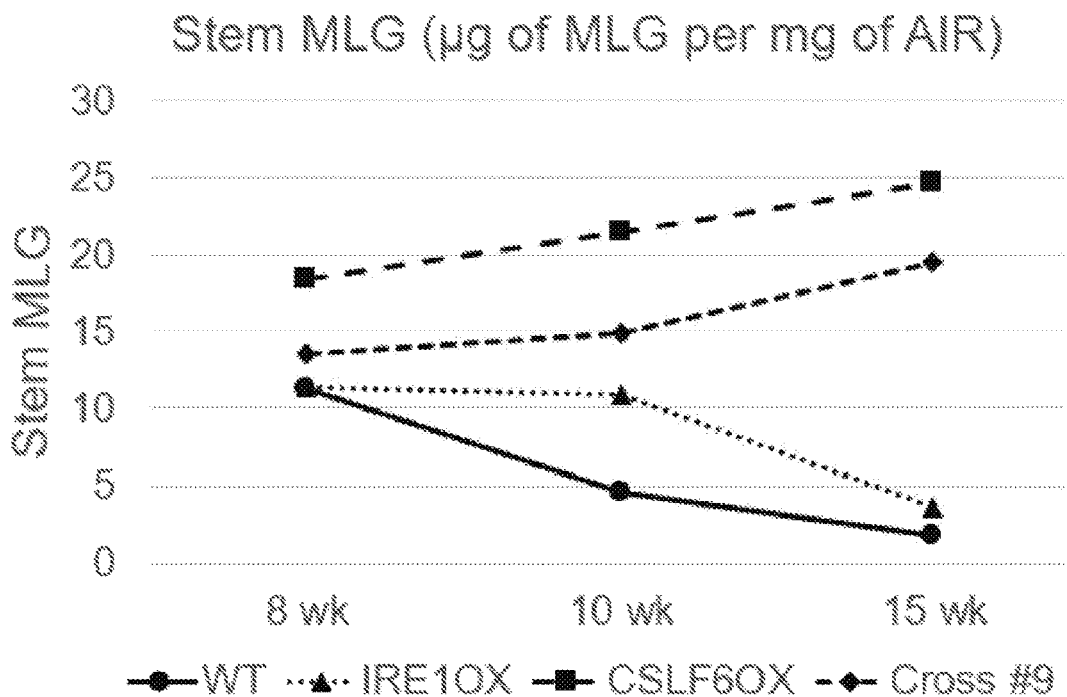

FIG. 4A-4B illustrate that *Brachypodium* tissues that express CSLF6 (CSLF6OX), or a combination of IRE1 and CSLF6 (Cross #9), have higher mixed-linkage glucan content than wild plant tissues or tissues from plants that overexpress only IRE1.

These data indicate that *Brachypodium* that have the CSLF6 expression cassette can store more MLG compared to WT even after programmed MLG degradation at the growth phase transition from vegetative to reproductive stage (8 week). In addition, the growth improvement of combined CSLF6×IRE1 expression (from CSLF6OX× IRE1OX crosses) occurs without reduction of MLG in the plant tissues. As illustrated, high levels of MLG are maintained in the CSLF6OX×IRE1OX crosses.

Example 6: IRE1 Extends Vegetative Growth

This Example illustrates that plants containing the IRE1OX expression cassette have a higher proportion of biomass from vegetative tissues than plants without IRE1OX expression cassette Methods Dry mass from leaves, stems and spikelets of *Brachypodium* plants at 8 weeks and 10 weeks were quantified separately, and the relative portion of dry mass from each tissue was determined.

Results

Figure 5:
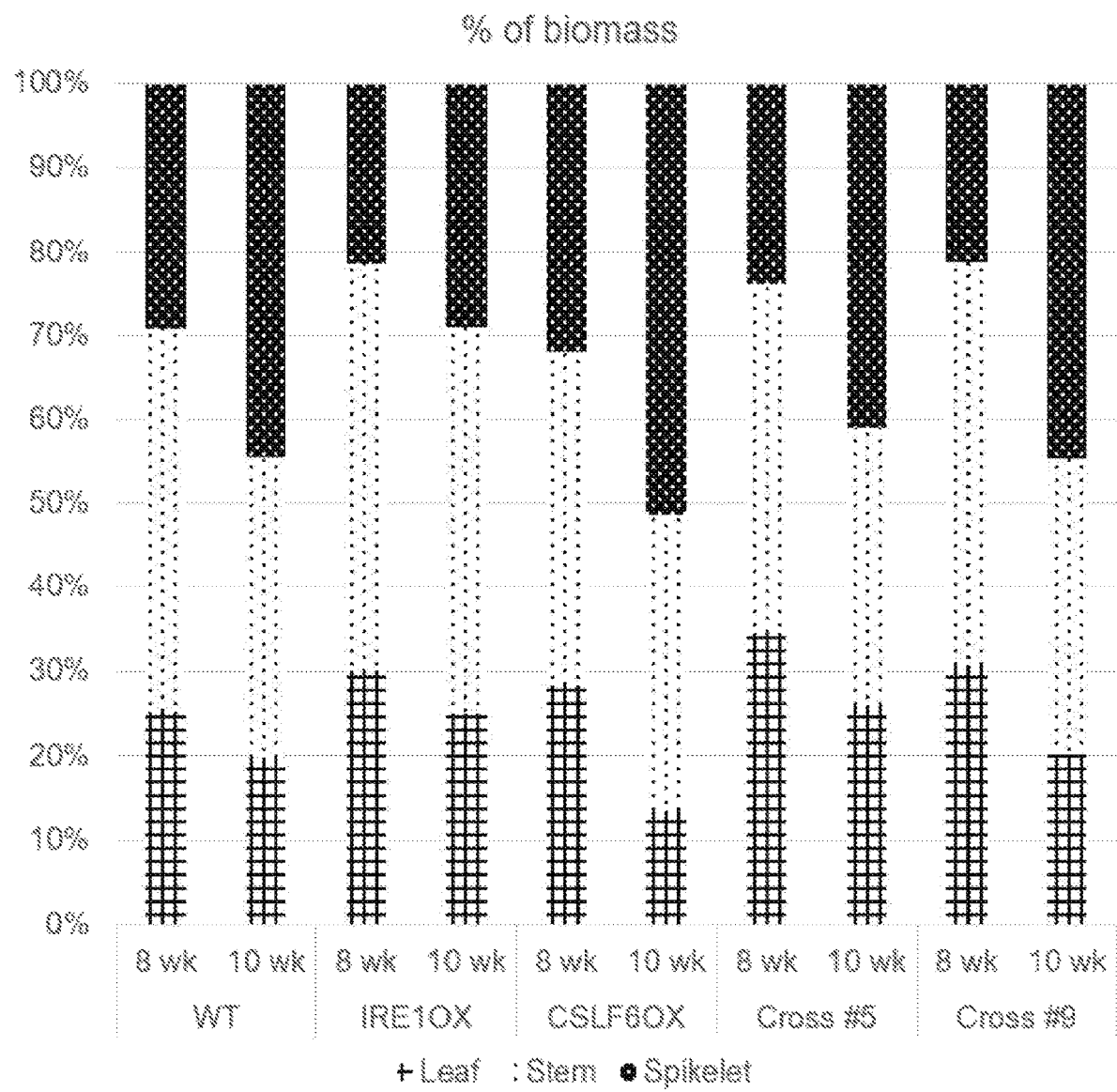
FIG. 5 graphically illustrates the percent biomass of leaves, stems and spikelets in *Brachypodium* plants expressing IRE1, CSLF6, or a combination of CSLF6 and IRE1 at 8 weeks and 10 weeks of development.

FIG. 5 illustrates the percent biomass of leaves, stems and spikelets of *Brachypodium* plants expressing IRE1, CSLF6, or a combination of CSLF6 and IRE1 at 8 weeks and 10 weeks of development. As shown, plants expressing IRE1 have higher percentages of stem and leaf biomass than wild type plants that do not overexpress IRE1.

Example 7: Stem Specific Expression of IRE1

This Example illustrates use of a stem specific promoter to express IRE1 in the tissue and development-specific manner.

Methods

To understand development and tissue specific expression of IRE1, RT-PCR analysis was performed using IRE1-specific primers. Total RNA was extracted from top node, peduncle and 3$^{rd}$ internode from *Brachypodium* WT and transgenic lines using a Nucleospin RNA plant kit (Macherey-Nagel) and treated with DNase I in the kit. All samples within an experiment were reverse-transcribed at the same time using an iScript™ (Biorad). Real-time quantitative real-time RT-PCR with SYBR Green detection was performed in triplicate using the Applied Biosystems 7500 fast real-time PCR system. The IRE1-specific primers employed had the following sequences:

```
IRE1 FP:
                                        (SEQ ID NO: 17)
CAAGCATCCGTTTGGTGAGT

IRE1 RP:
                                        (SEQ ID NO: 18)
TCACGTATACTGCCGTTGGT

UbiE2 FP:
                                        (SEQ ID NO: 19)
CAGCATTTGCCTTGACATTC
```

```
UbiE2 RP:
                                        (SEQ ID NO: 20)
GCAGCGAACAGATAGACAGG
```

Data were analyzed by the ΔΔCT method. The transcript level was normalized to that of the ubiquitin-conjugating enzyme E2 gene (UBI E2) for each sample. The relative transcript level of IRE1 was expressed as the fold change (mean±STD) in each genotype relative to the wild-type (set to a value of 1). Three independent experiments were performed in triplicate.

Results

Figure 6:
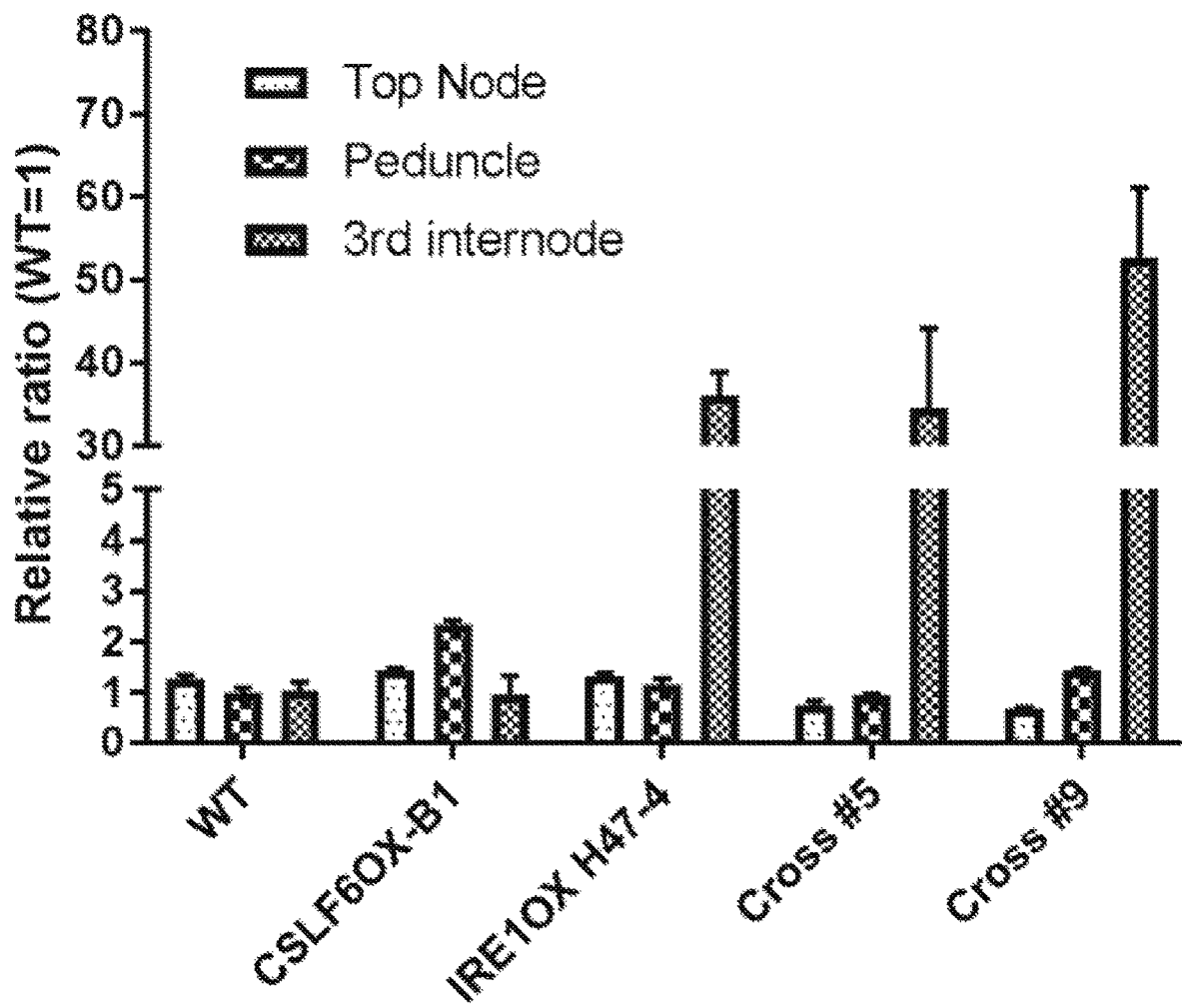
FIG. 6 graphically illustrates IRE1 expression as the fold change (mean±STD) relative to wild-type plant expression of IRE1 in top node, peduncle, and $3^{rd}$ internode tissues of *Brachypodium* plants overexpressing CSLF6, IRE1, or a combination of CSLF6 and IRE1 (cross #9).

FIG. 6 graphically illustrates IRE1 expression as the fold change (mean±STD) relative to wild-type plant expression of IRE1 in top node, peduncle, and 3$^{rd}$ internode tissues of *Brachypodium* plants overexpressing CSLF6, IRE1, or a combination of CSLF6 and IRE1 (cross #5 and cross #9).

As illustrated, IRE1 was specifically expressed in the 3$^{rd}$ internode of the plants with the IRE1OX expression cassette, but no significant IRE1 expression was observed in the top node and peduncle. These results indicate that the stem specific promoter does express IRE1 in the tissue and development-specific manner All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements describe some of the elements or features of the invention. The statements provide features that can be claimed in the application and the dependencies of the statements illustrate combinations of features that can be present when included in the claims.

Statements:

1. A plant cell, plant seed, or plant comprising an expression system comprising at least one (first) expression cassette comprising a promoter operably linked to nucleic acid segment encoding an IRE1 polypeptide.
2. The plant cell, plant seed, or plant of statement 1, wherein the expression system further comprises at least one (second) expression cassette comprising a promoter operably linked to nucleic acid segment encoding a CSLF6 polypeptide.
3. The plant cell, plant seed, or plant of statement 1 or 2, wherein the nucleic acid segment encoding the IRE1 polypeptide and/or the nucleic acid segment encoding the CSLF6 polypeptide is heterologous to the plant.
4. The plant cell, plant seed, or plant of statement 1, 2, or 3, wherein a population of plants having the expression system has an average height that is within 10% of an average height of a corresponding wild type population of plants of the same age, where the wild type population of plants does not have the expression system.
5. The plant cell, plant seed, or plant of statement 1-3 or 4, wherein a population of plants having the expression system has an average height that is at least 5% greater, or at least 10% greater, or at least 15% greater, or at least 20% greater, or at least 30% greater, than an average height of a corresponding wild type population of plants of the same age, where the wild type population of plants does not have the expression system.

6. The plant cell, plant seed, or plant of statement 1-4, or 5, wherein a population of plants having the expression system has an average dry stem mass that is within 10% of an average dry stem mass of a corresponding wild type population of plants of the same age, where the wild type population of plants does not have the expression system.
7. The plant cell, plant seed, or plant of statement 1-5 or 6, wherein a population of plants having the expression system has an average dry stem mass that is at least 5% greater, or at least 10% greater, or at least 15% greater, or at least 20% greater, or at least 30% greater, than an average dry stem mass of a corresponding wild type population of plants of the same age, where the wild type population of plants does not have the expression system.
8. The plant cell, plant seed, or plant of statement 1-6 or 7, wherein a population of plants having the expression system has an average glucan content that is at least 5% greater, or at least 10% greater, or at least 15% greater, or at least 20% greater, or at least 25% greater, or at least 30% greater, or at least 35% greater, or at least 40% greater, than an average glucan content of a corresponding wild type population of plants of the same age, where the wild type population of plants does not have the expression system.
9. The plant cell, plant seed, or plant of statement 1-7 or 8, which is a forage plant (e.g., alfalfa, clover, soybeans, turnips, bromegrass, bluestem, and fescue), starch plant (e.g., canola, potato, lupin, sunflower or cottonseed), grain-producing plant (maize, wheat, barley, oats, rice, sorghum, millet, rye), vegetable plant (e.g., cucumber, tomato, broccoli, pea), grass plant (switchgrass, *miscanthus*, prairie grass, wheat grass, sudangrass, sorghum, straw-producing plant), sugar producing plant (sugarcane, beets), *Brachypodium, Arabidopsis*, bamboo, softwood, hardwood, or woody plant (e.g., those used for paper production such as poplar species, pine species, and *eucalyptus*).
10. The plant cell, plant seed, or plant of statement 1-8 or 9, wherein the promoter is a strong, weak, or inducible promoter.
11. The plant cell, plant seed, or plant of statement 1-9 or 10, wherein the promoter is a CaMV 35S promoter, CaMV 19S promoter, nos promoter, Adh1 promoter, sucrose synthase promoter, α-tubulin promoter, ubiquitin promoter, actin promoter, cab promoter, PEPCase promoter, R gene complex promoter, poplar xylem-specific secondary cell wall specific cellulose synthase 8 promoter, cauliflower mosaic virus promoter, Z10 promoter from a gene encoding a 10 kDa zein protein, Z27 promoter from a gene encoding a 27 kDa zein protein, pea rbcS gene (Coruzzi et al., *EMBO J.* 3:1671 (1971)) and the actin promoter from rice promoter, or phaseolin promoter.
12. The plant cell, plant seed, or plant of statement 1-10 or 11, wherein the promoter is a *Brachypodium* PIN-like promoter.
13. A method comprising (a) generating a plant cell comprising an expression system comprising at least one (first) expression cassette comprising a promoter operably linked to nucleic acid segment encoding an IRE1 polypeptide; and (b) generating a plant from the plant cell.
14. The method of statement 13, further comprising introducing at least one second expression cassette into the plant cell, where the second expression cassette comprises a promoter operably linked to nucleic acid segment encoding a CSLF6 polypeptide; and then (b) generating a plant from the plant cell.
15. The method of statement 13 or 14, wherein the promoter is a strong, weak, or inducible promoter.
16. The method of statement 13, 14, or 15, wherein the promoter is a CaMV 35S promoter, CaMV 19S promoter, nos promoter, Adh1 promoter, sucrose synthase promoter, α-tubulin promoter, ubiquitin promoter, actin promoter, cab promoter, PEPCase promoter, R gene complex promoter, poplar xylem-specific secondary cell wall specific cellulose synthase 8 promoter, cauliflower mosaic virus promoter, Z10 promoter from a gene encoding a 10 kDa zein protein, Z27 promoter from a gene encoding a 27 kDa zein protein, pea rbcS gene (Coruzzi et al., *EMBO J.* 3:1671 (1971)) and the actin promoter from rice promoter, or phaseolin promoter.
17. The method of statement 13-15 or 16, wherein the promoter is a *Brachypodium* PIN-like promoter.
18. A method comprising (a) growing a plant comprising an expression system comprising at least one (first) expression cassette comprising a first promoter operably linked to nucleic acid segment encoding an IRE1 polypeptide to produce a grown plant; and (b) harvesting biomass from the grown plant.
19. The method of statement 18, wherein the expression system further comprises at least one (second) expression cassette comprising a second promoter operably linked to nucleic acid segment encoding a CSLF6 polypeptide.
20. The method of statement 18 or 19, wherein the first promoter or the second promoter is a strong, weak, or inducible promoter.
21. The method of statement 18, 19, or 20, wherein the first promoter and the second promoter are separately selected from a CaMV 35S promoter, CaMV 19S promoter, nos promoter, Adh1 promoter, sucrose synthase promoter, α-tubulin promoter, ubiquitin promoter, actin promoter, cab promoter, PEPCase promoter, R gene complex promoter, poplar xylem-specific secondary cell wall specific cellulose synthase 8 promoter, cauliflower mosaic virus promoter, Z10 promoter from a gene encoding a 10 kDa zein protein, Z27 promoter from a gene encoding a 27 kDa zein protein, pea rbcS gene (Coruzzi et al., *EMBO J.* 3:1671 (1971)) and the actin promoter from rice promoter, or phaseolin promoter.
22. The method of statement 18-20 or 21, wherein the first promoter and the second promoter are separately selected is a *Brachypodium* PIN-like promoter.
23. The method of statement 13-21 or 22, further comprising planting a seed comprising the expression system comprising at least one (first) expression cassette comprising a promoter operably linked to nucleic acid segment encoding an IRE1 polypeptide to produce the plant.
24. The method of statement 13-22, or 23, further comprising isolating glucan, oligosaccharides, disaccharides, monosaccharides, or a combination thereof from the biomass.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed is:

1. A plant cell, plant seed, or plant comprising an expression system comprising (a) a first expression cassette comprising a first promoter operably linked to a nucleic acid segment encoding an IRE1 polypeptide comprising an amino acid sequence with at least 95% sequence identity to any of SEQ ID NO: 9 and 11, 12, 13, 14, or 15; and (b) a second expression cassette comprising a second promoter operably linked to a nucleic acid segment encoding a CSLF6 polypeptide comprising an amino acid sequence with at least 95% sequence identity to any of SEQ ID NO: 1, 5, 6, 7, or 8, wherein the plant cell, plant seed, or plant are selected from the group consisting of Brachypodium distachyon, wheat, barely, corn, rice, or sorghum.

2. The plant of claim 1, wherein a population of the plants having the expression system has an average dry stem mass that is at least 5% greater than an average dry stem mass of a corresponding wild type population of plants of the same age, where the wild type population of plants does not have the expression system.

3. The plant of claim 1, wherein a population of the plants having the expression system has an average glucan content that is at least 5% greater than a glucan content of a corresponding wild type population of plants of the same age, where the wild type population of plants does not have the expression system.

4. The plant cell, plant seed, or plant of claim 1, wherein the first promoter or the second promoter is a strong or inducible promoter.

5. The plant cell, plant seed, or plant of claim 1, wherein the first promoter or the second promoter is a tissue-specific promoter.

6. The plant cell, plant seed, or plant of claim 1, wherein the first promoter and the second promoter are separately selected from a CaMV 35S promoter, CaMV 19S promoter, nos promoter, Adh1 promoter, sucrose synthase promoter, a-tubulin promoter, ubiquitin promoter, actin promoter, cab promoter, PEPCase promoter, R gene complex promoter, poplar xylem-specific secondary cell wall specific cellulose synthase 8 promoter, cauliflower mosaic virus promoter, Z10 promoter from a gene encoding a 10 kDa zein protein, Z27 promoter from a gene encoding a 27 kDa zein protein, pea rbcS gene and the actin promoter from rice promoter, or phaseolin promoter.

7. A method comprising growing a plant seed or plant comprising an expression system comprising (a) a first expression cassette comprising a first promoter operably linked to a nucleic acid segment encoding an IRE1 polypeptide comprising an amino acid sequence with at least 95% sequence identity to any of SEQ ID NO: 9 and 11, 12, 13, 14, or 15; and (b) a second expression cassette comprising a second promoter operably linked to a nucleic acid segment encoding a CSLF6 polypeptide comprising an amino acid sequence with at least 95% sequence identity to any of SEQ ID NO: 1, 5, 6, 7, or 8, to thereby produce a mature plant, wherein the plant cell, plant seed, or plant are selected from the group consisting of Brachypodium distachyon, wheat, barely, corn, rice, or sorghum.

8. The method of claim 7, further comprising harvesting biomass from the mature plant.

9. The method of claim 8, further comprising isolating glucan, oligosaccharides, disaccharides, monosaccharides, or a combination thereof from the biomass.

10. The method of claim 8, wherein the first promoter or the second promoter is a strong or inducible promoter.

11. The method of claim 8, wherein the first promoter or the second promoter is a tissue-specific promoter.

12. The method of claim 7, wherein the first promoter and the second promoter are separately selected from a CaMV 35S promoter, CaMV 19S promoter, nos promoter, Adh1 promoter, sucrose synthase promoter, a-tubulin promoter, ubiquitin promoter, actin promoter, cab promoter, PEPCase promoter, R gene complex promoter, poplar xylem-specific secondary cell wall specific cellulose synthase 8 promoter, cauliflower mosaic virus promoter, Z10 promoter from a gene encoding a 10 kDa zein protein, Z27 promoter from a gene encoding a 27 kDa zein protein, pea rbcS gene and the actin promoter from rice promoter, or phaseolin promoter.

13. The plant of claim 1, wherein a population of the plants having the expression system has an average height that is the same as or at least 5% greater than an average height of a corresponding wild type population of plants of the same age, where the wild type population of plants does not have the expression system.

14. The method of claim 7, wherein a population of the plants having the expression system has an average height that is the same as or at least 5% greater than an average height of a corresponding wild type population of plants of the same age, where the wild type population of plants does not have the expression system.

* * * * *

SEQUENCE LISTING

```
<160> NUMBER OF SEQ ID NOS: 20

<210> SEQ ID NO 1
<211> LENGTH: 939
<212> TYPE: PRT
<213> ORGANISM: Brachypodium distachyon

<400> SEQUENCE: 1

Met Ala Pro Ala Val Ala Gly Gly Ser Ser Arg Gly Ala Gly Cys Lys
1               5                   10                  15

Cys Gly Phe Gln Val Cys Val Cys Ser Gly Ser Ala Ala Val Ala Ser
            20                  25                  30

Ala Gly Ser Ser Leu Glu Val Glu Arg Ala Met Ala Val Thr Pro Val
        35                  40                  45

Glu Gly Gln Ala Ala Pro Val Asp Gly Glu Ser Trp Val Gly Val Glu
    50                  55                  60

Leu Gly Pro Asp Gly Val Glu Thr Asp Glu Ser Gly Ala Gly Val Asp
65                  70                  75                  80

Asp Arg Pro Val Phe Lys Thr Glu Lys Ile Lys Gly Val Leu Leu His
                85                  90                  95

Pro Tyr Arg Val Leu Ile Phe Val Arg Leu Ile Ala Phe Thr Leu Phe
            100                 105                 110

Val Ile Trp Arg Ile Ser His Lys Asn Pro Asp Thr Met Trp Leu Trp
        115                 120                 125

Val Thr Ser Ile Cys Gly Glu Phe Trp Phe Gly Phe Ser Trp Leu Leu
    130                 135                 140

Asp Gln Leu Pro Lys Leu Asn Pro Ile Asn Arg Ile Pro Asp Leu Ala
145                 150                 155                 160

Val Leu Arg Gln Arg Phe Asp Arg Ala Asp Gly Thr Ser Thr Leu Pro
                165                 170                 175

Gly Leu Asp Ile Phe Val Thr Thr Ala Asp Pro Ile Lys Glu Pro Ile
            180                 185                 190

Leu Ser Thr Ala Asn Ser Val Leu Ser Ile Leu Ala Ala Asp Tyr Pro
        195                 200                 205
```

```
Val Asp Arg Asn Thr Cys Tyr Ile Ser Asp Asp Ser Gly Met Leu Met
    210                 215                 220
Thr Tyr Glu Ala Met Ala Glu Ser Ala Lys Phe Ala Thr Leu Trp Val
225                 230                 235                 240
Pro Phe Cys Arg Lys His Gly Ile Glu Pro Arg Gly Pro Glu Ser Tyr
                245                 250                 255
Phe Glu Leu Lys Ser His Pro Tyr Met Gly Arg Ala His Asp Glu Phe
                260                 265                 270
Val Asn Asp Arg Arg Val Arg Lys Glu Tyr Asp Asp Phe Lys Ala
    275                 280                 285
Lys Ile Asn Ser Leu Glu Thr Asp Ile Gln Gln Arg Asn Asp Leu His
    290                 295                 300
Asn Ala Ala Val Pro Gln Asn Gly Asp Gly Ile Pro Arg Pro Thr Trp
305                 310                 315                 320
Met Ala Asp Gly Val Gln Trp Gln Gly Thr Trp Val Glu Pro Ser Ala
                325                 330                 335
Asn His Arg Lys Gly Asp His Ala Gly Ile Val Leu Val Leu Ile Asp
                340                 345                 350
His Pro Ser His Asp Arg Leu Pro Gly Ala Pro Ala Ser Ala Asp Asn
                355                 360                 365
Ala Leu Asp Phe Ser Gly Val Asp Thr Arg Leu Pro Met Leu Val Tyr
    370                 375                 380
Met Ser Arg Glu Lys Arg Pro Gly His Asn His Gln Lys Lys Ala Gly
385                 390                 395                 400
Ala Met Asn Ala Leu Thr Arg Ala Ser Ala Leu Leu Ser Asn Ala Pro
                405                 410                 415
Phe Ile Leu Asn Leu Asp Cys Asp His Tyr Ile Asn Asn Ser Gln Ala
                420                 425                 430
Leu Arg Ala Gly Ile Cys Phe Met Val Gly Arg Asp Ser Asp Thr Val
    435                 440                 445
Ala Phe Val Gln Phe Pro Gln Arg Phe Glu Gly Val Asp Pro Thr Asp
    450                 455                 460
Leu Tyr Ala Asn His Asn Arg Ile Phe Phe Asp Gly Thr Leu Arg Ala
465                 470                 475                 480
Leu Asp Gly Met Gln Gly Pro Ile Tyr Val Gly Thr Gly Cys Leu Phe
                485                 490                 495
Arg Arg Ile Thr Val Tyr Gly Phe Asp Pro Pro Arg Ile Asn Val Gly
                500                 505                 510
Gly Pro Cys Phe Pro Ala Leu Gly Gly Leu Phe Ala Lys Thr Lys Tyr
                515                 520                 525
Glu Lys Pro Ser Met Glu Met Thr Met Ala Arg Ala Asn Gln Ala Val
    530                 535                 540
Val Pro Ala Met Ala Lys Gly Lys His Gly Phe Leu Pro Leu Pro Lys
545                 550                 555                 560
Lys Thr Tyr Gly Lys Ser Asp Lys Phe Val Asp Thr Ile Pro Arg Ala
                565                 570                 575
Ser His Pro Ser Pro Tyr Ala Ala Glu Gly Ile Arg Val Val Asp Ser
                580                 585                 590
Gly Ala Glu Thr Leu Ala Glu Ala Val Lys Val Thr Gly Ser Ala Phe
    595                 600                 605
Glu Gln Lys Thr Gly Trp Gly Ser Glu Leu Gly Trp Val Tyr Asp Thr
    610                 615                 620
```

Val Thr Glu Asp Val Val Thr Gly Tyr Arg Met His Ile Lys Gly Trp
625                 630                 635                 640

Arg Ser Arg Tyr Cys Ser Ile Tyr Pro His Ala Phe Ile Gly Thr Ala
            645                 650                 655

Pro Ile Asn Leu Thr Glu Arg Leu Phe Gln Val Leu Arg Trp Ser Thr
                660                 665                 670

Gly Ser Leu Glu Ile Phe Phe Ser Lys Asn Asn Pro Leu Phe Gly Ser
            675                 680                 685

Thr Tyr Leu His Pro Leu Gln Arg Val Ala Tyr Ile Asn Ile Thr Thr
690                 695                 700

Tyr Pro Phe Thr Ala Ile Phe Leu Ile Phe Tyr Thr Thr Val Pro Ala
705                 710                 715                 720

Leu Ser Phe Val Thr Gly His Phe Ile Val Gln Arg Pro Thr Thr Met
                725                 730                 735

Phe Tyr Val Tyr Leu Gly Ile Val Leu Ala Thr Leu Leu Ile Ile Ala
            740                 745                 750

Val Leu Glu Val Lys Trp Ala Gly Val Thr Val Phe Glu Trp Phe Arg
            755                 760                 765

Asn Gly Gln Phe Trp Met Thr Ala Ser Cys Ser Ala Tyr Leu Ala Ala
770                 775                 780

Val Cys Gln Val Leu Thr Lys Val Ile Phe Arg Arg Asp Ile Ser Phe
785                 790                 795                 800

Lys Leu Thr Ser Lys Leu Pro Ala Gly Asp Glu Lys Lys Asp Pro Tyr
                805                 810                 815

Ala Asp Leu Tyr Val Val Arg Trp Thr Pro Leu Met Ile Thr Pro Ile
            820                 825                 830

Ile Ile Ile Phe Val Asn Ile Ile Gly Ser Ala Val Ala Phe Ala Lys
            835                 840                 845

Val Leu Asp Gly Glu Trp Thr His Trp Leu Lys Val Ala Gly Gly Val
850                 855                 860

Phe Phe Asn Phe Trp Val Leu Phe His Leu Tyr Pro Phe Ala Lys Gly
865                 870                 875                 880

Leu Leu Gly Lys His Gly Lys Thr Pro Val Val Leu Val Trp Trp
                885                 890                 895

Ala Phe Thr Phe Val Ile Thr Ala Val Leu Tyr Ile Asn Ile Pro His
            900                 905                 910

Ile His Gly Gly Gly Lys His Ser Val Gly His Gly Met His His
            915                 920                 925

Gly Lys Lys Phe Asp Gly Tyr Tyr Leu Trp Pro
930                 935

<210> SEQ ID NO 2
<211> LENGTH: 2820
<212> TYPE: DNA
<213> ORGANISM: Brachypodium distachyon

<400> SEQUENCE: 2
atggcgccag cggtggccgg cgggagcagc cggggtgcag ggtgtaagtg cgggttccag      60
gtgtgcgtgt gctctgggtc ggcggcggtg gcgtcggcgg ttcgtcgct ggaggtggag     120 agagccatgg cggtgacgcc ggtggaaggg caggcggcgc cggtggacgg cgagagctgg     180
gtcggcgtcg agctcggccc cgacggcgtg gagacggacg agagcggcgc cggcgtcgac     240
gaccgccccg tcttcaagac cgagaagatc aaggcgtcc cctccacccc ctacagggtg     300
ctgatctttg ttcgtctgat agcgttcacc ctgttcgtga tctggcgtat ctcgcacaag     360

```
aacccggaca cgatgtggct gtgggtgacc tccatctgcg gcgagttctg gttcggcttc    420
tcctggctgc tggaccagct tccaaagctc aacccgatca accggatccc ggacctcgcc    480
gtgctccggc aacgcttcga ccgcgccgac gggacatcca cattgccggg cctcgacatc    540
ttcgtcacca cggccgaccc catcaaggaa cccatcctgt cgacggccaa ctccgtgctc    600
tccatcctgg ccgccgacta cccggtggac cgcaacacct gctacatctc cgacgacagc    660
ggcatgctca tgacctacga ggccatggcg gagtcggcca agttcgccac cctctgggtg    720
ccattctgcc gcaagcacgg catcgaacca cgcgggccgg agagctactt cgagctcaag    780
tcgcacccgt acatggggag agcgcacgac gagttcgtca tgaccgccg ccgggtgcgc    840 aaggagtatg atgacttcaa ggccaagatt aactctctgg agactgatat ccagcagagg    900
aatgatctgc ataacgctgc cgtgccgcag aatggggatg ggatcccag cctacctgg    960 atggctgatg agtccagtg gcaggggact tgggtcgagc cgtccgctaa tcaccgcaag   1020
ggagaccacg ccggcatcgt cctggttctg attgaccacc cgagccacga ccgccttccc   1080
ggcgcgccgg cgagcgccga caacgcgctg gacttcagcg gcgtggacac ccgcctcccg   1140
atgctcgtct acatgtcccg cgagaagcgc ccaggccaca accaccagaa gaaggccggc   1200
gccatgaacg cgctcaccag ggcttccgcg ctgctctcca acgcgcccct catcctcaac   1260
ctcgactgcg accactacat caacaactcc caggccctcc gcgccgggat ctgcttcatg   1320
gtcggccggg acagcgacac cgtcgccttc gtgcagttcc cgcagcggtt cgagggcgtc   1380
gaccccacgg acctctacgc caaccacaac cgcatcttct tcgacggcac cctcagggcg   1440
ctcgacggaa tgcaaggccc gatctatgtc ggcacgggat gcctcttccg gcgcatcacc   1500
gtctacggct tcgacccgcc caggatcaac gtcggcgggc catgcttccc tgctctcggt   1560
ggcctgttcg ccaagaccaa gtatgagaag cccagcatgg agatgaccat ggcgagagcc   1620
aaccaggccg tggtgccggc catggccaag gggaagcacg gcttcctgcc gctccccaag   1680
aagacgtacg ggaagtccga caagttcgtg gacaccatcc cgcgcgcgtc ccacccgtcg   1740
ccgtacgcgg cggaggggat ccgcgtggtg gactccggcg cggagactct ggctgaggcc   1800
gtcaaggtga ccggatcggc attcgagcag aagaccggat ggggcagcga gctcggctgg   1860
gtctacgaca ctgtcacaga ggacgtggtg actggctaca ggatgcacat caagggctgg   1920
aggtcccgct actgctccat ctacccgcac gccttcatcg caccgcccc gatcaacctc   1980 acggagcggc tcttccaggt gctccgctgg tccaccggct ccctcgagat cttcttctcc   2040
aagaacaacc cgctcttcgg cagcacctac ctgcacccgc tccagcgcgt cgcctacatc   2100
aacatcacca catacccgtt caccgccatc ttcctcatct tctacaccac cgtgccggcg   2160
ctctccttcg tcaccggcca cttcatcgtg cagcgcccga cgaccatgtt ctacgtctac   2220
ctggggatcg tgctggcgac gctgctcatc atcgctgttc ttgaggtcaa gtgggctgga   2280
gtgacagtgt tcgagtggtt caggaacggg cagttctgga tgacggctag ctgctccgcc   2340
taccttgctg ctgtgtgcca ggtgctcacc aaggtgatct tcaggaggga catctcattc   2400
aagctcactt ccaagctgcc tgctggggac gagaagaagg accctatgc cgatctgtac   2460 gtggtgcgtt ggactccact catgatcact ccaatcatca tcatcttcgt caacatcatc   2520
ggctcggcgg tggccttcgc caaggtgctg gacggcgagt ggacgcactg gctcaaggtg   2580 gcggaggag tcttcttcaa cttctgggtg ctgttccacc tctacccgtt cgccaagggt   2640
ctcctgggga agcatggcaa gaccccgtc gtcgtgctcg tctggtgggc attcaccttc   2700
```

| | |
|---|---:|
| gtcatcaccg ccgtcctcta catcaacatc ccgcacatcc atggaggagg aggcaagcac | 2760 |
| agcgtggggc atgggatgca ccatggcaag aagttcgacg gctactacct ctggccgtga | 2820 |

<210> SEQ ID NO 3
<211> LENGTH: 2820
<212> TYPE: DNA
<213> ORGANISM: Artificial Sequence
<220> FEATURE:
<223> OTHER INFORMATION: A synthetic oligonucleotide sequence

<400> SEQUENCE: 3

| | |
|---|---:|
| atggctccag ctgttgctgg cggctcctct aggggcgctg gctgcaagtg cggcttccag | 60 |
| gtgtgcgtgt gctccggctc tgccgccgtg gcctccgccg gctcatccct cgaggtcgag | 120 |
| agggccatgg ctgttacccc agttgagggc caggccgctc cagtggacgg cgagtcctgg | 180 |
| gtgggcgttg agcttggccc agacggcgtc gagaccgacg agtccggcgc tggcgtggac | 240 |
| gacaggccag tgttcaagac cgagaagatc aagggcgtgc tcctccaccc atacagggtg | 300 |
| ctcatcttcg tgaggctgat cgccttcacc ctcttcgtga tctggcgcat ctcccacaag | 360 |
| aacccggaca ccatgtggct ctgggtgacc tctatttgcg gcgagttctg gttcggcttc | 420 |
| tcctggctcc tcgaccagct cccaaagctc aacccgatca accgcatccc agatctcgcc | 480 |
| gttctcaggc agaggttcga tagggccgac ggcacctcca ccctcccagg ccttgatatt | 540 |
| ttcgtgacca ccgccgaccc catcaaggag ccaattctct caaccgccaa ctccgtgctc | 600 |
| tctatcctcg ccgccgatta cccggtggat aggaacacgt gctacatctc gacgacagc | 660 |
| ggcatgctca tgacctacga ggctatggcc gagtccgcca agttcgctac cctctgggtg | 720 |
| ccattctgcc gcaagcacgg catcgagcca aggggcccag agtcctactt cgagcttaag | 780 |
| tcccacccgt acatgggcag ggcccatgac gagttcgtga acgataggcg cagggtgagg | 840 |
| aaggagtacg acgacttcaa ggccaagatc aactccctcg agacggacat ccagcagagg | 900 |
| aacgacctcc ataacgccgc cgtgccacag aacggggacg gcatcccaag gccaacctgg | 960 |
| atggccgatg gcgtgcagtg gcagggcacc tgggttgagc catctgccaa ccataggaag | 1020 |
| ggcgatcacg ccggcattgt gctcgtgctc atcgaccatc catcccacga caggctccca | 1080 |
| ggcgccccag cctctgccga caacgccctc gacttctccg gcgtggacac caggcttcca | 1140 |
| atgctcgttt acatgtcccg cgagaagagg ccaggccaca accaccagaa gaaggctggc | 1200 |
| gctatgaacg cccttaccag ggcttctgct ctcctctcca cgccccgtt catcctcaac | 1260 |
| ctcgactgcg accactacat caacaacagc caggctctca gggccggcat ctgcttcatg | 1320 |
| gtgggcaggg attctgacac cgtggccttc gttcagttcc cgcagcgctt cgagggggtt | 1380 |
| gacccaaccg atctctacgc caaccacaac aggattttct tcgatggcac cctcagggcc | 1440 |
| ctcgatggca tgcagggccc tatctacgtg ggcaccggct gcctcttcag gcgcatcacc | 1500 |
| gtgtacggct tcgacccgcc aaggattaac gttggcggcc catgcttccc agctctcggc | 1560 |
| ggcctcttcg ctaagaccaa gtacgagaag cccagcatgg agatgaccat ggccagggcc | 1620 |
| aaccaggccg ttgttccagc tatggctaag gggaagcacg gcttcctgcc actcccgaag | 1680 |
| aagacctacg gcaagagcga caagttcgtc gacaccattc aagggcctc ccacccatct | 1740 |
| ccatacgctg ccgagggcat tagggttgtg gactctggcg ccgagaccct cgccgaggcc | 1800 |
| gtgaaggtga ccggctccgc cttcgagcag aagaccggct ggggctccga gcttggctgg | 1860 |
| gtttacgaca ccgtgaccga ggatgtggtc accggctaca ggatgcacat taagggctgg | 1920 |
| cgcagcaggt actgctccat ctacccacat gccttcatcg gcaccgcccc cattaacctc | 1980 |

| | |
|---|---|
| accgagaggc tttttccaggt gctcaggtgg tctaccggca gcctcgagat cttcttcagc | 2040 |
| aagaacaacc cgctgttcgg ctccacctac ctgcatccac tccagagggt ggcctacatt | 2100 |
| aacatcacca cctacccgtt caccgccatc ttcctcatct tctacacgac cgtgcccgcc | 2160 |
| ctctcattcg tgaccggcca tttcattgtg cagaggccga ccaccatgtt ctacgtgtac | 2220 |
| ctcgggatcg tgctcgccac cctcctcatt attgccgtgc tcgaggttaa gtgggctggc | 2280 |
| gtgaccgtgt tcgagtggtt ccgcaacggc cagttctgga tgaccgcctc ttgctctgct | 2340 |
| tacctcgccg ctgtttgcca ggtcctcacc aaggttatct tccgcaggga catctccttc | 2400 |
| aagctcacct ccaagctccc agccggcgac gagaagaagg acccatacgc cgatctgtac | 2460 |
| gtggtgaggt ggaccccgct catgatcacc ccgatcatca tcattttcgt caacatcatc | 2520 |
| ggctccgcgg tcgccttcgc caaggtgctc gatggcgagt ggacccattg gcttaaggtc | 2580 |
| gccggcggcg tgttcttcaa cttctgggtt ctcttccacc tctacccttt cgcgaagggc | 2640 |
| cttcttggca agcacggcaa gaccccagtg gtggttcttg tctggtgggc cttcaccttc | 2700 |
| gtcatcaccg ccgtgctgta catcaacatc ccgcacatcc atggcggcgg cggcaagcac | 2760 |
| tccgtgggcc acggcatgca ccatggcaag aagttcgacg gctactacct ctggccgtga | 2820 |

<210> SEQ ID NO 4
<211> LENGTH: 3642
<212> TYPE: DNA
<213> ORGANISM: Artificial Sequence
<220> FEATURE:
<223> OTHER INFORMATION: A synthetic oligonucleotide sequence

<400> SEQUENCE: 4

| | |
|---|---|
| atgggcaagg gcgaggagct gttcaccggg gtggtgccca tcctggtcga gctggacggc | 60 |
| gacgtaaacg gccacaagtt cagcgtgtcc ggcgagggcg agggcgatgc cacctacggc | 120 |
| aagctgaccc tgaagttcat ctgcaccacc ggcaagctgc ccgtgccctg gcccaccctc | 180 |
| gtgaccacct tcggctacgg cctgcagtgc ttcgcccgct accccgacca catgaagcag | 240 |
| cacgacttct tcaagtccgc catgcccgaa ggctacgtcc aggagcgcac catcttcttc | 300 |
| aaggacgacg gcaactacaa gacccgcgcc gaggtgaagt tcgagggcga cacccctggtg | 360 |
| aaccgcatcg agctgaaggg catcgacttc aaggaggacg gcaacatcct ggggcacaag | 420 |
| ctggagtaca actacaacag ccacaacgtc tatatcatgg ccgacaagca gaagaacggc | 480 |
| atcaaggtga acttcaagat ccgccacaac atcgaggacg gcagcgtgca gctcgccgac | 540 |
| cactaccagc agaacacccc catcggcgac ggccccgtgc tgctgcccga caaccactac | 600 |
| ctgagctacc agtccgccct gagcaaagac cccaacgaga agcgcgatca catggtcctg | 660 |
| ctggagttcg tgaccgccgc cgggatcact ctcggcatgg acgagctgta caagtccgga | 720 |
| ctcagatctc gagctcaagc ttcgaattct gcagtcgacg gtaccgcggg cccgggatca | 780 |
| tcaacaagtt tgtacaaaaa agcaggctcc gaattcgccc ttatggctcc agctgttgct | 840 |
| ggcggctcct ctagggcgc tggctgcaag tgcggcttcc aggtgtgcgt gtgctccggc | 900 |
| tctgccgccg tggcctccgc cggctcatcc ctcgaggtcg agagggccat ggctgttacc | 960 |
| ccagttgagg gccaggccgc tccagtggac ggcgagtcct gggtgggcgt tgagcttggc | 1020 |
| ccagacggcg tcgagaccga cgagtccggc gctggcgtgg acgacaggcc agtgttcaag | 1080 |
| accgagaaga tcaagggcgt gctcctccac ccatacaggg tgctcatctt cgtgaggctg | 1140 |
| atcgccttca ccctcttcgt gatctggcgc atctcccaca gaacccgga caccatgtgg | 1200 |

```
ctctgggtga cctctatttg cggcgagttc tggttcggct tctcctggct cctcgaccag    1260
ctcccaaagc tcaacccgat caaccgcatc ccagatctcg ccgttctcag gcagaggttc    1320
gatagggccg acggcacctc caccctccca ggccttgata ttttcgtgac caccgccgac    1380
cccatcaagg agccaattct ctcaaccgcc aactccgtgc tctctatcct cgccgccgat    1440
tacccggtgg ataggaacac gtgctacatc tccgacgaca gcggcatgct catgacctac    1500
gaggctatgg ccgagtccgc caagttcgct accctctggg tgccattctg ccgcaagcac    1560
ggcatcgagc caaggggccc agagtcctac ttcgagctta agtcccaccc gtacatgggc    1620
agggcccatg acgagttcgt gaacgatagg cgcagggtga ggaaggagta cgacgacttc    1680
aaggccaaga tcaactccct cgagacggac atccagcaga ggaacgacct ccataacgcc    1740
gccgtgccac agaacgggga cggcatccca aggccaacct ggatggccga tggcgtgcag    1800
tggcagggca cctgggttga gccatctgcc aaccatagga agggcgatca cgccggcatt    1860
gtgctcgtgc tcatcgacca tccatcccac gacaggctcc caggcgcccc agcctctgcc    1920
gacaacgccc tcgacttctc cggcgtggac accaggcttc caatgctcgt ttacatgtcc    1980
cgcgagaaga ggccaggcca caaccaccag aagaaggctg gcgctatgaa cgcccttacc    2040
agggcttctg ctctcctctc caacgccccg ttcatcctca acctcgactg cgaccactac    2100
atcaacaaca gccaggctct cagggccggc atctgcttca tggtgggcag ggattctgac    2160
accgtggcct tcgttcagtt cccgcagcgc ttcgaggggg ttgacccaac cgatctctac    2220
gccaaccaca acaggatttt cttcgatggc accctcaggg ccctcgatgg catgcagggc    2280
cctatctacg tgggcaccgg ctgcctcttc aggcgcatca ccgtgtacgg cttcgacccg    2340
ccaaggatta acgttggcgg cccatgcttc ccagctctcg gcggcctctt cgctaagacc    2400
aagtacgaga agcccagcat ggagatgacc atggccaggg ccaaccaggc cgttgttcca    2460
gctatggcta aggggaagca cggcttcctg ccactcccga gaagaccta cggcaagagc    2520 gacaagttcg tcgacaccat tccaagggcc tcccacccat ctccatacgc tgccgagggc    2580
attagggttg tggactctgg cgccgagacc ctcgccgagg ccgtgaaggt gaccggctcc    2640
gccttcgagc agaagaccgg ctggggctcc gagcttggct gggtttacga caccgtgacc    2700
gaggatgtgg tcaccggcta caggatgcac attaagggct ggcgcagcag gtactgctcc    2760
atctacccac atgccttcat cggcaccgcc cccattaacc tcaccgagag gcttttccag    2820
gtgctcaggt ggtctaccgg cagcctcgag atcttcttca gcaagaacaa cccgctgttc    2880
ggctccacct acctgcatcc actccagagg gtggcctaca ttaacatcac cacctacccg    2940
ttcaccgcca tcttcctcat cttctacacg accgtgcccg ccctctcatt cgtgaccggc    3000
catttcattg tgcagaggcc gaccaccatg ttctacgtgt acctcgggat cgtgctcgcc    3060
accctcctca ttattgccgt gctcgaggtt aagtgggctg gcgtgaccgt gttcgagtgg    3120
ttccgcaacg gccagttctg gatgaccgcc tcttgctctg cttacctcgc cgctgtttgc    3180
caggtcctca ccaaggttat cttccgcagg gacatctcct tcaagctcac ctccaagctc    3240
ccagccggcg acgagaagaa ggacccatac gccgatctgt acgtggtgag gtggaccccg    3300
ctcatgatca cccgatcat catcattttc gtcaacatca tcggctccgc ggtcgccttc    3360
gccaaggtgc tcgatggcga gtggacccat tggcttaagg tcgccggcgg cgtgttcttc    3420
aacttctggg ttctcttcca cctctaccct ttcgcgaagg gccttcttgg caagcacggc    3480
aagaccccag tggtggttct tgtctggtgg gccttcacct tcgtcatcac cgccgtgctc    3540
tacatcaaca tcccgcacat ccatggcggc ggcggcaagc actccgtggg ccacggcatg    3600
```
caccatggca agaagttcga cggctactac ctctggccgt ga    3642

<210> SEQ ID NO 5
<211> LENGTH: 944
<212> TYPE: PRT
<213> ORGANISM: Triticum aestivum

<400> SEQUENCE: 5

```
Met Ala Pro Ala Val Ala Gly Gly Arg Val Arg Ser Asn Glu Pro
1               5                   10                  15

Ala Ala Ala Ala Thr Ala Pro Ala Ser Gly Lys Pro Cys Val Cys Gly
            20                  25                  30

Phe Gln Val Cys Ala Cys Thr Gly Ser Ala Ala Val Ala Ser Ala Ala
            35                  40                  45

Ser Ser Leu Asp Met Asp Ile Val Ala Met Gly Gln Ile Gly Ala Val
    50                  55                  60

Asn Asp Glu Ser Trp Val Gly Val Glu Leu Gly Glu Asp Gly Glu Thr
65              70                  75                  80

Asp Glu Ser Gly Ala Ala Val Asp Asp Arg Pro Val Phe Arg Thr Glu
                85                  90                  95

Lys Ile Lys Gly Val Leu Leu His Pro Tyr Arg Val Leu Ile Phe Val
            100                 105                 110

Arg Leu Ile Ala Phe Thr Leu Phe Val Ile Trp Arg Ile Ser His Lys
            115                 120                 125

Asn Pro Asp Ala Met Trp Leu Trp Val Thr Ser Ile Cys Gly Glu Phe
    130                 135                 140

Trp Phe Gly Phe Ser Trp Leu Leu Asp Gln Leu Pro Lys Leu Asn Pro
145             150                 155                 160

Ile Asn Arg Val Pro Asp Leu Ala Val Leu Arg Gln Arg Phe Asp Arg
                165                 170                 175

Pro Asp Gly Thr Ser Thr Leu Pro Gly Leu Asp Ile Phe Val Thr Thr
            180                 185                 190

Ala Asp Pro Ile Lys Glu Pro Ile Leu Ser Thr Ala Asn Ser Val Leu
            195                 200                 205

Ser Ile Leu Ala Ala Asp Tyr Pro Val Asp Arg Asn Thr Cys Tyr Val
    210                 215                 220

Ser Asp Asp Ser Gly Met Leu Leu Thr Tyr Glu Ala Leu Ala Glu Ser
225             230                 235                 240

Ser Lys Phe Ala Thr Leu Trp Val Pro Phe Cys Arg Lys His Gly Ile
                245                 250                 255

Glu Pro Arg Gly Pro Glu Ser Tyr Phe Glu Leu Lys Ser His Pro Tyr
            260                 265                 270

Met Gly Arg Ala Gln Asp Glu Phe Val Asn Asp Arg Arg Val Arg
            275                 280                 285

Lys Glu Tyr Asp Glu Phe Lys Ala Arg Ile Asn Ser Leu Glu His Asp
    290                 295                 300

Ile Lys Gln Arg Asn Asp Gly Tyr Asn Ala Ala Asn Ala His Arg Glu
305             310                 315                 320

Gly Glu Pro Arg Pro Thr Trp Met Ala Asp Gly Thr Gln Trp Glu Gly
                325                 330                 335

Thr Trp Val Asp Ala Ser Glu Asn His Arg Gly Asp His Ala Gly
            340                 345                 350

Ile Val Leu Val Leu Leu Asn His Pro Ser His Arg Arg Gln Thr Gly
    355                 360                 365
```

```
Pro Pro Ala Ser Ala Asp Asn Pro Leu Asp Phe Ser Gly Val Asp Val
    370                 375                 380

Arg Leu Pro Met Leu Val Tyr Met Ser Arg Glu Lys Arg Pro Gly His
385                 390                 395                 400

Asp His Gln Lys Lys Ala Gly Ala Met Asn Ala Leu Thr Arg Ala Ser
                    405                 410                 415

Ala Leu Leu Ser Asn Ser Pro Phe Ile Leu Asn Leu Asp Cys Asn His
            420                 425                 430

Tyr Ile Asn Asn Ser Gln Ala Leu Arg Ala Gly Ile Cys Phe Met Val
        435                 440                 445

Gly Arg Asp Ser Asp Thr Val Ala Phe Val Gln Phe Pro Gln Arg Phe
    450                 455                 460

Glu Gly Val Asp Pro Thr Asp Leu Tyr Ala Asn His Asn Arg Ile Phe
465                 470                 475                 480

Phe Asp Gly Thr Leu Arg Ala Leu Asp Gly Met Gln Gly Pro Ile Tyr
            485                 490                 495

Val Gly Thr Gly Cys Leu Phe Arg Arg Ile Thr Val Tyr Gly Phe Asp
        500                 505                 510

Pro Pro Arg Ile Asn Val Gly Gly Pro Cys Phe Pro Arg Leu Ala Gly
    515                 520                 525

Leu Phe Ala Lys Thr Lys Tyr Glu Lys Pro Gly Leu Glu Met Thr Met
530                 535                 540

Ala Lys Ala Lys Ala Ala Pro Val Pro Ala Lys Gly Lys His Gly Phe
545                 550                 555                 560

Leu Pro Leu Pro Lys Lys Thr Tyr Gly Lys Ser Asp Ala Phe Val Asp
            565                 570                 575

Ser Ile Pro Arg Ala Ser His Pro Ser Pro Tyr Ala Ala Ala Ala Glu
        580                 585                 590

Gly Ile Val Ala Asp Glu Ala Thr Ile Val Glu Ala Val Asn Val Thr
    595                 600                 605

Ala Ala Ala Phe Glu Lys Lys Thr Gly Trp Gly Lys Glu Ile Gly Trp
610                 615                 620

Val Tyr Asp Thr Val Thr Glu Asp Val Val Thr Gly Tyr Arg Met His
625                 630                 635                 640

Ile Lys Gly Trp Arg Ser Arg Tyr Cys Ser Ile Tyr Pro His Ala Phe
            645                 650                 655

Ile Gly Thr Ala Pro Ile Asn Leu Thr Glu Arg Leu Phe Gln Val Leu
        660                 665                 670

Arg Trp Ser Thr Gly Ser Leu Glu Ile Phe Phe Ser Lys Asn Asn Pro
    675                 680                 685

Leu Phe Gly Ser Thr Tyr Leu His Pro Leu Gln Arg Val Ala Tyr Ile
    690                 695                 700

Asn Ile Thr Thr Tyr Pro Phe Thr Ala Ile Phe Leu Ile Phe Tyr Thr
705                 710                 715                 720

Thr Val Pro Ala Leu Ser Phe Val Thr Gly His Phe Ile Val Gln Arg
            725                 730                 735

Pro Thr Thr Met Phe Tyr Val Tyr Leu Gly Ile Val Leu Ser Thr Leu
        740                 745                 750

Leu Val Ile Ala Val Leu Glu Val Lys Trp Ala Gly Val Thr Val Phe
    755                 760                 765

Glu Trp Phe Arg Asn Gly Gln Phe Trp Met Thr Ala Ser Cys Ser Ala
770                 775                 780
```

```
Tyr Leu Ala Ala Val Cys Gln Val Leu Thr Lys Val Ile Phe Arg Arg
785                 790                 795                 800

Asp Ile Ser Phe Lys Leu Thr Ser Lys Leu Pro Ser Gly Asp Glu Lys
            805                 810                 815

Lys Asp Pro Tyr Ala Asp Leu Tyr Val Val Arg Trp Thr Pro Leu Met
            820                 825                 830

Ile Thr Pro Ile Ile Ile Ile Phe Val Asn Ile Ile Gly Ser Ala Val
            835                 840                 845

Ala Phe Ala Lys Val Leu Asp Gly Glu Trp Thr His Trp Leu Lys Val
            850                 855                 860

Ala Gly Gly Val Phe Phe Asn Phe Trp Val Leu Phe His Leu Tyr Pro
865                 870                 875                 880

Phe Ala Lys Gly Ile Leu Gly Lys His Gly Lys Thr Pro Val Val Val
            885                 890                 895

Leu Val Trp Trp Ala Phe Thr Phe Val Ile Thr Ala Val Phe Tyr Ile
            900                 905                 910

Asn Ile Pro His Met His Ser Ser Gly Gly Lys His Thr Thr Val His
            915                 920                 925

Gly His His Gly Lys Lys Phe Val Asp Ala Gly Tyr Tyr Asn Trp Pro
            930                 935                 940
```

```
<210> SEQ ID NO 6
<211> LENGTH: 947
<212> TYPE: PRT
<213> ORGANISM: Hordeum vulgare

<400> SEQUENCE: 6

Met Ala Pro Ala Val Ala Gly Gly Gly Arg Val Arg Ser Asn Glu Pro
1               5                   10                  15

Val Ala Ala Ala Ala Ala Pro Ala Ala Ser Gly Lys Pro Cys Val
            20                  25                  30

Cys Gly Phe Gln Val Cys Ala Cys Thr Gly Ser Ala Ala Val Ala Ser
            35                  40                  45

Ala Ala Ser Ser Leu Asp Met Asp Ile Val Ala Met Gly Gln Ile Gly
            50                  55                  60

Ala Val Asn Asp Glu Ser Trp Val Gly Val Glu Leu Gly Glu Asp Gly
65                  70                  75                  80

Glu Thr Asp Glu Ser Gly Ala Ala Val Asp Asp Arg Pro Val Phe Arg
                85                  90                  95

Thr Glu Lys Ile Lys Gly Val Leu Leu His Pro Tyr Arg Val Leu Ile
            100                 105                 110

Phe Val Arg Leu Ile Ala Phe Thr Leu Phe Val Ile Trp Arg Ile Ser
            115                 120                 125

His Lys Asn Pro Asp Ala Met Trp Leu Trp Val Thr Ser Ile Cys Gly
            130                 135                 140

Glu Phe Trp Phe Gly Phe Ser Trp Leu Leu Asp Gln Leu Pro Lys Leu
145                 150                 155                 160

Asn Pro Ile Asn Arg Val Pro Asp Leu Ala Val Leu Arg Gln Arg Phe
                165                 170                 175

Asp Arg Pro Asp Gly Thr Ser Thr Leu Pro Gly Leu Asp Ile Phe Val
            180                 185                 190

Thr Thr Ala Asp Pro Ile Lys Glu Pro Ile Leu Ser Thr Ala Asn Ser
            195                 200                 205

Val Leu Ser Ile Leu Ala Ala Asp Tyr Pro Val Asp Arg Asn Thr Cys
            210                 215                 220
```

```
Tyr Val Ser Asp Asp Ser Gly Met Leu Leu Thr Tyr Glu Ala Leu Ala
225                 230                 235                 240

Glu Ser Ser Lys Phe Ala Thr Leu Trp Val Pro Phe Cys Arg Lys His
            245                 250                 255

Gly Ile Glu Pro Arg Gly Pro Glu Ser Tyr Phe Glu Leu Lys Ser His
                260                 265                 270

Pro Tyr Met Gly Arg Ala Gln Asp Glu Phe Val Asn Asp Arg Arg Arg
            275                 280                 285

Val Arg Lys Glu Tyr Asp Glu Phe Lys Ala Arg Ile Asn Ser Leu Glu
        290                 295                 300

His Asp Ile Lys Gln Arg Asn Asp Gly Tyr Asn Ala Ala Ile Ala His
305                 310                 315                 320

Ser Gln Gly Val Pro Arg Pro Thr Trp Met Ala Asp Gly Thr Gln Trp
                325                 330                 335

Glu Gly Thr Trp Val Asp Ala Ser Glu Asn His Arg Arg Gly Asp His
            340                 345                 350

Ala Gly Ile Val Leu Val Leu Asn His Pro Ser His Arg Arg Gln
                355                 360                 365

Thr Gly Pro Pro Ala Ser Ala Asp Asn Pro Leu Asp Leu Ser Gly Val
370                 375                 380

Asp Val Arg Leu Pro Met Leu Val Tyr Val Ser Arg Glu Lys Arg Pro
385                 390                 395                 400

Gly His Asp His Gln Lys Lys Ala Gly Ala Met Asn Ala Leu Thr Arg
            405                 410                 415

Ala Ser Ala Leu Leu Ser Asn Ser Pro Phe Ile Leu Asn Leu Asp Cys
                420                 425                 430

Asp His Tyr Ile Asn Asn Ser Gln Ala Leu Arg Ala Gly Ile Cys Phe
            435                 440                 445

Met Val Gly Arg Asp Ser Asp Thr Val Ala Phe Val Gln Phe Pro Gln
        450                 455                 460

Arg Phe Glu Gly Val Asp Pro Thr Asp Leu Tyr Ala Asn His Asn Arg
465                 470                 475                 480

Ile Phe Phe Asp Gly Thr Leu Arg Ala Leu Asp Gly Met Gln Gly Pro
                485                 490                 495

Ile Tyr Val Gly Thr Gly Cys Leu Phe Arg Arg Ile Thr Val Tyr Gly
            500                 505                 510

Phe Asp Pro Pro Arg Ile Asn Val Gly Gly Pro Cys Phe Pro Arg Leu
            515                 520                 525

Ala Gly Leu Phe Ala Lys Thr Lys Tyr Glu Lys Pro Gly Leu Glu Met
530                 535                 540

Thr Thr Ala Lys Ala Lys Ala Ala Pro Val Pro Ala Lys Gly Lys His
545                 550                 555                 560

Gly Phe Leu Pro Leu Pro Lys Lys Thr Tyr Gly Lys Ser Asp Ala Phe
                565                 570                 575

Val Asp Thr Ile Pro Arg Ala Ser His Pro Ser Pro Tyr Ala Ala Ala
            580                 585                 590

Ala Glu Gly Ile Val Ala Asp Glu Ala Thr Ile Val Glu Ala Val Asn
            595                 600                 605

Val Thr Ala Ala Ala Phe Glu Lys Lys Thr Gly Trp Gly Lys Glu Ile
        610                 615                 620

Gly Trp Val Tyr Asp Thr Val Thr Glu Asp Val Val Thr Gly Tyr Arg
625                 630                 635                 640
```

Met His Ile Lys Gly Trp Arg Ser Arg Tyr Cys Ser Ile Tyr Pro His
                645                 650                 655

Ala Phe Ile Gly Thr Ala Pro Ile Asn Leu Thr Glu Arg Leu Phe Gln
            660                 665                 670

Val Leu Arg Trp Ser Thr Gly Ser Leu Glu Ile Phe Phe Ser Lys Asn
        675                 680                 685

Asn Pro Leu Phe Gly Ser Thr Tyr Leu His Pro Leu Gln Arg Val Ala
    690                 695                 700

Tyr Ile Asn Ile Thr Thr Tyr Pro Phe Thr Ala Ile Phe Leu Ile Phe
705                 710                 715                 720

Tyr Thr Thr Val Pro Ala Leu Ser Phe Val Thr Gly His Phe Ile Val
                725                 730                 735

Gln Arg Pro Thr Thr Met Phe Tyr Val Tyr Leu Gly Ile Val Leu Ser
            740                 745                 750

Thr Leu Leu Val Ile Ala Val Leu Glu Val Lys Trp Ala Gly Val Thr
        755                 760                 765

Val Phe Glu Trp Phe Arg Asn Gly Gln Phe Trp Met Thr Ala Ser Cys
    770                 775                 780

Ser Ala Tyr Leu Ala Ala Val Cys Gln Val Leu Thr Lys Val Ile Phe
785                 790                 795                 800

Arg Arg Asp Ile Ser Phe Lys Leu Thr Ser Lys Leu Pro Ser Gly Asp
                805                 810                 815

Glu Lys Lys Asp Pro Tyr Ala Asp Leu Tyr Val Val Arg Trp Thr Pro
            820                 825                 830

Leu Met Ile Thr Pro Ile Ile Ile Phe Val Asn Ile Ile Gly Ser
        835                 840                 845

Ala Val Ala Phe Ala Lys Val Leu Asp Gly Glu Trp Thr His Trp Leu
    850                 855                 860

Lys Val Ala Gly Gly Val Phe Phe Asn Phe Trp Val Leu Phe His Leu
865                 870                 875                 880

Tyr Pro Phe Ala Lys Gly Ile Leu Gly Lys His Gly Lys Thr Pro Val
                885                 890                 895

Val Val Leu Val Trp Trp Ala Phe Thr Phe Val Ile Thr Ala Val Leu
            900                 905                 910

Tyr Ile Asn Ile Pro His Met His Thr Ser Gly Gly Lys His Thr Thr
        915                 920                 925

Val His Gly His His Gly Lys Lys Leu Val Asp Thr Gly Leu Tyr Gly
    930                 935                 940

Trp Leu His
945

<210> SEQ ID NO 7
<211> LENGTH: 945
<212> TYPE: PRT
<213> ORGANISM: Zea mays

<400> SEQUENCE: 7

Met Ala Ala Gly Gln Gln Gln Ala Ser Gly Gly Ala Lys His Gly Cys
1               5                   10                  15

Val Cys Gly Phe Pro Val Cys Ala Cys Ala Gly Ala Ala Ala Val Ala
            20                  25                  30

Ser Ala Ala Ser Ser Ala Asp Met Asp Arg Val Ala Val Ala Ala Thr
        35                  40                  45

Glu Gly Gln Ile Gly Ala Val Asn Asp Glu Ser Trp Ile Ala Val Asp
    50                  55                  60

```
Leu Ser Asp Asp Gly Leu Ser Ala Asp Gly Ala Asp Pro Gly Val Ala
 65                  70                  75                  80

Leu Glu Asp Arg Pro Val Phe Arg Thr Glu Lys Ile Lys Gly Val Leu
                 85                  90                  95

Leu His Pro Tyr Arg Val Leu Ile Phe Val Arg Leu Ile Ala Phe Thr
            100                 105                 110

Leu Phe Val Ile Trp Arg Ile Ser His Arg Asn Pro Asp Ala Leu Trp
        115                 120                 125

Leu Trp Val Thr Ser Ile Ala Gly Glu Phe Trp Phe Gly Phe Ser Trp
    130                 135                 140

Leu Leu Asp Gln Leu Pro Lys Leu Asn Pro Ile Asn Arg Val Pro Asp
145                 150                 155                 160

Leu Ala Ala Leu Arg Gln Arg Phe Asp Arg Ala Gly Gly Gly Ala Gly
                165                 170                 175

Gly Gly Thr Ser Leu Leu Pro Gly Leu Asp Val Phe Val Thr Thr Ala
            180                 185                 190

Asp Pro Phe Lys Glu Pro Ile Leu Ser Thr Ala Asn Ser Val Leu Ser
        195                 200                 205

Ile Leu Ala Ala Asp Tyr Pro Val Glu Arg Asn Thr Cys Tyr Leu Ser
    210                 215                 220

Asp Asp Ser Gly Met Leu Leu Thr Tyr Glu Ala Met Ala Glu Ala Ala
225                 230                 235                 240

Lys Phe Ala Thr Val Trp Val Pro Phe Cys Arg Lys His Gly Ile Glu
                245                 250                 255

Pro Arg Gly Pro Glu Ser Tyr Phe Asp Leu Lys Ser His Pro Tyr Met
            260                 265                 270

Gly Arg Ser Gln Glu Asp Phe Val Asn Asp Arg Arg Val Arg Lys
        275                 280                 285

Asp Tyr Asp Glu Phe Lys Ala Arg Ile Asn Gly Leu Asp His Asp Ile
    290                 295                 300

Lys Gln Arg Ser Asp Ala Tyr Asn Ala Ala Arg Gly Leu Lys Asp Gly
305                 310                 315                 320

Glu Pro Arg Ala Thr Trp Met Ala Asp Gly Thr Gln Trp Glu Gly Thr
                325                 330                 335

Trp Val Glu Pro Ser Glu Asn His Arg Lys Gly Asp His Ala Gly Ile
            340                 345                 350

Val Leu Val Leu Leu Asn His Pro Ser His Ser Arg Gln Leu Gly Pro
        355                 360                 365

Pro Ala Ser Ala Asp Asn Pro Leu Asp Leu Ser Met Val Asp Val Arg
    370                 375                 380

Leu Pro Met Leu Val Tyr Val Ser Arg Glu Lys Arg Pro Gly His Asn
385                 390                 395                 400

His Gln Lys Lys Ala Gly Ala Met Asn Ala Leu Thr Arg Cys Ser Ala
                405                 410                 415

Val Leu Ser Asn Ser Pro Phe Ile Leu Asn Leu Asp Cys Asp His Tyr
            420                 425                 430

Ile Asn Asn Ser Gln Ala Leu Arg Ala Gly Ile Cys Phe Met Leu Gly
        435                 440                 445

Arg Asp Ser Asp Thr Val Ala Phe Val Gln Phe Pro Gln Arg Phe Glu
    450                 455                 460

Gly Val Asp Pro Thr Asp Leu Tyr Ala Asn His Asn Arg Ile Phe Phe
465                 470                 475                 480
```

```
Asp Gly Thr Leu Arg Ala Leu Asp Gly Met Gln Gly Pro Ile Tyr Val
                485                 490                 495
Gly Thr Gly Cys Leu Phe Arg Arg Ile Thr Leu Tyr Gly Phe Asp Pro
            500                 505                 510
Pro Arg Ile Asn Val Gly Gly Pro Cys Phe Pro Ala Leu Gly Gly Met
        515                 520                 525
Phe Ala Lys Ala Lys Tyr Glu Lys Pro Gly Leu Glu Leu Thr Thr Thr
    530                 535                 540
Lys Ala Ala Val Ala Lys Gly Lys His Gly Phe Leu Pro Met Pro Lys
545                 550                 555                 560
Lys Ser Tyr Gly Lys Ser Asp Ala Phe Ala Asp Thr Ile Pro Met Ala
                565                 570                 575
Ser His Pro Ser Pro Phe Ala Ala Ser Ala Ala Ser Val Val Ala
            580                 585                 590
Asp Glu Ala Thr Ile Ala Glu Ala Val Ala Val Cys Ala Ala Ala Tyr
        595                 600                 605
Glu Lys Lys Thr Gly Trp Gly Ser Asp Ile Gly Trp Val Tyr Gly Thr
    610                 615                 620
Val Thr Glu Asp Val Val Thr Gly Tyr Arg Met His Ile Lys Gly Trp
625                 630                 635                 640
Arg Ser Arg Tyr Cys Ser Ile Tyr Pro His Ala Phe Ile Gly Thr Ala
                645                 650                 655
Pro Ile Asn Leu Thr Glu Arg Leu Phe Gln Val Leu Arg Trp Ser Thr
            660                 665                 670
Gly Ser Leu Glu Ile Phe Phe Ser Arg Asn Asn Pro Leu Phe Gly Ser
        675                 680                 685
Thr Phe Leu His Pro Leu Gln Arg Val Ala Tyr Ile Asn Ile Thr Thr
    690                 695                 700
Tyr Pro Phe Thr Ala Ile Phe Leu Ile Phe Tyr Thr Thr Val Pro Ala
705                 710                 715                 720
Leu Ser Phe Val Thr Gly His Phe Ile Val Gln Arg Pro Thr Thr Met
                725                 730                 735
Phe Tyr Val Tyr Leu Ala Ile Val Leu Gly Thr Leu Leu Ile Leu Ala
            740                 745                 750
Val Leu Glu Val Lys Trp Ala Gly Val Thr Val Phe Glu Trp Phe Arg
    755                 760                 765
Asn Gly Gln Phe Trp Met Thr Ala Ser Cys Ser Ala Tyr Leu Ala Ala
770                 775                 780
Val Cys Gln Val Leu Val Lys Val Val Phe Arg Arg Asp Ile Ser Phe
785                 790                 795                 800
Lys Leu Thr Ser Lys Gln Pro Ala Gly Asp Glu Lys Lys Asp Pro Tyr
                805                 810                 815
Ala Asp Leu Tyr Val Val Arg Trp Thr Trp Leu Met Val Thr Pro Ile
            820                 825                 830
Ile Ile Ile Leu Val Asn Ile Ile Gly Ser Ala Val Ala Phe Ala Lys
        835                 840                 845
Val Leu Asp Gly Glu Trp Thr His Trp Leu Lys Val Ala Gly Gly Val
    850                 855                 860
Phe Phe Asn Phe Trp Val Leu Phe His Leu Tyr Pro Phe Ala Lys Gly
865                 870                 875                 880
Ile Leu Gly Arg His Gly Lys Thr Pro Val Val Val Leu Val Trp Trp
                885                 890                 895
Ala Phe Thr Phe Val Ile Thr Ala Val Leu Tyr Ile Asn Ile Pro His
```

```
                        900                 905                 910
Ile His Gly Pro Gly Lys His Gly Gly Ala Ile Gly Arg His Gly
                915                 920                 925

Gly Asp Ala His His His Gly Lys Lys Phe Asp Gly Tyr Tyr Leu Trp
        930                 935                 940

Pro
945

<210> SEQ ID NO 8
<211> LENGTH: 961
<212> TYPE: PRT
<213> ORGANISM: Sorghum bicolor

<400> SEQUENCE: 8

Met Ala Pro Gly Gly Gly Asp Gly Arg Arg Asn Gly Glu Gly Gln Gln
1               5                   10                  15

Gln Ala Asn Gly Asn Asn Asn Asn Asn Ser Asn Ala Lys Ala Lys
            20                  25                  30

His Gly Cys Val Cys Gly Phe Pro Val Cys Ala Cys Ala Gly Ala Ala
        35                  40                  45

Ala Val Ala Ser Ala Ala Ser Ser Ala Asp Met Asp Arg Val Ala Ala
50                  55                  60

Ala Gln Thr Glu Gly Gln Ile Gly Ala Val Asn Asp Glu Ser Trp Ile
65                  70                  75                  80

Ala Val Asp Leu Ser Asp Asp Leu Ser Gly Asp Gly Gly Ala Asp
                85                  90                  95

Pro Gly Val Ala Ile Glu Asp Arg Pro Val Phe Arg Thr Glu Lys Ile
            100                 105                 110

Lys Gly Ile Leu Leu His Pro Tyr Arg Val Leu Ile Phe Val Arg Leu
        115                 120                 125

Ile Ala Phe Thr Leu Phe Val Ile Trp Arg Ile Ser His Arg Asn Pro
    130                 135                 140

Asp Ala Met Trp Leu Trp Val Thr Ser Ile Ala Gly Glu Phe Trp Phe
145                 150                 155                 160

Gly Phe Ser Trp Leu Leu Asp Gln Leu Pro Lys Leu Asn Pro Ile Asn
                165                 170                 175

Arg Val Pro Asp Leu Ala Val Leu Arg Gln Arg Phe Asp Arg Ala Asp
            180                 185                 190

Gly Thr Ser Arg Leu Pro Gly Leu Asp Ile Phe Val Thr Thr Ala Asp
        195                 200                 205

Pro Phe Lys Glu Pro Ile Leu Ser Thr Ala Asn Ser Ile Leu Ser Ile
    210                 215                 220

Leu Ala Ala Asp Tyr Pro Val Glu Arg Asn Thr Cys Tyr Leu Ser Asp
225                 230                 235                 240

Asp Ser Gly Met Leu Leu Thr Tyr Glu Ala Met Ala Glu Ala Ala Lys
                245                 250                 255

Phe Ala Thr Val Trp Val Pro Phe Cys Arg Lys His Gly Ile Glu Pro
            260                 265                 270

Arg Gly Pro Glu Ser Tyr Phe Glu Leu Lys Ser His Pro Tyr Met Gly
        275                 280                 285

Arg Ser Gln Glu Asp Phe Val Asn Asp Arg Arg Val Arg Lys Glu
    290                 295                 300

Tyr Asp Glu Phe Lys Ala Arg Ile Asn Gly Leu Glu His Asp Ile Lys
305                 310                 315                 320
```

Gln Arg Ser Asp Ala Phe Asn Ala Ala Arg Gly Leu Lys Asp Gly Glu
                325                 330                 335

Pro Arg Ala Thr Trp Met Ala Asp Gly Asn Gln Trp Glu Gly Thr Trp
            340                 345                 350

Val Glu Pro Ser Glu Asn His Arg Lys Gly Asp His Ala Gly Ile Val
        355                 360                 365

Tyr Val Leu Leu Asn His Pro Ser His Ser Arg Gln Leu Gly Pro Pro
    370                 375                 380

Ala Ser Ala Asp Asn Pro Leu Asp Phe Ser Met Val Asp Val Arg Leu
385                 390                 395                 400

Pro Met Leu Val Tyr Val Ser Arg Glu Lys Arg Pro Gly Phe Asn His
                405                 410                 415

Glu Lys Lys Ala Gly Ala Met Asn Ala Leu Thr Arg Cys Ser Ala Val
            420                 425                 430

Ile Ser Asn Ser Pro Phe Ile Leu Asn Leu Asp Cys Asp His Tyr Ile
        435                 440                 445

Asn Asn Ser Gln Ala Leu Arg Ala Gly Ile Cys Phe Met Leu Gly Arg
    450                 455                 460

Asp Ser Asp Thr Val Ala Phe Val Gln Phe Pro Gln Arg Phe Glu Gly
465                 470                 475                 480

Val Asp Pro Thr Asp Leu Tyr Ala Asn His Asn Arg Ile Phe Phe Asp
                485                 490                 495

Gly Thr Leu Arg Ala Leu Asp Gly Met Gln Gly Pro Ile Tyr Val Gly
            500                 505                 510

Thr Gly Cys Met Phe Arg Arg Ile Thr Leu Tyr Gly Phe Asp Pro Pro
        515                 520                 525

Arg Ile Asn Val Gly Gly Pro Cys Phe Pro Ser Leu Gly Gly Met Phe
    530                 535                 540

Ala Lys Thr Lys Tyr Glu Lys Pro Gly Leu Glu Leu Thr Thr Lys Ala
545                 550                 555                 560

Ala Val Ala Lys Gly Lys His Gly Phe Leu Pro Leu Pro Lys Lys Ser
                565                 570                 575

Tyr Gly Lys Ser Asp Ala Phe Val Asp Thr Ile Pro Arg Ala Ser His
            580                 585                 590

Pro Ser Pro Phe Leu Ser Ala Asp Glu Ala Ala Ile Val Ala Asp
        595                 600                 605

Glu Ala Met Ile Thr Glu Ala Val Glu Val Cys Thr Ala Ala Tyr Glu
    610                 615                 620

Lys Lys Thr Gly Trp Gly Ser Asp Ile Gly Trp Val Tyr Gly Thr Val
625                 630                 635                 640

Thr Glu Asp Val Val Thr Gly Tyr Arg Met His Ile Lys Gly Trp Arg
                645                 650                 655

Ser Arg Tyr Cys Ser Ile Tyr Pro His Ala Phe Ile Gly Thr Ala Pro
            660                 665                 670

Ile Asn Leu Thr Glu Arg Leu Tyr Gln Val Leu Arg Trp Ser Thr Gly
        675                 680                 685

Ser Leu Glu Ile Phe Phe Ser Arg Asn Asn Pro Leu Phe Gly Ser Thr
    690                 695                 700

Phe Leu His Pro Leu Gln Arg Val Ala Tyr Ile Asn Ile Thr Thr Tyr
705                 710                 715                 720

Pro Phe Thr Ala Leu Phe Leu Ile Phe Tyr Thr Thr Val Pro Ala Leu
                725                 730                 735

Ser Phe Val Thr Gly His Phe Ile Val Gln Arg Pro Thr Thr Met Phe

```
                740                 745                 750
Tyr Val Tyr Leu Ala Ile Val Leu Gly Thr Leu Leu Ile Leu Ala Val
            755                 760                 765
Leu Glu Val Lys Trp Ala Gly Val Thr Val Phe Glu Trp Phe Arg Asn
            770                 775                 780
Gly Gln Phe Trp Met Thr Ala Ser Cys Ser Ala Tyr Leu Ala Ala Val
785                 790                 795                 800
Cys Gln Val Leu Val Lys Val Val Phe Arg Arg Asp Ile Ser Phe Lys
                805                 810                 815
Leu Thr Ser Lys Gln Pro Ala Gly Asp Glu Lys Lys Asp Pro Tyr Ala
            820                 825                 830
Asp Leu Tyr Val Val Arg Trp Thr Trp Leu Met Val Thr Pro Ile Ile
            835                 840                 845
Ile Ile Leu Val Asn Ile Ile Gly Ser Ala Val Ala Phe Ala Lys Val
        850                 855                 860
Leu Asp Gly Glu Trp Thr His Trp Leu Lys Val Ala Gly Gly Val Phe
865                 870                 875                 880
Phe Asn Phe Trp Val Leu Phe His Leu Tyr Pro Phe Ala Lys Gly Leu
                885                 890                 895
Leu Gly Arg His Gly Lys Thr Pro Val Val Leu Val Trp Trp Ala
            900                 905                 910
Phe Thr Phe Val Ile Thr Ala Val Leu Tyr Ile Asn Ile Pro His Ile
            915                 920                 925
His Gly Pro Gly Gly Lys His Gly Gly Ala Ile Gly Lys His Gly Ala
        930                 935                 940
Ala His His Gly Lys Lys Phe Asp Leu Asp Asn Leu Ser Tyr Asn Trp
945                 950                 955                 960
Pro

<210> SEQ ID NO 9
<211> LENGTH: 892
<212> TYPE: PRT
<213> ORGANISM: Brachypodium distachyon

<400> SEQUENCE: 9

Met Arg Ser Leu Arg Arg Val Leu Phe Pro Leu Val Leu Leu Ser Gly
1               5                   10                  15
Leu Ala Phe Arg Gly Val His Phe Asn Asp Ala Ala Ala Pro Thr Pro
            20                  25                  30
Leu Leu Leu Pro Leu Ser Pro Pro Ala Leu Pro Ser Pro Pro Leu
        35                  40                  45
Ala Leu Pro Ala Asp Glu Gly Arg Gly Asp Gly Ala Asp Ser Arg Glu
50                  55                  60
Ile Ile Ala Ala Pro Leu Pro Gly Glu Leu Leu Val Arg Pro Pro Arg
65                  70                  75                  80
Arg Arg Ser Glu Pro Thr Asn Ala Val Thr Asp Ala Gly Pro His Ile
                85                  90                  95
Ser Ser Glu Leu Gln Phe Asn Asp Asp Gly Thr Ile Gln Leu Val Asp
            100                 105                 110
Arg Leu Ser Lys Ser Ser Leu Trp Gln Phe Ser Thr Gly Pro Pro Leu
            115                 120                 125
Ser Lys His Val Thr Thr Ala Asn Ser Asp Leu Gly Tyr Leu Ile Tyr
        130                 135                 140
Pro Leu Asp Gln Ala Lys Leu Val Glu Val His Asn Gly Ser Val Met
```

```
            145                 150                 155                 160
Ala Leu Pro Trp Glu Leu Asp Glu Phe Ile Ser Arg Thr Pro Tyr Val
                165                 170                 175
Arg Asp Ser Val Val Thr Ile Gly Ser Lys Thr Ser Thr Ile Phe Ala
                180                 185                 190
Val Asp Ala Asp Ser Gly Glu Ile Ile Tyr Lys His Ser Leu Pro Ile
                195                 200                 205
Ala Leu Asn Glu Leu Gly Ala Thr Pro Val Glu Glu Ala Pro Ser Lys
            210                 215                 220
Leu Asp Ala Gly Arg Ser Gly Ser Pro Asn Val Ile Leu Val Arg
225                 230                 235                 240
Thr Asp Tyr Ser Val Ser Ala Ser Asp Leu Gly Val His Leu Phe Asn
                245                 250                 255
Trp Thr Arg Thr Ser Phe Ser Ala Asn Tyr Tyr Val Lys Gln Ser His
                260                 265                 270
Pro Asp Thr Leu Glu Gln Ser Ser Cys Leu Arg Gly Asn Ile Pro Cys
                275                 280                 285
Phe Arg Ser Asp Gly Val Pro Leu Lys Leu Thr Leu Pro Glu Ser Ser
                290                 295                 300
Thr Ala Asn Ala Leu Val Leu Arg Asp Leu Asn Lys Val Thr Thr Arg
305                 310                 315                 320
Tyr Asp Ala Asp Ala Leu Arg Pro Val Ala Thr Met Met Lys Ser Leu
                325                 330                 335
Gln Ala Ala Ser Lys Ser Asn Val Val Leu Asp Ser Thr Gln Asn Gln
                340                 345                 350
Thr Val Asp Asp Ala Pro Gly Arg Leu Val Ser Ala Asp Pro Gln Ala
            355                 360                 365
Asn Arg Phe Ser Asn Asn Thr His Gly Leu Leu Phe Pro Val Val Ser
            370                 375                 380
Leu Leu Val Val Leu Ala Trp Leu Val Ser Leu Ala Tyr Ser Ser Lys
385                 390                 395                 400
Pro Cys Arg Gln Phe Val Gly Gln Leu Phe Lys Pro Phe Val His Glu
                405                 410                 415
Lys Lys Ser Thr Gly Leu Ala Gly Lys Thr Glu Lys Thr Ser Lys Arg
            420                 425                 430
Arg Lys Thr Arg Lys Lys Asp Gly Ile Ala Asn Gly Thr Asp Ile Cys
            435                 440                 445
Ser Ser Ser Asp Lys Glu Asn Gly Glu Thr Gly Gly Ser Asn Glu Thr
450                 455                 460
Val Tyr Asn Glu Thr Tyr Gln Leu Thr Gly Thr Ala Leu Pro Asp Gly
465                 470                 475                 480
Leu Asp Gly Cys Gln Ile Gly Lys Leu Arg Val His Lys Lys Glu Ile
                485                 490                 495
Gly Lys Gly Ser Asn Gly Thr Val Val Phe Glu Gly Ser Tyr Asp Gly
                500                 505                 510
Arg Glu Val Ala Val Lys Arg Leu Leu Arg Ser His Thr Asp Ile Ala
            515                 520                 525
Gln Lys Glu Ile Gln Asn Leu Ile Ala Ser Asp Arg Asp Pro Asn Ile
            530                 535                 540
Val Arg Leu Tyr Gly Cys Asp Gln Asp Asp Asn Phe Val Tyr Ile Ser
545                 550                 555                 560
Leu Glu Arg Cys Arg Cys Ser Leu Ala Asp Leu Ile Gln Gln His Ile
                565                 570                 575
```

```
Asp Pro Ser Phe Ser Asp Val Glu Arg Ile Asp Val Glu Leu Trp Arg
            580                 585                 590
Gln Asp Gly Leu Pro Ser Ala Gln Leu Leu Lys Leu Met Arg Asp Val
        595                 600                 605
Val Ala Gly Ile Val His Leu His Ser Leu Gly Ile Ile His Arg Asp
610                 615                 620
Leu Lys Pro Gln Asn Val Leu Ile Ser Lys Glu Gly Pro Leu Ser Ala
625                 630                 635                 640
Lys Leu Ser Asp Met Gly Ile Ser Lys Arg Leu Gln Glu Asp Met Thr
                645                 650                 655
Ser Leu Ser His His Gly Thr Gly Tyr Gly Ser Ser Gly Trp Gln Ala
            660                 665                 670
Pro Glu Gln Leu Arg Gly Asp Ser Gln Thr Arg Ala Met Asp Leu Phe
        675                 680                 685
Ser Leu Gly Cys Leu Ile Phe Tyr Cys Ile Thr Lys Gly Lys His Pro
    690                 695                 700
Phe Gly Glu Tyr Tyr Glu Arg Asp Met Asn Ile Ile Asn Asn His Phe
705                 710                 715                 720
Asp Leu Phe Val Val Asp His Ile Pro Glu Ala Val His Leu Ile Ser
                725                 730                 735
Gln Leu Leu Gln Pro Lys Pro Glu Met Arg Pro Thr Ala Val Tyr Val
            740                 745                 750
Ile Asn His Pro Leu Phe Trp Cys Pro Glu Leu Arg Leu Leu Phe Leu
        755                 760                 765
Arg Asp Thr Ser Asp Arg Ile Glu Lys Thr Thr Glu Thr Asp Leu Ile
    770                 775                 780
Asn Ala Leu Glu Ser Ile Gly Tyr Glu Ala Phe Gly Gly Lys Trp Arg
785                 790                 795                 800
Glu Lys Leu Asp Asp Gly Leu Val Ala Asp Met Gly Arg Tyr Arg Lys
                805                 810                 815
Tyr Asn Phe Glu Ser Thr Arg Asp Leu Leu Arg Leu Ile Arg Asn Lys
            820                 825                 830
Ser Gly His Tyr Arg Glu Leu Pro Ala Asp Leu Lys Glu Leu Leu Gly
        835                 840                 845
Ser Leu Pro Glu Gly Phe Asp Arg Tyr Phe Ser Ser Arg Phe Pro Lys
    850                 855                 860
Leu Leu Ile Glu Val Tyr Lys Val Met Ser Val His Cys Lys Asp Glu
865                 870                 875                 880
Glu Ala Phe Arg Lys Tyr Phe Ile Gly Ser Ser Val
                885                 890

<210> SEQ ID NO 10
<211> LENGTH: 2679
<212> TYPE: DNA
<213> ORGANISM: Brachypodium distachyon

<400> SEQUENCE: 10
atgaggtcgc tccgccgggt cctcttcccg ctcgtcctcc tttcggggct cgcctttcgt      60
ggtgtccact tcaacgacgc cgccgcccccg acccccttc tctcccgct ttccccacca     120 ccggcgctgc cgtcgccgcc cctcgcgctc cctgctgacg aagggcgagg ggatggtgcg     180
gactccaggg agatcatcgc ggcgccgctg cccggggagc tccttgtcag gccgccccgc     240
cgccgctcgg agccgacgaa cgcggtgacc gatgctggcc ccacatcag ctccgaacta      300
```

```
caattcaacg acgatggcac aattcaactt gttgatcgtc tatcaaaatc ttctttgtgg    360
cagttctcca caggaccgcc tctttcgaag catgtcacta cagcaaactc agatttgggc    420
tatctcatat atcctttaga tcaagctaag cttgtggaag ttcataatgg cagtgttatg    480
gcacttccct gggaactgga cgagtttatt agcagaactc cgtatgtacg ggactctgtc    540
gttactattg gatcaaaaac ttcaactatt tttgcagttg atgctgatag tggggagatc    600
atttacaagc atagcttgcc aatcgctttg aatgaattag gagcaacccc tgttgaagaa    660
gcaccatcca agctggatgc tggtagaagt ggtagtccta atgtcatagt gcttgttaga    720
actgattatt ctgtcagtgc gtctgaccta ggcgttcatt tgtttaactg gacaagaact    780
tctttctctg caaactatta tgtgaaacag agccatccag atacgttaga acaatcatcc    840
tgtctgcgag gaaatattcc ttgctttagg tctgatggtg taccacttaa actcacgtta    900
cctgagtcta gtacagccaa tgcacttgtc ttgagagatt tgaacaaagt taccactagg    960
tatgatgctg atgccttgag accagttgca actatgatga agtcactaca agctgctagc   1020
aagtctaatg ttgttctgga cagtactcag aatcaaactg ttgatgatgc tcctggtcgc   1080
cttgtctctg ctgatcccca agccaacagg ttcagtaaca atactcatgg attgttattc   1140
cctgttgttt ccttattggt ggtcctcgct tggctagtga gcttggccta ttcaagcaag   1200
ccttgcaggc aattcgtggg tcagcttttt aagccatttg tccatgaaaa gaaatcgaca   1260
ggccttgcag gaaagacaga gaaaacttct aagagaagaa aaacacgaaa gaaagacgga   1320
attgccaatg gcactgatat ctgttcatca tctgacaaag agaacggtga aactggtggg   1380
tcaaatgaga cggtatataa tgaaacctac caattaacag gtaccgcact ccctgatggt   1440
cttgatggat gccagattgg taagcttcgt gttcacaaaa agaaattggt aaagggagc    1500
aatggtacag ttgtctttga gggttcctat gatggtcgtg aagttgcagt gaaacgtctg   1560
ctacgttcac acactgatat agcgcaaaaa gagattcaga atcttattgc atccgaccgg   1620
gatcctaata tcgttagact gtatggctgc gatcaggatg taaattttgt ttatatctcc   1680
cttgagagat gccgctgcag cttggctgat cttattcaac agcatataga tccatcattt   1740
tcagatgttg agcgaataga tgttgaactg tggaggcagg atgggctccc ttccgcacaa   1800
ctcctaaagc tgatgagaga tgttgttgct ggcattgtgc atttgcatag tttaggaatc   1860
atacatcgcg atttgaagcc tcagaacgtt ttgataagta aggaaggacc tctcagcgca   1920
aaactttcag atatgggtat cagtaagcgc ttgcaagagg atatgacttc tcttagccat   1980
catggtactg gatatggaag ctctggttgg caagcacctg aacagcttcg tggtgatagt   2040
cagactcgtg caatggattt atttagtttg ggctgcctta ttttctattg tatcaccaaa   2100
ggcaagcatc cgtttggtga gtactatgag cgggacatga acattataaa caatcacttt   2160
gatctcttcg tggtggatca cataccagaa gcagtacatc ttatttctca attgttacag   2220
ccaaaaccag aaatgagacc aacggcagta tacgtgataa atcatcctct cttctggtgc   2280
cctgagttgc ggcttctgtt cctacgggat accagtgaca gaattgagaa aaccactgaa   2340
actgacctca taaatgcttt ggaaagcata gggtatgaag cgtttggtgg aaaatggcga   2400
gaaaagttgg atgatggtct ggttgccgac atgggtcgtt ataggaaata taattttgag   2460
tccacacgtg accttctgag gttgattaga aataagtcag acattacag ggagctgcca    2520
gctgatctca aggaattact tgggtcgctg cctgagggat ttgatcgcta tttctcaagc   2580
cgatttccaa agctgctgat tgaagtgtac aaggtcatgt ctgtgcactg caaggatgag   2640
gaagctttca ggaaatattt cattggaagc tcggtataa                          2679
```

```
<210> SEQ ID NO 11
<211> LENGTH: 883
<212> TYPE: PRT
<213> ORGANISM: Triticum aestivum

<400> SEQUENCE: 11

Met Arg Ser Leu Arg Arg Val Leu Leu Pro Leu Val Leu Leu Ser Gly
1               5                   10                  15

Leu Ala Phe Arg Gly Ala Arg Phe Glu Asp Asp Ala Asp Ser Ala Pro
            20                  25                  30

Ala Pro Leu Leu Leu Pro Leu Pro Ala Pro Gln Gln Pro Ala
        35                  40                  45

Pro Ser Leu Ala Leu Pro Ala Ala Gly Gly Arg Gly Asp Glu Ala Gly
50                  55                  60

Ser Thr Glu Ile Val Pro Ala Glu Gln Pro Phe Leu Val Arg Pro Pro
65                  70                  75                  80

Arg Arg Arg Ser Val Pro Ser Asn Ala Val Lys Asn Pro Asp Val Gly
                85                  90                  95

Pro Gly Ile Ser Ser Glu Leu Arg Phe Tyr Asp Asn Gly Thr Ile Gln
            100                 105                 110

Leu Val Asp Arg Leu Ser Glu Ser Pro Leu Trp Gln Phe Ser Thr Gly
        115                 120                 125

Pro Pro Leu Ser Lys His Ile Thr Thr Thr Asn Ser Asp Leu Ser Tyr
    130                 135                 140

Leu Ile Tyr Pro Leu Asp Glu Ser Asp Leu Val Glu Val His Asn Gly
145                 150                 155                 160

Thr Gly Val Lys Leu Pro Trp Glu Leu Glu Glu Phe Ile Ala Arg Thr
                165                 170                 175

Pro Tyr Ile Arg Asp Ser Val Thr Ile Gly Ser Lys Ala Ser Thr
            180                 185                 190

Thr Phe Ala Val Asp Ala Asp Ser Gly Glu Ile Ile Tyr Lys His Ser
        195                 200                 205

Leu Pro Ala Ala Leu Asn Glu Leu Ala Val Pro Ala Gly Glu Ala Pro
    210                 215                 220

Ser Lys Leu Asp Val Gly Arg Ser Ser Asn Ile Ile Val Val Arg
225                 230                 235                 240

Thr Asp Tyr Ser Leu Ser Ala Ser Asp Leu Gly Val His Leu Phe Asn
                245                 250                 255

Trp Thr Arg Ser Ser Phe Ser Ala Asn Tyr Tyr Val Lys Gln Ser His
            260                 265                 270

Pro Asn Met Leu Glu Gln Ser Ser Cys Leu Gln Glu Asn Ile Pro Cys
        275                 280                 285

Ile Arg Thr Asp Gly Val Pro Ile Lys Leu Thr Leu Pro Asp Ser Ser
    290                 295                 300

Thr Ala Asn Ala Leu Val Leu Gln Asp Val Asn Lys Val Thr Thr Arg
305                 310                 315                 320

Asp Gly Ala Asp Ala Leu Arg Gln Leu Gln Thr Leu Val Ile Pro Gln
                325                 330                 335

Gln Thr Ala Ser Lys Ser Gly Val Ala Leu Asn Gly Thr Gln Asn Gln
            340                 345                 350

Thr Val Asp Gly Ala Leu Val His Leu Val Pro Ala Asp Pro Gln Ala
        355                 360                 365

Asn Arg Phe Thr Asn Asn Ala Tyr Gly Leu Leu Phe Pro Val Leu Thr
```

-continued

```
            370                 375                 380
Leu Leu Val Val Leu Ala Trp Leu Val Arg Leu Ala Tyr Ser Ser Lys
385                 390                 395                 400

Ser Cys Lys Gln Phe Met Ser Val Leu Met Lys Pro Phe Val Arg Glu
                    405                 410                 415

Gln Lys Ser Ile Asp Leu Arg Gly Lys Ser Glu Gly Thr Ser Lys Arg
                420                 425                 430

Arg Lys Thr Arg Lys Lys Asp Gly Arg Ala Asn Ser Thr Glu Ile Gly
            435                 440                 445

Ser Ala Ser Asp Lys Glu Ser Ser Gly Thr Gly Ser Asn Glu Met
    450                 455                 460

Leu Tyr Ala Leu Pro Asp Gly Leu Asp Gly Cys Gln Ile Gly Lys Leu
465                 470                 475                 480

Arg Val His Lys Lys Glu Ile Gly Lys Gly Ser Asn Gly Thr Val Val
                485                 490                 495

Phe Glu Gly Ser Tyr Asp Gly Arg Glu Val Ala Val Lys Arg Leu Leu
                500                 505                 510

Arg Ser His Thr Asp Ile Ala Gln Lys Glu Ile Gln Asn Leu Ile Ala
                515                 520                 525

Ser Asp Arg Asp Pro Asn Ile Val Arg Leu Tyr Gly Cys Asp Gln Asp
    530                 535                 540

Asp Asn Phe Val Tyr Ile Ser Leu Glu Arg Cys Arg Cys Ser Leu Ala
545                 550                 555                 560

Asp Leu Ile Gln Gln His Thr Asp Pro Ser Phe Ser Asp Val Glu Lys
                565                 570                 575

Ile Asp Val Glu Leu Trp Thr Gln Asp Gly Leu Pro Ser Pro Gln Leu
                580                 585                 590

Leu Lys Leu Met Arg Asp Val Val Ala Gly Ile Val His Leu His Ser
            595                 600                 605

Leu Gly Ile Ile His Arg Asp Leu Lys Pro Gln Asn Val Leu Ile Ser
        610                 615                 620

Lys Glu Gly Ser Leu Ser Ala Lys Leu Ser Asp Met Gly Ile Ser Lys
625                 630                 635                 640

Arg Leu Gln Glu Asp Met Ser Ser Leu Ser His His Gly Thr Gly Tyr
                645                 650                 655

Gly Ser Ser Gly Trp Gln Ala Pro Glu Gln Leu Arg Arg Ala Ser Gln
                660                 665                 670

Thr Arg Ala Met Asp Leu Phe Ser Leu Gly Cys Leu Ile Phe Tyr Cys
            675                 680                 685

Ile Thr Lys Gly Lys His Pro Phe Gly Glu Tyr Tyr Glu Arg Asp Ile
        690                 695                 700

Asn Ile Ile Asn Gly His Phe Asp Leu Phe Val Asp His Ile Pro
705                 710                 715                 720

Glu Ala Val His Leu Ile Ser Leu Leu Leu Gln Pro Lys Pro Asp Glu
                725                 730                 735

Arg Pro Thr Ala Val Tyr Ala Ile Asn His Pro Leu Phe Trp Ser Pro
                740                 745                 750

Glu Leu Arg Leu Leu Phe Leu Arg Asp Thr Ser Asp Arg Ile Glu Lys
            755                 760                 765

Thr Thr Glu Thr Asp Leu Leu Asn Ala Leu Glu Ser Ile Gly His Gln
        770                 775                 780

Ala Phe Gly Gly Lys Trp Arg Glu Lys Leu Asp Asp Gly Leu Val Ala
785                 790                 795                 800
```

```
Asp Val Gly Arg Tyr Arg Lys Tyr Asn Phe Glu Ser Thr Arg Asp Leu
                805                 810                 815

Leu Arg Leu Ile Arg Asn Lys Ser Gly His Tyr Arg Glu Leu Pro Ala
            820                 825                 830

Asp Leu Lys Glu Leu Leu Gly Ser Leu Pro Gly Phe Asp Arg Tyr
        835                 840                 845

Phe Ser Ile Arg Phe Pro Lys Leu Leu Ile Glu Val Tyr Lys Val Met
        850                 855                 860

Ser Val Tyr Cys Lys Asp Glu Asp Phe Arg Lys Tyr Phe Ile Gly
865                 870                 875                 880

Ile Ser Val

<210> SEQ ID NO 12
<211> LENGTH: 881
<212> TYPE: PRT
<213> ORGANISM: Hordeum vulgare

<400> SEQUENCE: 12

Met Arg Ser Leu Arg Arg Val Leu Leu Pro Leu Val Leu Leu Ser Gly
1               5                   10                  15

Leu Ala Phe Arg Gly Ala Arg Phe Asp Asp Ala Asp Ala Ala Pro Ala
            20                  25                  30

Pro Leu Leu Leu Pro Leu Pro Leu Pro Gln Gln Pro Ala Pro Ser
        35                  40                  45

Leu Ala Leu Pro Ala Gly Asp Glu Ala Gly Ser Thr Glu Ile Val Ala
    50                  55                  60

Ala Glu Gln Pro Ser Leu Arg Glu Leu Leu Val Arg Pro Pro Arg Arg
65                  70                  75                  80

Arg Ser Glu Pro Ala Asn Ala Val Leu Pro Asp Thr Gly Pro Gly Ile
                85                  90                  95

Ser Ser Glu Leu Arg Phe Tyr Asp Asn Gly Thr Ile Gln Leu Val Asp
            100                 105                 110

Arg Arg Ser Glu Ala Pro Leu Trp Gln Phe Ser Thr Gly Pro Pro Leu
        115                 120                 125

Ser Lys His Ile Thr Thr Thr Asn Ser Asp Leu Ser Tyr Leu Ile Tyr
    130                 135                 140

Pro Leu Asp Glu Ser Asp Leu Val Glu Val His Asn Gly Thr Gly Val
145                 150                 155                 160

Lys Leu Pro Trp Glu Leu Glu Glu Phe Ile Ala Arg Thr Pro Tyr Ile
                165                 170                 175

Arg Asp Ser Val Val Thr Ile Gly Ser Lys Ala Ser Thr Thr Phe Thr
            180                 185                 190

Val Asp Ala Asp Ser Gly Glu Ile Ile Tyr Lys His Ser Leu Pro Ala
        195                 200                 205

Ala Leu Asn Glu Leu Gly Ala Val Pro Val Gly Glu Val Pro Ser Lys
    210                 215                 220

Leu Asp Val Gly Arg Ser Ser Asn Ile Ile Val Val Arg Thr Asp
225                 230                 235                 240

Tyr Ser Leu Ser Ala Ser Asp Leu Gly Val His Leu Phe Asn Trp Thr
                245                 250                 255

Arg Ser Ser Phe Ser Ala Asn Tyr Tyr Val Lys His Ser His Pro Asp
            260                 265                 270

Met Leu Glu Gln Ser Ser Cys Leu Gln Glu Asn Ile Pro Cys Ile Arg
        275                 280                 285
```

```
Thr Asp Gly Val Pro Leu Lys Leu Thr Leu Pro Asp Ser Ser Thr Ser
    290                 295                 300

Asn Ala Leu Val Leu Arg Asp Val Asp Lys Val Thr Thr Arg Asp Gly
305                 310                 315                 320

Ala Asp Ala Leu Arg Leu Leu Gln Thr Leu Val Ile Pro Gln Gln Thr
                325                 330                 335

Ala Ser Lys Ser Gly Val Ala Leu Asp Gly Thr Gln Asn Arg Thr Val
                340                 345                 350

Asp Gly Ala Leu Ser His Leu Val Pro Ala Asp Pro Gln Thr Asn Arg
            355                 360                 365

Phe Thr Asn Asn Ala Tyr Gly Leu Leu Phe Pro Val Leu Thr Leu Leu
        370                 375                 380

Val Val Leu Thr Trp Leu Val Arg Leu Ala Tyr Ser Ser Lys Ser Cys
385                 390                 395                 400

Lys Gln Phe Met Ser Ile Leu Met Lys Pro Phe Val Arg Glu Gln Lys
                405                 410                 415

Ser Ile Asp Pro Arg Gly Lys Ser Glu Gly Thr Ser Lys Arg Arg Lys
                420                 425                 430

Thr Arg Lys Lys Asp Gly Arg Ala Asn Ser Thr Glu Ile Gly Ser Ala
        435                 440                 445

Ser Asp Lys Glu Ser Ser Gly Thr Gly Gly Ser Asn Glu Met Leu Tyr
    450                 455                 460

Ala Leu Pro Asp Gly Leu Asp Gly Cys Gln Ile Gly Lys Leu Arg Val
465                 470                 475                 480

His Lys Lys Glu Ile Gly Lys Gly Ser Asn Gly Thr Val Val Phe Glu
                485                 490                 495

Gly Ser Tyr Asp Gly Arg Glu Val Ala Val Lys Arg Leu Leu Arg Ser
            500                 505                 510

His Thr Asp Ile Ala Gln Lys Glu Ile Gln Asn Leu Ile Ala Ser Asp
        515                 520                 525

Arg Asp Pro Asn Ile Val Arg Leu Tyr Gly Cys Asp Gln Asp Asp Asn
    530                 535                 540

Phe Val Tyr Ile Ser Leu Glu Arg Cys His Cys Ser Leu Ala Asp Leu
545                 550                 555                 560

Ile Gln Gln His Thr Asp Pro Ser Phe Ser Asp Val Glu Lys Ile Asp
                565                 570                 575

Val Glu Leu Trp Thr Gln Asp Gly Leu Pro Ser Pro Gln Leu Leu Lys
            580                 585                 590

Leu Met Arg Asp Val Val Ala Gly Ile Val His Leu His Ser Leu Gly
        595                 600                 605

Ile Ile His Arg Asp Leu Lys Pro Gln Asn Val Leu Ile Ser Lys Glu
    610                 615                 620

Gly Ser Leu Ser Ala Lys Leu Ser Asp Met Gly Ile Ser Lys Arg Leu
625                 630                 635                 640

Gln Glu Asp Met Ser Ser Leu Ser His His Gly Thr Gly Tyr Gly Ser
                645                 650                 655

Ser Gly Trp Gln Ala Pro Glu Gln Leu Arg Arg Ala Ser Gln Thr Arg
            660                 665                 670

Ala Met Asp Leu Phe Ser Leu Gly Cys Leu Ile Phe Tyr Cys Ile Thr
        675                 680                 685

Lys Gly Lys His Pro Phe Gly Glu Tyr Tyr Glu Arg Asp Ile Asn Ile
    690                 695                 700
```

```
Ile Asn Gly His Phe Asp Leu Phe Val Val Asp His Ile Pro Glu Ala
705                 710                 715                 720

Val His Leu Ile Ser Leu Leu Leu Gln Pro Lys Pro Asp Glu Arg Pro
            725                 730                 735

Thr Ala Met Tyr Ala Ile Asn His Pro Leu Phe Trp Ser Pro Glu Leu
        740                 745                 750

Arg Leu Leu Phe Leu Arg Asp Thr Ser Asp Arg Ile Glu Lys Thr Thr
    755                 760                 765

Glu Thr Asp Leu Leu Asn Ala Leu Glu Ser Ile Gly His Gln Ala Phe
770                 775                 780

Gly Gly Lys Trp Arg Glu Lys Leu Asp Asp Gly Leu Val Ala Asp Val
785                 790                 795                 800

Gly Arg Tyr Arg Lys Tyr Asn Phe Glu Ser Thr Arg Asp Leu Leu Arg
                805                 810                 815

Leu Ile Arg Asn Lys Ser Gly His Tyr Arg Glu Leu Pro Thr Asp Leu
            820                 825                 830

Lys Glu Ser Leu Gly Ser Leu Pro Glu Gly Phe Asp Arg Tyr Phe Ser
        835                 840                 845

Ser Arg Phe Pro Lys Leu Leu Ile Glu Val Tyr Lys Val Met Ser Val
    850                 855                 860

Tyr Cys Lys Asp Glu Glu Asp Phe Arg Lys Tyr Phe Ile Gly Ser Ser
865                 870                 875                 880

Val

<210> SEQ ID NO 13
<211> LENGTH: 893
<212> TYPE: PRT
<213> ORGANISM: Oryza sativa

<400> SEQUENCE: 13

Met Arg Ser Leu Arg Arg Val Leu Leu Gln Leu Val Leu Leu Ala Gly
1               5                   10                  15

Val Ala Phe Arg Gly Val Arg Phe Asp Asp Ala Ala Asp Ala Ala Ala
            20                  25                  30

Ala Ala Gln Gly Ser Ser Asp Leu Phe Glu Leu Pro Ser Pro Ser Pro
        35                  40                  45

Thr Leu Ala Leu Pro Gly Gly Asp Glu Gly Ala Ser Thr Glu Ile
50                  55                  60

Ile Ala Ala Pro Trp Pro Gly Arg His Gly Leu Phe Thr Pro Pro Arg
65                  70                  75                  80

Ser Thr Ser Gln Pro Ala Arg Ala Val Val Gln Pro Ala Ala Asp Phe
                85                  90                  95

Gly Ser Gln Leu Gln Phe Tyr Asp Asn Gly Thr Ile Gln Leu Val Asp
            100                 105                 110

Leu Leu Ser Lys Leu Pro Arg Trp Gln Phe Ser Thr Gly Pro Pro Leu
        115                 120                 125

Ser Lys His Ile Thr Thr Ser Lys Pro Asp Leu Asn Tyr Val Ile Tyr
    130                 135                 140

Leu Asp Gly Ser Glu Thr Ser Asp Leu Ile Glu Val His Asn Gly Ser
145                 150                 155                 160

Gly Val Arg Leu Pro Trp Lys Leu Glu Glu Phe Ile Ala Glu Thr Pro
                165                 170                 175

Tyr Ile Arg Asp Ser Phe Val Thr Ile Gly Ser Lys Val Ser Thr Thr
            180                 185                 190
```

```
Phe Val Val Asn Ala Asp Ser Gly Glu Ile Ile Tyr Lys His Ser Leu
            195                 200                 205
Pro Val Ala Leu Asn Glu Val Gly Gly Pro Leu Val Glu Glu Ile Pro
210                 215                 220
Ser Lys Leu Asp Ala Ala Arg Ser Gly Thr Ser Ala Asn Ile Ile Val
225                 230                 235                 240
Val Val Arg Thr Asp Tyr Ser Ile Ser Ala Ser Asp Leu Gly Glu His
            245                 250                 255
Leu Phe Asn Trp Thr Arg Thr Ser Phe Thr Ala Asn Tyr Tyr Ala Arg
            260                 265                 270
Tyr Gly His Gln Asp Met Leu Ala Gln Ser Ser Cys Leu Arg Gly Asn
            275                 280                 285
Ile Pro Cys Ile Arg Thr Glu Gly Pro Pro Ile Lys Leu Tyr Leu Pro
290                 295                 300
Asp Ser Ser Ser Asp Asn Ala Ile Val Leu Arg Pro Val Asn Glu Val
305                 310                 315                 320
Ser Ala Val Asp Ala Leu Glu Pro Leu Pro Pro Lys Lys Leu Pro
            325                 330                 335
Gln Pro Ala Gly Glu Ser Asn Val Ala Leu Asp Ser Ala Gln Asn Gln
            340                 345                 350
Thr Ala Asp Ile Ala Leu Gly His Phe Val Pro Ala Asp Thr Glu Leu
            355                 360                 365
Thr Asn Ser Val Thr Lys Phe Ser Tyr Arg Trp Leu Phe Pro Thr Phe
            370                 375                 380
Leu Met Leu Leu Ile Met Ala Cys Leu Val Lys Leu Ala Asp Ala Ser
385                 390                 395                 400
Lys Tyr Cys Arg Gln Phe Val Ile Arg Phe Leu Lys Pro Phe Met Arg
            405                 410                 415
Asp Glu Lys Leu Met Asp Pro Arg Gly Lys Ser Glu Gly Thr Ser Lys
            420                 425                 430
Arg Arg Lys Ala Arg Lys Asp Gly Leu Ile Asn Ser Thr Gln Ile
            435                 440                 445
Phe Ser Ala Ser Asp Lys Glu Gly Asn Gly Thr Gly Gly Ser Thr Glu
450                 455                 460
Ala Gln Ser Asn Lys Ala His Asp Ser Thr Asn Val Glu Leu Pro Asn
465                 470                 475                 480
Gly Leu Asn Gly Arg Gln Ile Gly Lys Leu Cys Val Tyr Ser Lys Glu
            485                 490                 495
Ile Gly Lys Gly Ser Asn Gly Thr Val Val Phe Glu Gly Ser Tyr Gly
            500                 505                 510
Gly Arg Glu Val Ala Val Lys Arg Leu Leu Arg Ser His Asn Asp Ile
            515                 520                 525
Ala Ser Lys Glu Ile Glu Asn Leu Ile Ala Ser Asp Gln Asp Pro Asn
530                 535                 540
Ile Val Arg Met Tyr Gly Phe Glu Gln Asp Asn Asp Phe Val Tyr Ile
545                 550                 555                 560
Ser Leu Glu Arg Cys Arg Cys Ser Leu Ala Asp Leu Ile Gln Leu His
            565                 570                 575
Ser Val Pro Pro Phe Ser Asn Thr Lys Gly Thr Asp Ile Glu Leu Trp
            580                 585                 590
Arg Gln Asp Gly Leu Pro Ser Ala Gln Leu Leu Lys Leu Met Arg Asp
            595                 600                 605
Val Val Ala Gly Ile Val His Leu His Ser Leu Gly Ile Ile His Arg
```

-continued

```
              610                 615                 620

Asp Leu Lys Pro Gln Asn Val Leu Ile Ser Lys Glu Gly Pro Leu Arg
625                 630                 635                 640

Ala Lys Leu Ser Asp Met Gly Ile Ser Lys Arg Leu Gln Glu Asp Met
                645                 650                 655

Thr Ser Val Ser His His Gly Thr Gly Phe Gly Ser Ser Gly Trp Gln
                660                 665                 670

Ala Pro Glu Gln Leu Arg His Gly Arg Gln Thr Arg Ala Ile Asp Leu
                675                 680                 685

Phe Ser Leu Gly Cys Leu Ile Phe Tyr Cys Ile Thr Lys Gly Lys His
690                 695                 700

Pro Phe Gly Glu Tyr Tyr Glu Arg Asp Met Lys Ile Ile Asn Asn Gln
705                 710                 715                 720

Phe Asp Leu Phe Ile Val Asp His Ile Pro Glu Ala Val His Leu Ile
                725                 730                 735

Ser Gln Leu Leu Asp Pro Asp Pro Glu Lys Arg Pro Thr Ala Val Tyr
                740                 745                 750

Val Met His His Pro Phe Phe Trp Ser Pro Glu Leu Cys Leu Ser Phe
                755                 760                 765

Leu Arg Asp Thr Ser Asp Arg Ile Glu Lys Thr Ser Glu Thr Asp Leu
770                 775                 780

Ile Asp Ala Leu Glu Gly Ile Asn Val Glu Ala Phe Gly Lys Asn Trp
785                 790                 795                 800

Gly Glu Lys Leu Asp Ala Ala Leu Leu Ala Asp Met Gly Arg Tyr Arg
                805                 810                 815

Lys Tyr Ser Phe Glu Ser Thr Arg Asp Leu Leu Arg Leu Ile Arg Asn
                820                 825                 830

Lys Ser Gly His Tyr Arg Glu Phe Ser Asp Asp Leu Lys Glu Leu Leu
                835                 840                 845

Gly Ser Leu Pro Glu Gly Phe Val Gln Tyr Phe Ser Ser Arg Phe Pro
                850                 855                 860

Lys Leu Leu Ile Lys Val Tyr Glu Val Met Ser Glu His Cys Lys Asp
865                 870                 875                 880

Glu Glu Ala Phe Ser Lys Tyr Phe Leu Gly Ser Ser Ala
                885                 890

<210> SEQ ID NO 14
<211> LENGTH: 923
<212> TYPE: PRT
<213> ORGANISM: Sorghum bicolor

<400> SEQUENCE: 14

Met Arg Ser Leu Arg Arg Val Leu Ile Pro Leu Val Leu Leu Ala Gly
1               5                   10                  15

Leu Ala Phe Arg Val Asp Asp Gly Gly Ala Ala Leu Leu Pro Pro Pro
                20                  25                  30

Pro Pro Ala Leu Pro Ala Pro Arg Pro Arg Leu Ala Leu Pro Gly Gly
                35                  40                  45

Ala Ala Pro Glu Asp Asp Val Ala Ala Ala Ala Ser Arg Ser Thr
                50                  55                  60

Glu Ile Val Ala Val Gly Ala Arg Ser Thr Glu Ile Val Ala Pro Ala
65                  70                  75                  80

Gly Pro Lys Lys Gln Ser Leu Arg Glu Leu Leu Val Arg Pro Gln Pro
                85                  90                  95
```

```
Ala Arg His Glu Pro Ala Asn Leu Val Ser Gly Glu Ala Lys Ala Glu
             100                 105                 110

Pro Ser Pro Val Leu Gln Phe Tyr Asp Asn Gly Thr Ile Gln Leu Val
        115                 120                 125

Asp Gln Leu Ser Gln Ser Pro Met Trp Glu Ile Thr Thr Gly Pro Pro
    130                 135                 140

Leu Ser Asp His Ile Thr Thr Thr Asp Ser Gly Leu Asn Tyr Leu Ile
145                 150                 155                 160

Tyr Pro Leu Met Asn Gly Asn Gly Thr Glu Leu Trp Glu Val Tyr Asn
                165                 170                 175

Gly Asn Asn Val Arg Leu Pro Trp Lys Leu Glu Glu Phe Val Ala Arg
            180                 185                 190

Ser Pro Tyr Val Arg Asp Ser Val Thr Val Gly Ser Lys Val Ser
        195                 200                 205

Thr Val Phe Val Val Asn Ala Asp Ser Gly Glu Ile Ile Tyr Arg His
    210                 215                 220

Ser Ile Pro Ala Val Leu Asn Glu Leu Glu Gly Pro Gly Ile Asp Gly
225                 230                 235                 240

Ala Pro Ser Lys Leu Asn Ala Arg Thr Ser Asp Gly Ser Glu Lys Ile
                245                 250                 255

Ile Val Leu Val Arg Thr Asp Tyr Ser Leu Ser Ala Ser Asp Leu Gly
            260                 265                 270

Lys His Leu Phe Asn Trp Thr Arg Thr Ser Phe Thr Ala Asn Gln Tyr
        275                 280                 285

Ala Lys Tyr Asn His Pro Asp Met Leu Asp Gln Ser Pro Cys Leu Arg
    290                 295                 300

Gly Asp Ile Pro Cys Ile Arg Thr Glu Gly Leu Pro Leu Ala Leu Pro
305                 310                 315                 320

Asp Ser Asp Ser Ala Asn Val Ile Val Leu Lys Asp Gly Thr Pro Phe
                325                 330                 335

Ile Ser Ile His Gly Ser Asp Ala Leu Glu Pro Val Gln Thr Ser Arg
            340                 345                 350

Lys Leu Pro Asn Thr Ala Gly Lys Ser Asn Ile Ile Leu Asp Asp Ser
        355                 360                 365

Gln Asn Gln Thr Tyr Asp Gly Ala Arg Ser His Val Ile Ser Ala Asp
    370                 375                 380

Pro Glu Ala Thr Lys Tyr Pro Thr Arg Asn Thr Tyr Gly Trp Leu Phe
385                 390                 395                 400

Pro Leu Phe Pro Ile Phe Leu Val Ile Gly Tyr Leu Leu Ser Leu Thr
                405                 410                 415

Ser Ala Ser Lys Ser Cys Arg Gln Phe Val Ile Gln Leu Ile Lys Pro
            420                 425                 430

Phe Thr His Asp Lys Lys Ser Val Asp Ile Arg Gly Arg Ser Glu Gly
        435                 440                 445

Thr Pro Lys Arg Arg Lys Thr Arg Lys Lys Asp Gly Leu Ala Asn Ser
    450                 455                 460

Pro Glu Thr Leu Thr Ala Ser Asp Lys Glu Cys Asn Glu Thr Gly Gly
465                 470                 475                 480

Ser Thr Glu Ala Pro Met Glu Asn Ser Ala Leu Thr Asp Ala Leu Gly
                485                 490                 495

Gly Arg Gln Ile Gly Lys Leu Tyr Val Ser Asn Lys Glu Ile Gly Arg
            500                 505                 510

Gly Ser Asn Gly Thr Val Val Phe Glu Gly Ser Tyr Asp Gly Arg Gln
```

```
            515                 520                 525
Val Ala Val Lys Arg Leu Leu Arg Ser His Asn Asp Ile Ala Glu Lys
530                 535                 540

Glu Thr Gln Asn Leu Ile Ile Ser Asp Arg Asp Pro Asn Ile Val Arg
545                 550                 555                 560

Leu Tyr Gly Cys Asp His Ser Asp Phe Val Tyr Ile Ser Leu Glu
                565                 570                 575

Arg Cys His Cys Ser Leu Ala Asp Leu Ile Gln Lys His Ser Tyr Leu
                580                 585                 590

Ser Ser Gly Glu Ser Ile Ser Asn Asn Glu Val Ser Ile Ser Ile Lys
                595                 600                 605

Ser Lys Ile Pro Asn Val Lys Gly Ile Asp Val Glu Leu Trp Thr Gln
610                 615                 620

Asp Gly Leu Pro Ser Ala His Leu Leu Lys Leu Met Arg Asp Val Val
625                 630                 635                 640

Ala Gly Leu Val His Leu His Asn Leu Gly Ile Ile His Arg Asp Leu
                645                 650                 655

Lys Pro Gln Asn Val Leu Ile Ser Ala Glu Gly Thr Ile Arg Ala Lys
                660                 665                 670

Leu Ser Asp Met Gly Ile Ser Lys His Leu Gln Asp Asp Met Thr Ser
                675                 680                 685

Val Ser His His Gly Thr Gly Ile Gly Ser Ser Gly Trp Gln Ala Pro
                690                 695                 700

Glu Gln Leu Arg His Gly Arg Gln Thr Arg Ala Met Asp Leu Phe Ser
705                 710                 715                 720

Leu Gly Cys Leu Ile Phe Tyr Cys Ile Thr Lys Gly Lys His Pro Phe
                725                 730                 735

Gly Glu Tyr Tyr Glu Arg Asp Met Asn Ile Val Asn Asn Arg Phe Asp
                740                 745                 750

Leu Phe Val Val Asp His Ile Pro Glu Ala Val His Leu Ile Ser Gln
                755                 760                 765

Leu Leu Gln Pro Asn Pro Glu Ile Arg Pro Thr Ala Val Tyr Val Met
770                 775                 780

His His Pro Leu Phe Trp Ser Pro Glu Leu Arg Leu Ser Phe Leu Arg
785                 790                 795                 800

Asp Thr Ser Asp Arg Ile Glu Lys Thr Ser Glu Thr Asp Leu Ile Asn
                805                 810                 815

Ala Leu Glu Ser Ile Gly Pro Val Ala Phe Gly Gly Lys Trp Gly Glu
                820                 825                 830

Lys Leu Asp Ala Ala Leu Val Thr Asp Met Gly Arg Tyr Arg Lys Tyr
                835                 840                 845

Asn Phe Glu Ser Ile Arg Asp Leu Leu Arg Tyr Ile Arg Asn Lys Ser
                850                 855                 860

Gly His Tyr Arg Glu Leu Ser Glu Asp Leu Lys Gly Ile Leu Gly Ser
865                 870                 875                 880

Leu Pro Glu Gly Phe Asp Arg Tyr Phe Ala Ser Arg Phe Pro Lys Leu
                885                 890                 895

Leu Ile Glu Val Tyr Lys Val Leu Trp Val His Cys Lys Asp Glu Glu
                900                 905                 910

Ala Phe Ser Lys Tyr Phe Asn Gly Ser Ser Leu
                915                 920

<210> SEQ ID NO 15
```

```
<211> LENGTH: 925
<212> TYPE: PRT
<213> ORGANISM: Zea mays

<400> SEQUENCE: 15

Met Arg Ser Leu Arg Gly Val Leu Ile Pro Leu Val Leu Leu Ala Gly
1               5                   10                  15

Leu Ala Phe Arg Val Asp Asp Gly Gly Ala Ala Leu Leu Pro Leu Pro
            20                  25                  30

Pro Pro Ala Leu Pro Ala Ser Pro Ser Arg Leu Ala Leu Pro Gly Gly
        35                  40                  45

Thr Pro Lys Asp Asp Gly Ala Ala Ser Arg Ser Thr Glu Val Val
50                  55                  60

Thr Ala Gly Val Arg Ser Thr Glu Ile Val Ala Pro Val Gly Pro Lys
65                  70                  75                  80

Lys Gln Ser Leu Arg Glu Leu Leu Val Arg Pro Gln Pro Ala Arg His
                85                  90                  95

Glu Pro Ser Ser Leu Val Ser Gly Glu Ala Lys Ala Glu Thr Arg Ser
            100                 105                 110

Val Leu Gln Phe Tyr Asp Asn Gly Thr Ile Gln Leu Val Asp Lys Leu
        115                 120                 125

Ser Gln Ser Pro Leu Trp Glu Ile Ala Thr Gly Pro Pro Leu Ser Asp
130                 135                 140

His Ile Thr Thr Thr Glu Ser Gly Pro Asn Tyr Leu Ile Tyr Pro Phe
145                 150                 155                 160

Asn Gly Asn Glu Asn Met Asn Gly Asn Ser Thr Glu Leu Trp Glu Val
                165                 170                 175

Tyr Asn Gly Asn Ser Val Arg Leu Pro Trp Lys Leu Glu Glu Phe Val
            180                 185                 190

Ala Arg Ser Pro Tyr Ile Arg Asp Ser Val Val Thr Ile Gly Ser Lys
        195                 200                 205

Val Ser Thr Val Phe Val Val Asp Ala Asp Ser Gly Glu Ile Ile Tyr
210                 215                 220

Arg His Ser Ile Pro Ser Ala Leu Lys Glu Leu Glu Gly Pro Gly Val
225                 230                 235                 240

Glu Gly Ala Pro Ser Lys Leu Asn Val Arg Thr Ser Asp Asp Ser Asp
                245                 250                 255

Asn Ile Ile Val Leu Val Arg Thr Asp Tyr Ser Leu Ser Ala Ser Asp
            260                 265                 270

Leu Gly Asn His Leu Phe Asn Trp Thr Arg Thr Ser Phe Thr Ala Asn
        275                 280                 285

Tyr Tyr Val Lys Tyr Lys His Pro Asp Met Leu Asp Gln Ser Ser Cys
290                 295                 300

Leu Gln Gly Asp Ile Pro Cys Ile Arg Thr Glu Gly Leu Pro Leu Ala
305                 310                 315                 320

Leu Pro Asp Leu Asn Ser Ala Asn Val Ile Val Leu Lys Asp Gly Thr
                325                 330                 335

Pro Phe Val Ser Met His Gly Ser Asp Ala Leu Glu Pro Val Gln Thr
            340                 345                 350

Pro Arg Lys Leu Pro Asn Thr Ala Gly Lys Ser Asn Ile Leu Leu Asp
        355                 360                 365

Asp Ser Gln Asn Gln Thr His Asp Val Ala Arg Ser His Ala Ile Ser
370                 375                 380

Ala Asp Pro Glu Ala Thr Leu Asn Pro Thr Arg Asn Thr Ser Gly Trp
```

```
                385                 390                 395                 400
Leu Phe Pro Leu Phe Pro Ile Phe Leu Val Thr Gly Tyr Leu Leu Ser
                    405                 410                 415

Leu Ile Ser Ala Ser Lys Ser Cys Arg Gln Phe Met Ile Gln Leu Ile
                420                 425                 430

Glu Pro Phe Thr His Asn Lys Lys Thr Val Asp Ile Arg Gly Arg Ser
                435                 440                 445

Glu Gly Thr Pro Lys Lys Arg Lys Thr Arg Lys Lys Asp Gly Leu Val
            450                 455                 460

Asn Ser Ser Glu Thr Leu Thr Ala Ser Asp Lys Glu Cys Ser Asp Thr
465                 470                 475                 480

Gly Gly Ser Thr Glu Ala Pro Met Lys Asn Ser Ala Leu Thr Asp Ala
                    485                 490                 495

Leu Gly Gly Arg Gln Ile Gly Lys Val Tyr Val Ser Asn Lys Glu Ile
                500                 505                 510

Gly Arg Gly Ser Asn Gly Thr Ile Val Phe Glu Gly Ser Tyr Asp Gly
            515                 520                 525

Arg Gln Val Ala Val Lys Arg Leu Leu Arg Ser His Asn Asp Ile Ala
530                 535                 540

Glu Lys Glu Thr Arg Asn Leu Ile Ile Ser Asp His Asp Pro Asn Ile
545                 550                 555                 560

Val Arg Leu Tyr Gly Cys Asp His Asp Ser Asp Phe Val Tyr Ile Ser
                    565                 570                 575

Leu Glu Arg Cys His Cys Ser Leu Ala Asp Leu Ile Gln Lys Gln Ser
                580                 585                 590

Tyr Leu Ser Ser Gly Glu Ser Ile Ser Asn Asn Glu Val Ser Met Ser
            595                 600                 605

Ile Asn Ser Lys Ile Ser Asn Val Lys Gly Ile Asp Val Glu Leu Trp
        610                 615                 620

Thr Gln Asp Gly Leu Pro Ser Ala Gln Leu Leu Lys Leu Met Arg Asp
625                 630                 635                 640

Val Val Ala Gly Leu Val His Leu His Asn Leu Gly Ile Ile His Arg
                    645                 650                 655

Asp Leu Lys Pro Gln Asn Val Leu Ile Ser Ala Glu Gly Pro Ile Arg
                660                 665                 670

Ala Lys Leu Ser Asp Met Gly Ile Ser Lys His Leu Gln Asp Asp Met
            675                 680                 685

Thr Ser Val Ser His His Gly Thr Gly Ile Gly Ser Ser Gly Trp Gln
690                 695                 700

Ala Pro Glu Gln Leu Arg His Gly Arg Gln Thr Arg Ala Met Asp Leu
705                 710                 715                 720

Phe Ser Leu Gly Cys Leu Ile Phe Tyr Cys Ile Thr Lys Gly Lys His
                    725                 730                 735

Pro Phe Gly Glu Tyr Tyr Glu Arg Asp Thr Asn Ile Val Asn Asn Arg
                740                 745                 750

Phe Asp Leu Phe Val Val Asp Tyr Ile Pro Glu Ala Val His Leu Ile
            755                 760                 765

Ser Gln Leu Leu Gln Pro Asn Pro Glu Thr Arg Pro Thr Ala Val Tyr
770                 775                 780

Val Met His His Pro Leu Phe Trp Ser Pro Glu Leu Arg Leu Ser Phe
785                 790                 795                 800

Leu Arg Asp Thr Ser Asp Arg Ile Glu Lys Thr Ser Glu Thr Asp Leu
                    805                 810                 815
```

```
Ile Asn Ala Leu Glu Ser Ile Gly Pro Val Ala Phe Gly Gly Lys Trp
            820                 825                 830
Gly Glu Lys Leu Asp Ala Ala Leu Val Thr Asp Met Gly Arg Tyr Arg
        835                 840                 845
Lys Tyr Asn Phe Glu Ser Thr Arg Asp Leu Leu Arg Tyr Ile Arg Asn
850                 855                 860
Lys Ser Gly His Tyr Arg Glu Leu Ser Asn Asp Leu Lys Gly Ile Leu
865                 870                 875                 880
Gly Ser Leu Pro Glu Gly Phe Asp His Tyr Phe Ala Ser Arg Phe Pro
                885                 890                 895
Lys Leu Leu Ile Glu Val Tyr Lys Val Leu Trp Val His Cys Lys Asp
            900                 905                 910
Glu Glu Ala Phe Ser Lys His Phe Asn Gly Ser Ser Leu
        915                 920                 925

<210> SEQ ID NO 16
<211> LENGTH: 2861
<212> TYPE: DNA
<213> ORGANISM: Brachypodium distachyon

<400> SEQUENCE: 16
```

| | | | | | |
|---|---|---|---|---|---|
| gatttgagca | tgttcttgat | gaggtccttg | gcgctggggg | agatgttggg | ccacgggtcg | 60 |
| gagtcgaagt | ctatggcgcc | ttttaggacc | gcgtcgaaga | tcccctgctg | cgtctcggcc | 120 |
| cagaagggcg | ggacgccgga | gagcaggatg | tagacgatga | ccccgccgt | ccagacgtcg | 180 |
| gcttcgggcc | cgtagtgctt | gcagaggacc | tcggggccca | cgtagtacgg | gcttccgacg | 240 |
| acgtcggtga | agatctggcc | gggcttgaag | aagacggaga | gtccgaaatc | gatggccttg | 300 |
| agatcggcga | ccgagtcgtc | ttcgtcttct | ccgttgccgg | cgccggcgcc | gccgagcaag | 360 |
| aggaagttct | cgggcttgag | gtcgcggtgc | atgaccccca | gagaatggca | cgcctcgacg | 420 |
| acgccgacga | cgacgcgtgc | gatctcggcg | gcttttccgct | cggagaagta | tccgcgggcg | 480 |
| acgatgcggt | cgaagagctc | gccgccctcg | cagaggtcca | tgacgatgtg | gacgtagagc | 540 |
| gggtcctcgt | aggcgccgcg | gatggtgacg | acgctggcgt | ggcccgccag | gtggtgcatg | 600 |
| atctggatct | cgcggcggac | gtcgtccacg | tcctcggggg | tgaggagctt | gcgcttggcg | 660 |
| atggacttgc | aggcgagggg | tgtccccgtg | gcgatgtcgg | tgcagaggta | ggtggtgccg | 720 |
| aactggcccct | ggccgagctt | gcggccgagc | gtgtagaggg | aggtgagcgg | cggggtgtcg | 780 |
| tggccgagga | cggcggtcgg | ggaggagagg | tggtgctggt | ggccgcgcat | ggtgttggtg | 840 |
| gtgcaggggg | cttggaggtg | gagatggaag | gggtccgagt | cggcggtgct | gctgttggaa | 900 |
| tcgcggcacg | agtagttgcc | catgcgcacc | gcgtcaattg | tcgccggcgg | ccatggcgac | 960 |
| caccgtggat | ggatgattgg | accacagaga | aattagggg | tggagaggaa | gaggagagct | 1020 |
| gtgctccatt | agtttgggag | gaagaggaga | ccaaattggc | aatggcctgc | atgtcgtgcg | 1080 |
| ctgcacctac | ctaagctagc | gtgcatgtcg | atttgctcct | gcgacaccac | gattcggccc | 1140 |
| tttttcggcc | taaatgaaac | atcgtccatc | tcgaatcaac | ctagccacat | cattcttttt | 1200 |
| cttttttgcaa | gatcgatccc | tgtgcagtag | acatgcatgc | tggagtagca | gtaggaatca | 1260 |
| gggactggcc | agcctggcct | tgctagtgag | cgagtgtacg | tgcaatgcca | attaaccgtt | 1320 |
| tgcttatttt | actagtacca | tcatatcgat | cgatctcaat | caagctgctg | acgtagggca | 1380 |
| acatatataa | gatcgttttc | agctcgtggt | gcacgatgcg | caataatacc | gatcctgtta | 1440 |
| gttgagttca | atcaattaag | agctctgttt | cctcatctct | cacctacgag | aagcggcgca | 1500 |

-continued

```
tacagaaata gaagatgttg aggtagatca agttcatatt gatgttaact tgaatactta    1560
ttgaagattt caattcaaag gacactagaa gaatgatgct gttcaaataa agatgttgag    1620
gtagaggaag ttcattattc tagtactttt ctagtgaggg agattttcgc acctgcatgt    1680
atttattgct gtcaaatata tgacgccaat gaaatagaaa aatactctta attaataata    1740
tgcgataata aattatttta ccccggccgg tggtttattt ttcttgcttc gcgcccctgc    1800
ctagcgagga gaggtgcatg cgatccaccg gcccatggat cgtcgcttaa ttagtaccgg    1860
taatttcctt attaaaccag gaatgcaaat aattcatgtc ctggacagtg agatgatgag    1920
caggtcggcg ggtatgcgcg cgaacgtacg gtctctgtcg atcgtgtgcc acgtgcatta    1980
gcggagccga cggcctgctc gcagagcccg acaaattcc ctaaaaatta attatacaag     2040
aaaaacacta ctctggtggc taattaacac gctggctagc ggcatcatgg cttcccagt     2100 gatcgatagc actggggaag catgcatagc tcgatggaat cactccatgc gagtgcatat    2160
gtcgcaccaa ccaaatttct ttcgtcactt agtatgaaac ggagagaatg tatgatcgac    2220
cgattctgat cccgcatgat aatagtgaga tcgattctgg tcccgcatga taataatgag    2280
atctcaacaa attaaccaac aaacataca ttgcacatgc ctgcctatac tacttatcac     2340
cgtccaaatt aaagcattca tgccaccta gctaaaaata gatacatcca tatttaaaca    2400
aatttgaatt aagaatttag aaacgggagc aggcaggaac aatccagcgg cttcttattg    2460
actctgtcaa cacaacacta gctagctggg ttttcagact tcattaacag cgcacgctag    2520
cggcatcatg gcttcccaag tgagcggtcg agcgccgaca aaacgggac cccggccctc      2580 tgtgtgattt gatgcgagtt gctagcagtg tgtctgacac tgtgatgttt ggtccaggta    2640
tgaaccaacc aagatcacag gaaaaaaaac aatcgcacat gcatgtatga atctcctccg    2700
gcctatatat actcgccacc atctcggaat taaagcatgc atgccactta cagcaggctt    2760
gcatcaccag ctgccactca gctgggtttt catcagtctt aaactgagct gtgttaatta    2820
cctgagcaca cacacagctc aagtctgaac aagctagtaa g                        2861
```

<210> SEQ ID NO 17
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 17
caagcatccg tttggtgagt                                                 20

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 18
tcacgtatac tgccgttggt                                                 20

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide sequence

```
<400> SEQUENCE: 19
cagcatttgc cttgacattc                                              20

<210> SEQ ID NO 20
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 20
gcagcgaaca gatagacagg                                              20
```